United States Patent
Koga et al.

(10) Patent No.: US 6,174,458 B1
(45) Date of Patent: Jan. 16, 2001

(54) TETRACYCLIC COMPOUND HAVING LATERAL HALOGEN SUBSTITUENT AND LIQUID CRYSTAL COMPOSITION COMPRISING THE SAME

(75) Inventors: Koji Koga; Tsugumichi Ando; Hiroyuki Takeuchi; Shuichi Matsui; Kazutoshi Miyazawa, all of Chiba; Norihisa Hachiya, Saitama; Etsuo Nakagawa, Chiba, all of (JP)

(73) Assignee: Chisso Corporation, Osaka (JP)

( * ) Notice: Under 35 U.S.C. 154(b), the term of this patent shall be extended for 0 days.

(21) Appl. No.: 09/242,921

(22) PCT Filed: Aug. 18, 1997

(86) PCT No.: PCT/JP97/02848

§ 371 Date: Feb. 26, 1999

§ 102(e) Date: Feb. 26, 1999

(87) PCT Pub. No.: WO98/08792

PCT Pub. Date: Mar. 5, 1998

(30) Foreign Application Priority Data

Aug. 28, 1996 (JP) .................................................. 8-245525

(51) Int. Cl.$^7$ .......................... C09K 19/30; C09K 19/34; C09K 19/12; C09K 19/06; C07C 19/08
(52) U.S. Cl. .................. 252/299.63; 252/299.61; 252/299.66; 252/299.6; 570/129
(58) Field of Search .................. 252/299.66, 299.63, 252/299.6, 299.61; 570/129

(56) References Cited

U.S. PATENT DOCUMENTS

| | | | |
|---|---|---|---|
| 4,477,369 | 10/1984 | Sugimori et al. | 252/299.6 |
| 5,061,400 | 10/1991 | Obikawa | 252/299.63 |

FOREIGN PATENT DOCUMENTS

| | | |
|---|---|---|
| 3921836 | 1/1990 | (DE) . |
| 4425642 * | 1/1996 | (DE) . |
| 2134110 | 8/1984 | (GB) . |
| 2240778 | 8/1991 | (GB) . |
| 58-203922 | 11/1983 | (JP) . |
| 2-237949 | 9/1990 | (JP) . |
| 4-312540 | 11/1992 | (JP) . |
| 4-356432 | 12/1992 | (JP) . |
| 5-255151 * | 5/1993 | (JP) . |
| WO91/08184 | 6/1991 | (WO) . |
| WO97/27166 * | 7/1997 | (WO) . |
| WP 98/13321 * | 4/1998 | (WO) . |

OTHER PUBLICATIONS

Database WPI, Section Ch, Week 9304, Derwent Publications Ltd., London, GB; Class E14, AN 93–030492, XP002047406 & JP 04 356 432 A (Seiko Epson Corp), Dec. 10, 1992.

Database WPI, Section Ch, Week 9251, Derwent Publications Ltd., London, GB; Class E14, AN 92–418591, XP002047407 & JP 04 312 540 A (Seiko Epson Corp), Nov. 4, 1992.

Balkwill et al., "Fluorination in nematic systems", Molecular Crystals and Liquid Crystals Letters, vol. 123, No. 1/4, 1985, pp. 1–13.

* cited by examiner

*Primary Examiner*—C. H. Kelly
(74) *Attorney, Agent, or Firm*—Wenderoth, Lind & Ponack, L.L.P.

(57) ABSTRACT

A tetracyclic compound expressed by the following general formula (1)

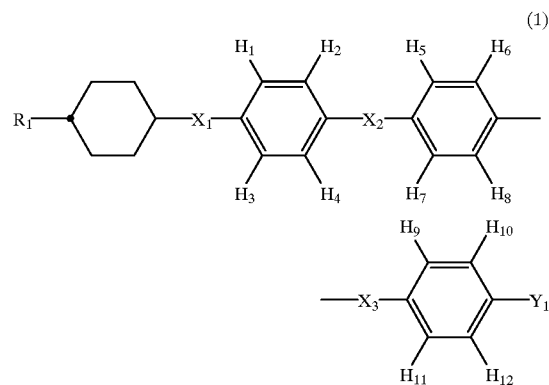

wherein $H_1$ to $H_{12}$ represent hydrogen atom at least one of which is replaced by a halogen atom, when either $H_6$ or $H_8$ is replaced by a halogen atom, at least one of the remaining hydrogen atoms is replaced by a halogen atom; $R_1$ and $Y_1$ independently represent an alkyl group, alkoxy group, or alkoxyalkyl group having 1 to 20 carbon atoms, or an alkenyl group having 2 to 20 carbon atoms, one or more methylene group in $R_1$ and $Y_1$ may be replaced by oxygen atom, sulfur atom, dihydrosilylene group, dimethylsilylene group, —CH=CH—, or —C≡C—; and $X_1$, $X_2$, and $X_3$ independently represent a covalent bond, 1,2-ethylene group, or 1,4-butylene group; and a novel liquid crystal composition comprising the tetracyclic compound and having, at the same time, a wide temperature range of a nematic phase, high optical anisotropy, and high chemical stability.

17 Claims, No Drawings

TETRACYCLIC COMPOUND HAVING LATERAL HALOGEN SUBSTITUENT AND LIQUID CRYSTAL COMPOSITION COMPRISING THE SAME

TECHNICAL FIELD

The present invention relates to a novel liquid crystalline compound, a liquid crystal composition comprising the compound, and a liquid crystal display device comprising the composition. Specifically, the present invention relates to a liquid crystalline compound which has a wide temperature range of a nematic phase, a high clearing point, and a good miscibility with other liquid crystalline compounds, and thus develops preferable properties as electrooptical display material; and relates to a liquid crystal composition having preferable properties such as a wide driving temperature range.

BACKGROUND ART

Liquid crystal display devices utilize optical anisotropy and dielectric anisotropy of liquid crystalline compounds. As driving mode of the liquid crystal display devices, active matrix driving mode using a TFT has attracted most public attention since it has a high display capability.

While various properties are required of the liquid crystalline compounds used for the driving mode described above, the followings are generally considered to be necessary:

1) Liquid crystalline compounds have a wide temperature range of nematic phase to actualize a wide range of a driving temperature. Alternatively, the compounds do not reduce the temperature range of a nematic phase or they hardly cause phase separation such as formatin of crystals at a low temperature region when they are added in liquid crystal compositions.

2) Liquid crystalline compounds have a low viscosity to actualize a high response speed.

3) Liquid crystalline compounds have a high optical anisotropy.

In order to realize liquid crystal compositions having such properties as described above, a means has been adopted wherein liquid crystalline compounds having a low viscosity, very wide temperature range of a nematic phase, and particularly a high clearing point are used as base liquid crystal, and a proper amount of other liquid crystalline compounds having a distinctive optical anisotropy are mixed therewith to obtain desired properties.

In order to obtain liquid crystal compositions which can be driven at a wide temperature range, liquid crystalline compounds having a driving temperature range as wide as possible, that is, a S-N point or melting point as low as possible, a clearing point as high as possible, and a temperature range of a nematic phase as wide as possible are necessary.

Further, liquid crystal compositions are generally composed of a mixture of several or thirty-odd liquid crystalline compounds to exhibit properties required for particular display devices. Accordingly, liquid crystalline compounds are required to have a good miscibility with other liquid crystalline compounds. Since environment of their use extends over a wide area lately, good miscibility at low temperatures is especially required.

Namely, liquid crystal compositions are necessary to have a nematic phase especially at low temperatures for their use in a wide temperature range, and liquid crystal compositions which do not form crystals or do not exhibit a smectic phase are required. Accordingly, it is extremely important that liquid crystalline compounds to be used have a high miscibility at low temperatures with other liquid crystalline compounds.

Various tetracyclic compounds or four ring compounds have already been disclosed, for example, in Laid-open Japanese Patent Publication Nos. Hei 4-312,540 and Hei 4-356,432, aiming at the purposes of simultaneously satisfying the wide temperature range of a nematic phase, good miscibility, and large optical anisotropy described above. Besides, compounds expressed by the general formula of

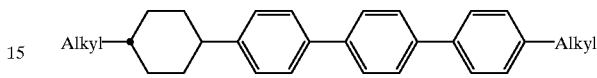

are disclosed in Laid-open Japanese Patent Publication No. Sho 58-203,922 (JP '922) and the compounds expressed by the general formula of

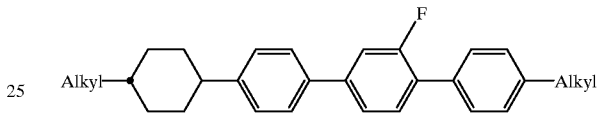

are disclosed in Laid-open Japanese Patent Publication No. Hei 2-237,949 (JP '949), respectively.

Whereas the compounds of either publication exhibit a high optical anisotropy, ones of JP '922 are very poor in the miscibility and ones of JP '949 have a narrow temperature range of a nematic phase. In Mol. Cryst. Liq. Cryst., 1985, Vol. 123, pages 1–13, GB-A-2240 778, WO-A-91 08184, and GB-A-2 134 110, various tetracyclic compounds have been disclosed. However, these compounds are not satisfactory in their temperature range of nematic phase, clearing point, and miscibility with other liquid crystalline compounds. Accordingly, new liquid crystalline compounds having more excellent properties were long-awaited.

Liquid crystalline compounds used for liquid crystal compositions must be stable against outside environmental factors such as moisture, air, heat, and light. Particularly, the liquid crystal compositions designed for liquid crystal displays of active matrix mode which comprise integrated non-linear devices for switching individual image segments must have an extremely high specific resistance (a high voltage holding ratio) and good UV stability (UV resistance).

Liquid crystal display devices of active matrix mode are suitable for TV sets, computers, and instruments used in automobiles or airplanes all of which display a high degree of information. However, when liquid crystalline compounds or liquid crystal compositions which do not have an extremely high specific resistance (a high voltage holding ratio) and good UV stability are used, contrast decreases with decreasing of electric resistance within a liquid crystal panel, which causes a problem of "phenomenon of image sticking". Particularly, when the liquid crystal display devices are driven at low voltages, electric resistance of the liquid crystal compositions is an extremely important factor which controls utility life of the devices. Thus, an extremely high specific resistance (high voltage holding ratio) and good UV stability are very important properties required of liquid crystal compositions to be used.

In order to provide the liquid crystal compositions having excellent properties, new liquid crystalline compounds having a wider temperature range of a nematic phase, high miscibility with other liquid crystalline compounds at low temperatures, high chemical stability, and high optical anisotropy simultaneously were long-awaited.

DISCUSSION OF THE INVENTION

An object of the present invention is to provide novel liquid crystalline compounds having simultaneously a wide temperature range of a nematic phase, good miscibility with other liquid crystalline compounds at low temperatures, high optical anisotropy, and high chemical stability, and to provide liquid crystal compositions comprising the compounds and having excellent properties.

As a result of the investigation by the present inventors to solve the problems described above, compounds having a new structure and having improved properties compared with conventional liquid crystalline compounds have now been found.

In other words, it has been found that a peculiarly wide temperature range of a nematic phase and remarkably improved miscibility can be induced by introducing one or more halogen atoms to a specific position of benzene rings in the skeleton of 4-cyclohexylterphenyl or the skeleton of similar four rings, leading to the accomplishment of the present invention.

That is, the present invention relates to a tetracyclic compounds or four ring compounds expressed by the following general formula (1)

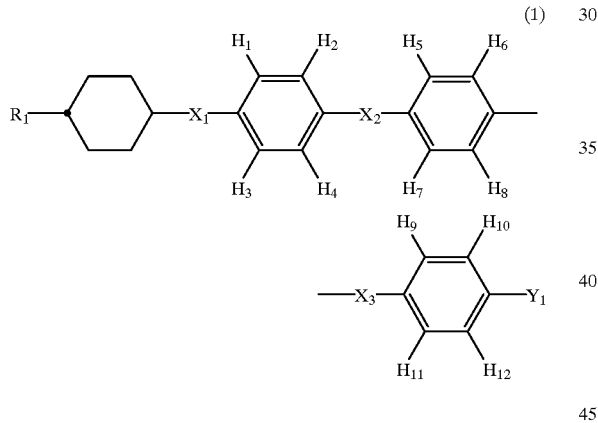

(1)

wherein $H_1$ to $H_{12}$ represent hydrogen atom at least one of $H_1$ to $H_{12}$ is replaced by a halogen atom, and when either $H_6$ or $H_8$ is replaced by a halogen atom, at least one of the remaining hydrogen atoms is replaced by a halogen atom; $R_1$ and $Y_1$ independently represent an alkyl group, alkoxy group, or alkoxyalkyl group having 1 to 20 carbon atoms, or an alkenyl group having 2 to 20 carbon atoms, one or more methylene groups in $R_1$ or $Y_1$ may be replaced by oxygen atom, sulfur atom, dihydrosilylene group, dimethylsilylene group, —CH=CH—, or —C≡C—: and $X_1$, $X_2$, and $X_3$ independently represent a covalent bond, 1,2-ethylene group, or 1,4-butylene group.

A specific embodiment of the present invention is concerned with tetracyclic compounds expressed by the general formula (1) wherein hydrogen atom of $H_1$ and $H_4$ are replaced by a halogen atom, and $H_2$, $H_3$, and $H_5$ to $H_{12}$ represent hydrogen atom.

Another specific embodiment of the present invention is concerned with tetracyclic compounds expressed by the general formula (1) wherein hydrogen atom of $H_1$ is replaced by a halogen atom, and $H_2$ to $H_{12}$ represent hydrogen atom.

Still another embodiment of the present is concerned with tetracyclic compounds expressed by the general formula (1) wherein hydrogen atom of $H_5$ is replaced by a halogen atom, and $H_1$ to $H_4$, and $H_6$ to $H_{12}$ represent hydrogen atom.

Still another embodiment of the present invention is concerned with tetracyclic compounds expressed by the general formula (1) wherein hydrogen atom of $H_2$ and $H_4$ are replaced by a halogen atom, and $H_1$, $H_3$, and $H_5$ to $H_{12}$ represent hydrogen atom.

Still another embodiment of the present invention is concerned with tetracyclic compounds expressed by the general formula (1) wherein hydrogen atom of $H_6$ and $H_8$ are replaced by a halogen atom, and $H_1$ to $H_5$, $H_7$, and $H_9$ to $H_{12}$ represent hydrogen atom.

Still another embodiment of the present invention is concerned with tetracyclic compounds expressed by the general formula (1) wherein hydrogen atom of $H_1$ and $H_5$ are replaced by a halogen atom, and $H_2$ to $H_4$, and $H_6$ to $H_{12}$ represent hydrogen atom.

Still another embodiment of the present invention is concerned with tetracyclic compounds expressed by the general formula (1) wherein hydrogen atom of $H_1$ and $H_9$ are replaced by a halogen atom, and $H_2$ to $H_8$, and $H_{10}$ to $H_{12}$ represent hydrogen atom.

Still another embodiment of the present inventthe general formula (1) wherein hydrogen atom of $H_2$ and $H_9$ are replaced by a halogen atom, and $H_1$, $H_3$ to $H_8$, and $H_{10}$ to $H_{12}$ represent hydrogen atom.

Further, the present invention relates to a liquid crystal composition comprising at least one tetracyclic compound expressed by the general formula (1).

In a specific embodiment, the liquid crystal composition of the present invention comprises, as a first component, at least one tetracyclic compound expressed by the general formula (1), and comprises, as a second component, at least one compound selected from the group consisting of the compounds expressed by any one of the general formulas (2), (3), and (4)

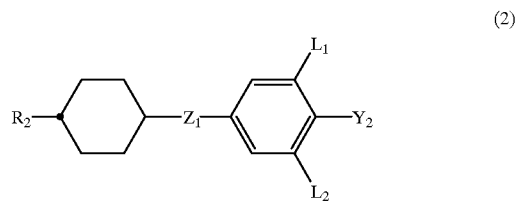

(2)

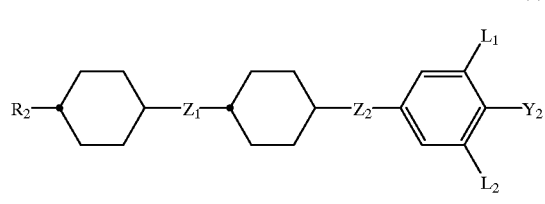

(3)

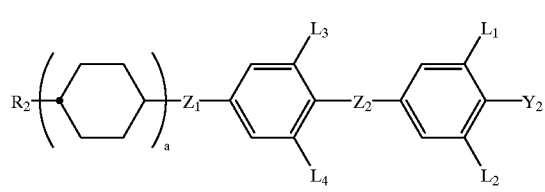

(4)

wherein $R_2$ represents an alkyl group having 1 to 10 carbon atoms; $Y_2$ represents fluorine atom, chlorine atom, $OCF_3$, $OCF_2H$, $CF_3$, $CF_2H$, or $CFH_2$; $L_1$, $L_2$, $L_3$, and $L_4$ independently represent hydrogen atom or fluorine atom; $Z_1$ and $Z_2$ independently represent 1,2-ethylene group, —CH=CH—, or a covalent bond; and a is 1 or 2.

In another specific embodiment, the liquid crystal composition of the present invention comprises, as a first component, at least one tetracyclic compound expressed by the general formula (1), comprises, as a second component, at least one compound selected from the group consisting of the compounds expressed by any one of the general formulas (5), (6), (7), (8), and (9)

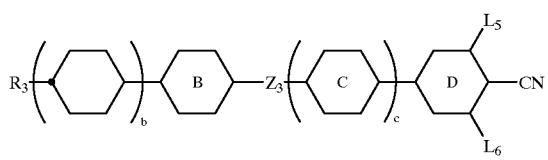

(5)

wherein $R_3$ represents fluorine atom, an alkyl group having 1 to 10 carbon atoms or an alkenyl group having 2 to 10 carbon atoms, any methylene group in the alkyl or alkenyl group may be replaced by oxygen atom, but in no case two or more methylene groups are continuously replaced by oxygen atom; ring B represents 1,4-cyclohexylene, 1,4-phenylene, or 1,3-dioxane-2,5-diyl; ring C represents 1,4-cyclohexylene, 1,4-phenylene, or pyrimidine-2,5-diyl; ring D represents 1,4-cyclohexylene or 1,4-phenylene; $Z_3$ represents 1,2-ethylene group, —COO—, or a covalent bond; $L_5$ and $L_6$ independently represent hydrogen atom or fluorine atom, and b and c are independently 0 or 1,

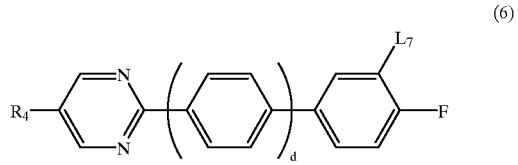

(6)

wherein $R_4$ represents an alkyl group having 1 to 10 carbon atoms, $L_7$ represents hydrogen atom or fluorine atom; and d is 0 or 1,

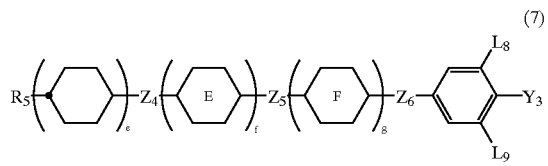

(7)

wherein $R_5$ represents an alkyl group having 1 to 10 carbon atoms; ring E and ring F independently represent 1,4-cyclohexylene or 1,4-phenylene; $Z_4$ and $Z_5$ independently represent —COO— or a covalent bond; $Z_6$ represents —COO— or —C≡C—; $L_8$ and $L_9$ independently represent hydrogen atom or fluorine atom; $Y_3$ represents fluorine atom, $OCF_3$, $OCF_2H$, $CF_3$, $CF_2H$, or $CFH_2$; and e, f, and g are independently 0 or 1,

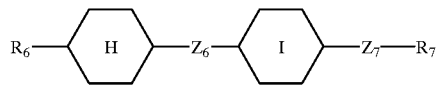

(8)

wherein $R_6$ and $R_7$ independently represent an alkyl group having 1 to 10 carbon atoms or an alkenyl group having 2 to 10 carbon atoms, any methylene group in the alkyl or alkenyl group may be replaced by oxygen atom, but in no case two or more methylene groups are continuously replaced by oxygen atom; ring H represents 1,4-cyclohexylene, 1,4-phenylene, or pyrimidine-2,5-diyl; ring I represents 1,4-cyclohexylene or 1,4-phenylene; $Z_6$ represents —C≡C—, —COO—, 1,2-ethylene group, —CH=CH—C≡C—, or a covalent bond; and $Z_7$ represents —COO— or a covalent bond,

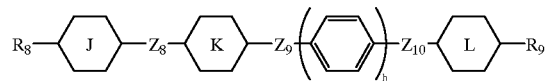

(9)

wherein $R_8$ and $R_9$ independently represent an alkyl group having 1 to 10 carbon atoms or an alkenyl group having 2 to 10 carbon atoms, any methylene group in the alkyl or alkenyl group may be replaced by oxygen atom, but in no case tow or more methylene groups are continuously replaced by oxygen atom; ring J represents 1,4-cyclohexylene, 1,4-phenylene, or pyrimidine-2,5-diyl; ring K represents 1,4-cyclohexylene, 1,4-phenylene in which one or more hydrogen atoms on the ring may be replaced by fluorine atom, or pyrimidine-2,5-diyl; ring L represents 1,4-cyclohexylene or 1,4-phenylene; $Z_8$ and $Z_{10}$ independently represent —COO—, 1,2-ethylene group, or a covalent bond; $Z_9$ represents —CH=CH—, —C≡C—, —COO—, or a covalent bond; and h is 0 or 1.

In still another embodiment, the liquid crystal composition of the present invention comprises, as a first component, at least one tetracyclic compound expressed by the general formula (1), comprises, as a part of a second component, at least one compound selected from the group consisting of the compounds expressed by any one of the general formulas (2), (3), and (4), and comprises, as the other portion of the second component, at least one compound selected from the group consisting of the compounds expressed by any one of the general formulas (5), (6), (7), (8), and (9).

Still further, the present invention relates to a liquid crystal display device comprising the liquid crystal composition described above.

BEST MODE FOR CARRYING OUT THE INVENTION

Compounds of the present invention expressed by the general formula (1) are tetracyclic compounds characterized by having the benzene ring hydrogen atom of which is replaced by a halogen atom, and compounds expressed by any one of the following formulas (1-1) to (1-8) can be mentioned as specific examples:

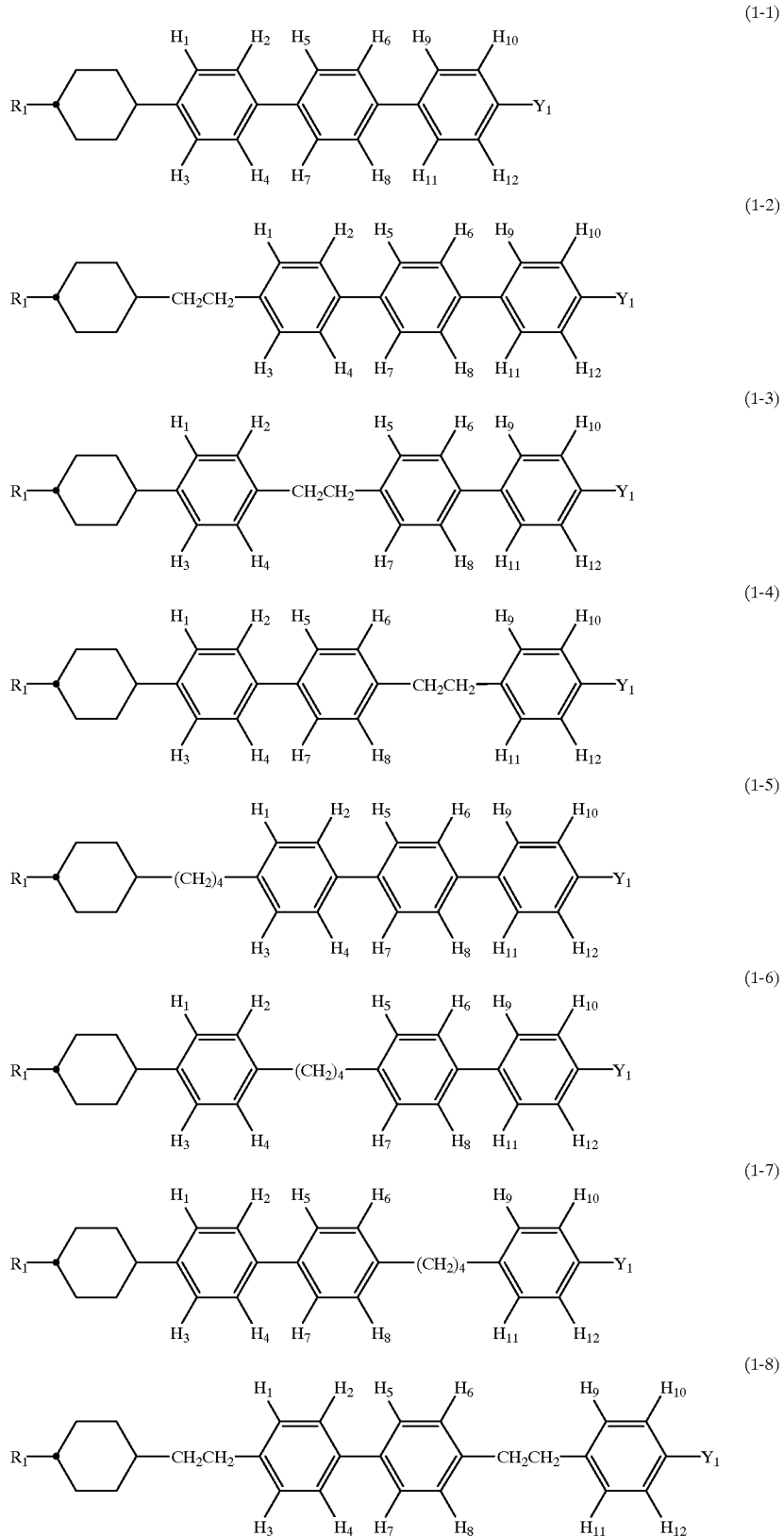
wherein $R_1$, $Y_1$, and $H_1$ to $H_{12}$ have the same meaning as described above.
That is, the tetracyclic compounds expressed by the general formula (1) can be developed into compounds expressed by the formula (1-1) in which all rings are linked with a covalent bond; compounds containing one 1,2-ethylene bond and expressed by one of the formulas (1-2) to (1-4); compounds containing one 1,4-butylene bond and expressed by one of the formulas (1-5) to (1-7); and compounds containing two 1,2-ethylene bonds and expressed by the formula (1-8).

Those compounds can further be developed into the following compounds:

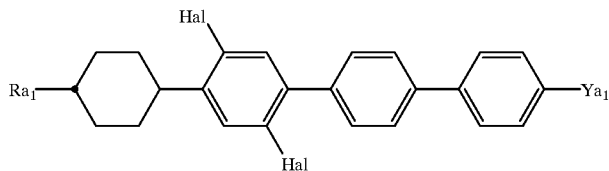
(1-1-1)

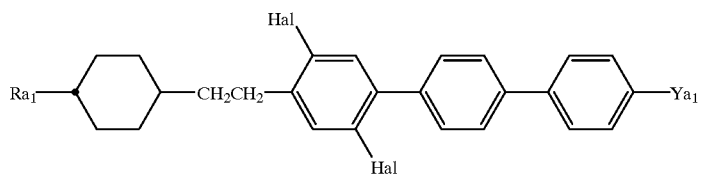
(1-2-1)

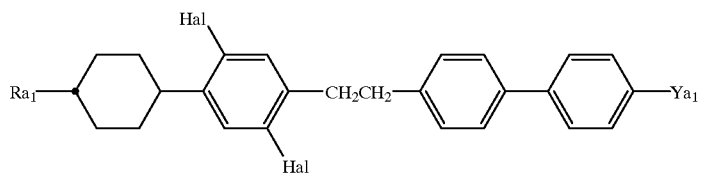
(1-3-1)

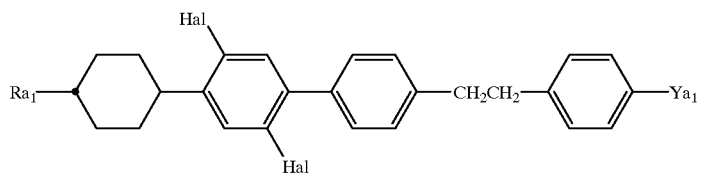
(1-4-1)

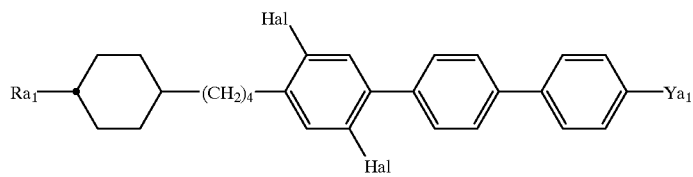
(1-5-1)

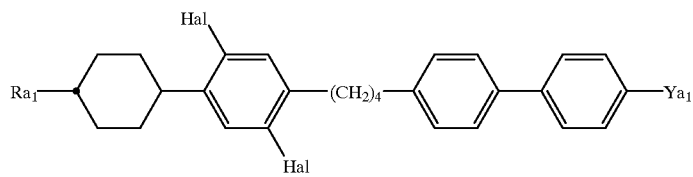
(1-6-1)

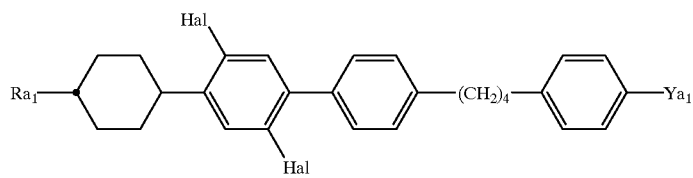
(1-7-1)

(1-8-1)
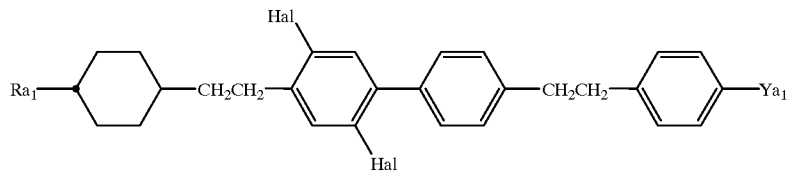
(1-1-2)
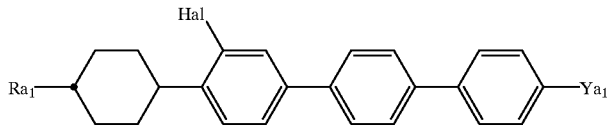
(1-2-2)
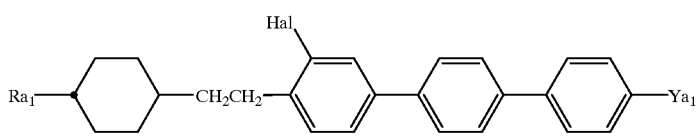
(1-3-2)
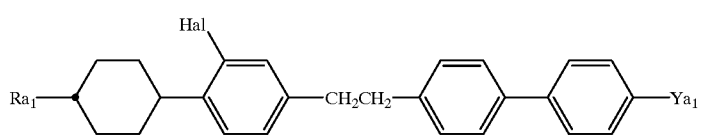
(1-4-2)
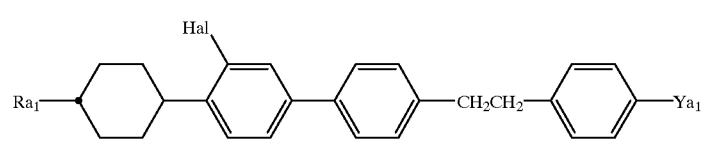
(1-5-2)
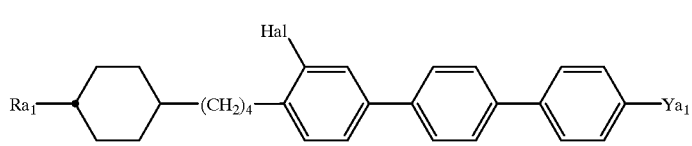
(1-6-2)
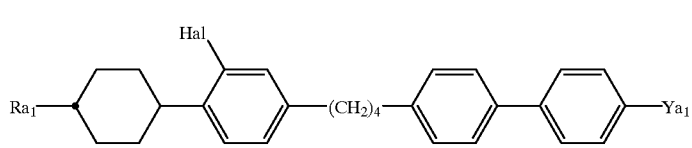
(1-7-2)
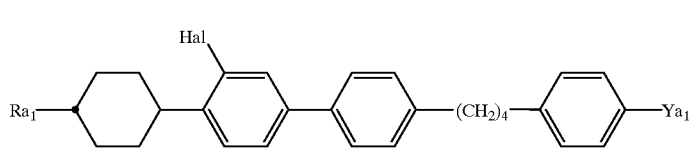
(1-8-2)
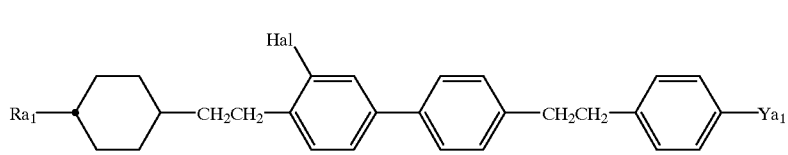
(1-1-3)
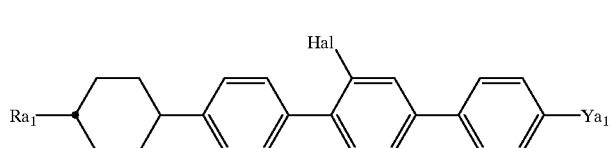

-continued
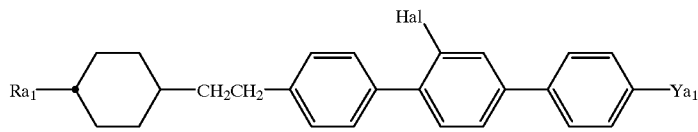
(1-2-3)
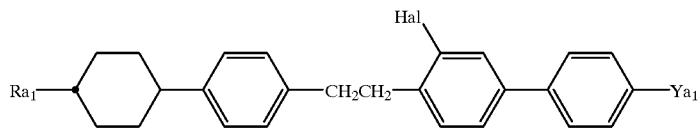
(1-3-3)
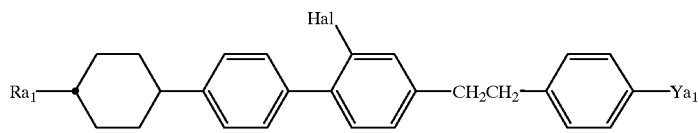
(1-4-3)
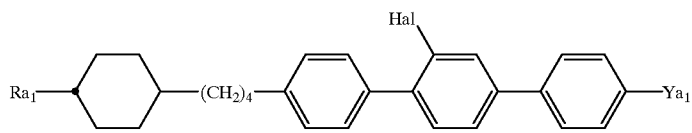
(1-5-3)
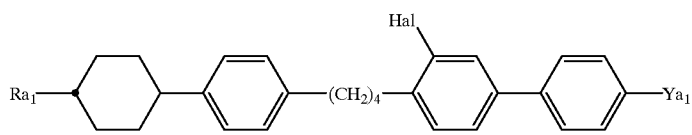
(1-6-3)
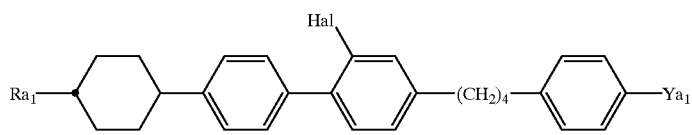
(1-7-3)
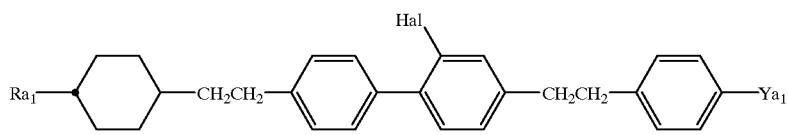
(1-8-3)
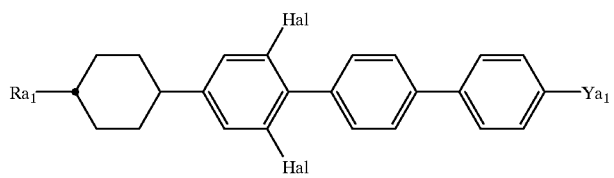
(1-1-4)
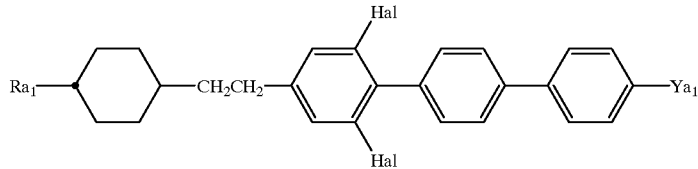
(1-2-4)

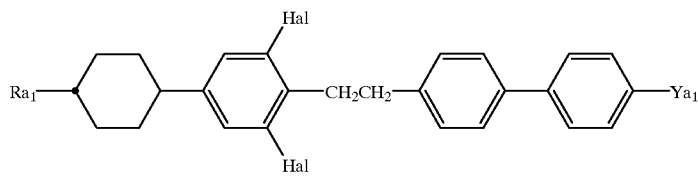
(1-3-4)
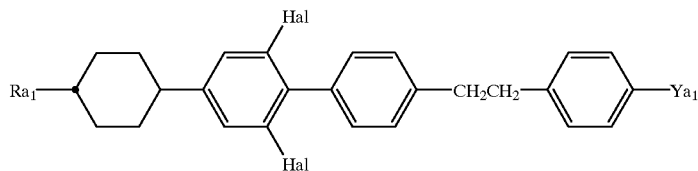
(1-4-4)
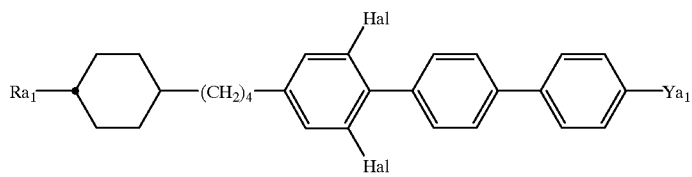
(1-5-4)
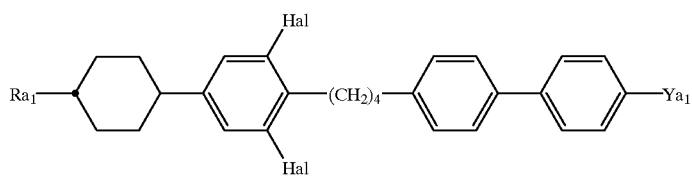
(1-6-4)
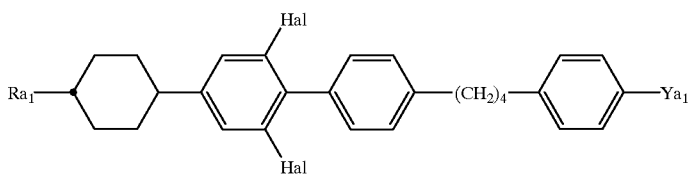
(1-7-4)
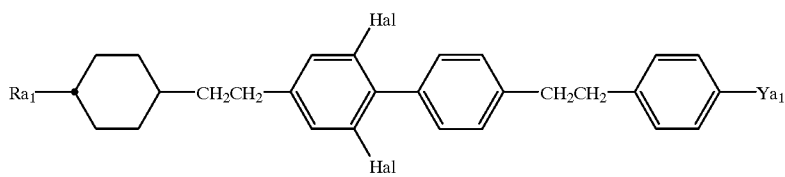
(1-8-4)
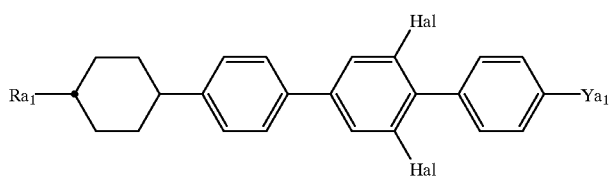
(1-1-5)
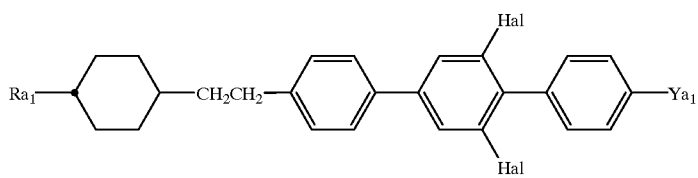
(1-2-5)

-continued
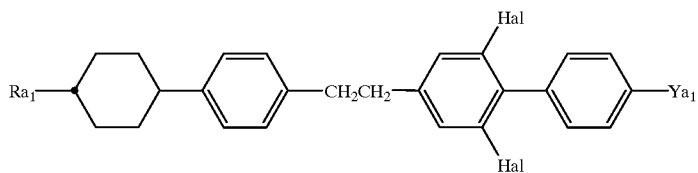
(1-3-5)
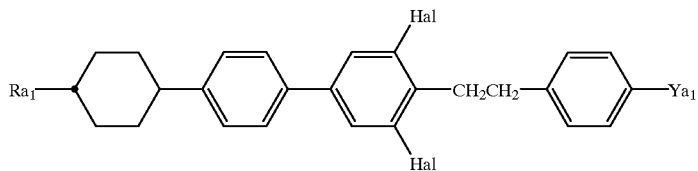
(1-4-5)
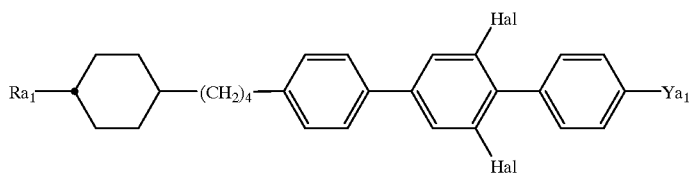
(1-5-5)
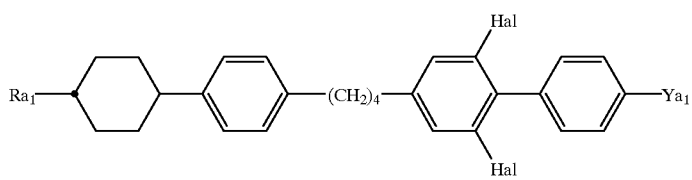
(1-6-5)
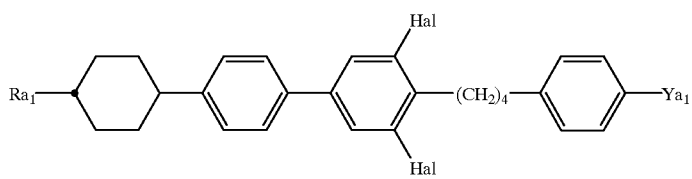
(1-7-5)
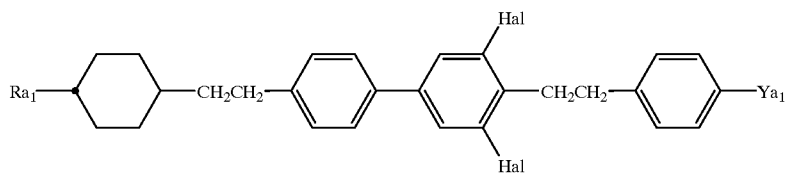
(1-8-5)
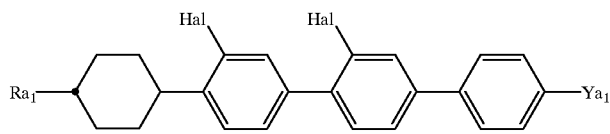
(1-1-6)
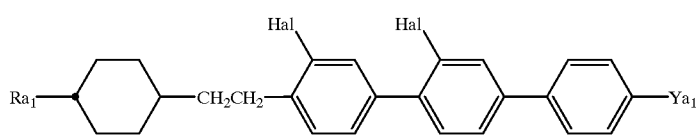
(1-2-6)

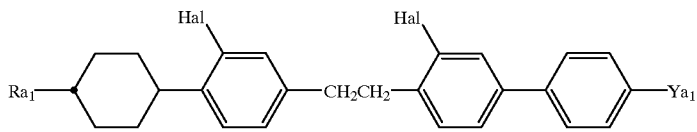
(1-3-6)
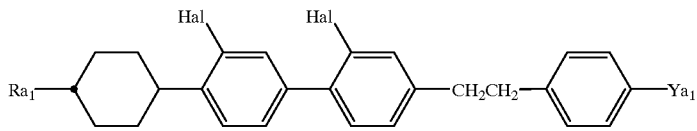
(1-4-6)
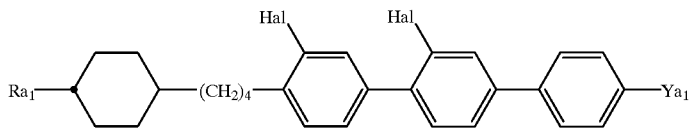
(1-5-6)
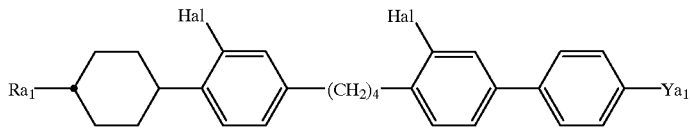
(1-6-6)
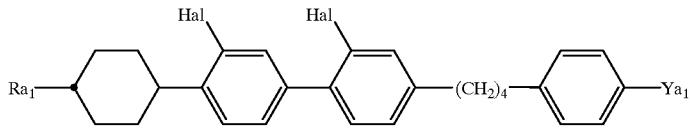
(1-7-6)
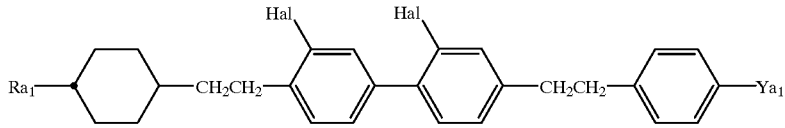
(1-8-6)
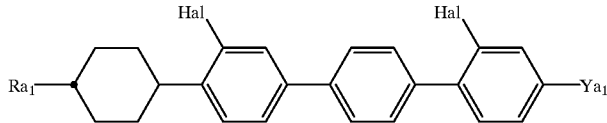
(1-1-7)
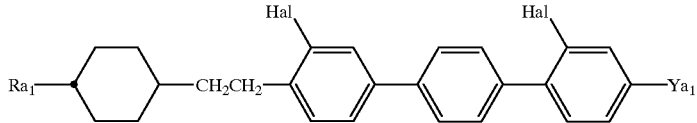
(1-2-7)
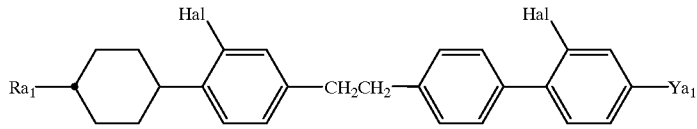
(1-3-7)
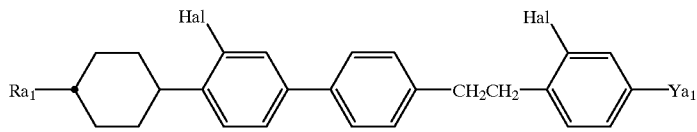
(1-4-7)

-continued
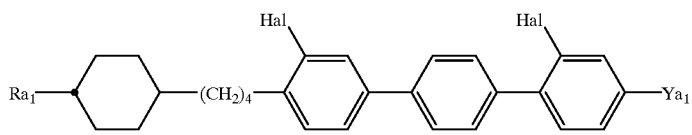 (1-5-7)
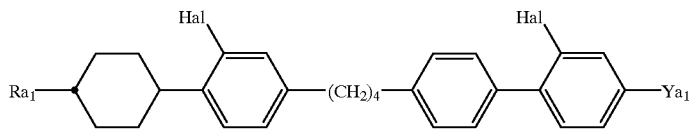 (1-6-7)
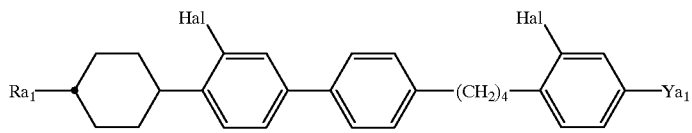 (1-7-7)
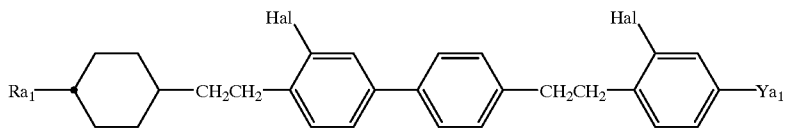 (1-8-7)
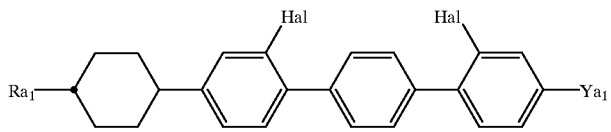 (1-1-8)
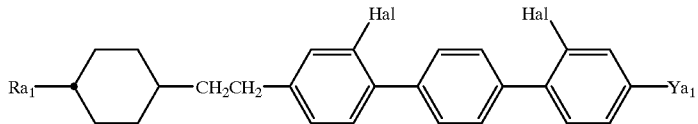 (1-2-8)
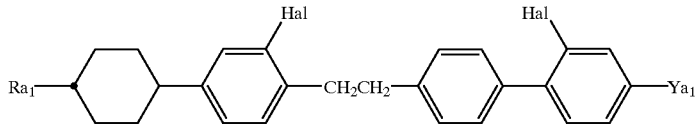 (1-3-8)
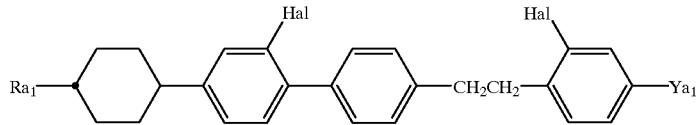 (1-4-8)
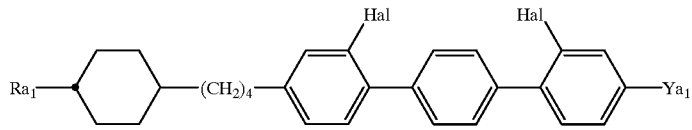 (1-5-8)
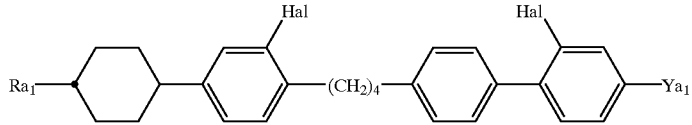 (1-6-8)

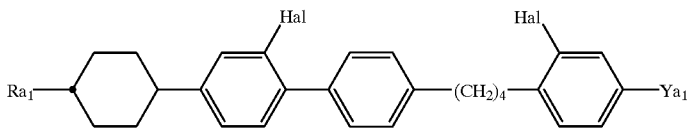

(1-7-8)

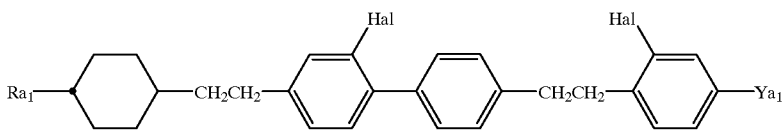

(1-8-8)

wherein $Ra_1$ and $Ya_1$ represent an alkyl group, alkoxy group, alkoxyalkyl group, or alkenyl group, and Hal represents fluorine atom or chlorine atom.

While $R_1$ and $Y_1$ in the general formula (1) represent an alkyl group having 1 to 20 carbon atoms, methylene group in the $R_1$ or $Y_1$ may be replaced by oxygen atom, sulfur atom, dihydrosilylene group, dimethylsilylene group, —CH=CH—, or —C≡C—.

Among them, preferable $R_1$ and $Y_3$ are mentioned more specifically as follows:

Methyl group, ethyl group, propyl group, butyl group, pentyl group, hexyl group, heptyl group, octyl group, methoxymethyl group, ethoxymethyl group, propoxymethyl group, butoxymethyl group, pentoxymethyl group, hexyloxymethyl group, heptyloxymethyl group, octyloxymethyl group, methoxyethyl group, ethoxyethyl group, propoxyethyl group, pentoxyethyl group, hexyloxyethyl group, methoxypropyl group, ethoxypropyl group, propoxypropyl group, pentoxypropyl group, hexyloxypropyl group, heptyloxypropyl group, methoxybutyl group, ethoxybutyl group, propoxybutyl group, butoxybutyl group, pentoxybutyl group, methoxypentyl group, ethoxypentyl group, propoxypentyl group, pentoxypentyl group, methoxymethoxy group, ethoxymethoxy group, propoxymethoxy group, butoxymethoxy group, pentoxymethoxy group, hexyloxymethoxy group, heptyloxymethoxy group, octyloxymethoxy group, methoxyethoxy group, ethoxyethoxy group, propoxyethoxy group, butoxyethoxy group, pentoxyethoxy group, hexyloxyethoxy group, methoxypropoxy group, ethoxypropoxy group, propoxypropoxy group, pentoxypropoxy group, hexyloxypropoxy group, heptyloxypropoxy group, methoxybutoxy group, ethoxybutoxy group, propoxybutoxy group, butoxybutoxy group, pentoxybutoxy group, methoxypentoxy group, ethoxypentoxy group, propoxypentoxy group, pentoxypentoxy group, methoxy group, ethoxy group, propoxy group, butoxy group, pentoxy group, hexyloxy group, heptyloxy group, vinyl group, 1-propenyl group, 2-propenyl group, 1-butenyl group, 2-butenyl group, 3-butenyl group, 1-pentenyl group, 2-pentenyl group, 3-pentenyl group, 4-pentenyl group, 1-hexenyl group, 2-hexenyl group, 3-hexenyl group, 4-hexenyl group, 5-hexenyl group, 1-heptenyl group, 2-heptenyl group, 3-heptenyl group, 4-heptenyl group, 5-heptenyl group, 6-heptenyl group, ethynyl group, 1-propynyl group, 2-propynyl group, 1-butynyl group, 2-butynyl group, 3-butynyl group, 1-pentynyl group, 2-pentynyl group, 3-pentynyl group, 4-pentynyl group, 1-hexynyl group, 2-hexynyl group, 3-hexynyl group, 4-hexynyl group, 5-hexynyl group, 1-heptynyl group, 2-heptynyl group, 3-heptynyl group, 4-heptynyl group, 5-heptynyl group, 6-heptynyl group, and 1,5-hexadienyl.

At least one hydrogen atom of $H_1$ to $H_{12}$ on benzene rings is replaced by a halogen atom. When hydrogen atom of either $H_6$ or $H_8$ is replaced by a halogen atom, at least one hydrogen atom of remaining $H_1$ to $H_{12}$ is replaced by a halogen atom. While the halogen atom includes fluorine atom, chlorine atom, bromine atom, and iodine atom, when viscosity of liquid crystal compositions is taken into consideration, the halogen atom to be used is preferably fluorine atom or chlorine atom, and more desirably fluorine atom.

While at least one hydrogen atom of $H_1$ to $H_{12}$ is replaced by a halogen atom, number of the halogen atom to be used for the substitution is preferably 1 to 4, and when the viscosity is taken into consideration, the number of halogen atom is more preferably 1 or 2.

Tetracyclic compounds expressed by the general formula (1) and one or more atoms of which compounds are replaced by isotopes are included in the scope of the present invention. In other words, whereas hydrogen atoms of the compounds expressed by the general formula (1) usually have a mass number of 1, the hydrogen atoms at specific positions may be replaced by deuteriums.

Tetracyclic compounds of the present invention expressed by the general formula (1) have a wide temperature range of a nematic phase, high chemical stability, high miscibility with other liquid crystalline compounds, and high optical anisotropy, and thus the compounds are extremely important as a constituent of liquid crystal compositions.

Tetracyclic compounds expressed by the general formula (1) have a remarkably wide temperature range of a nematic phase compared with conventional liquid crystalline compounds. Particularly, the melting point (C-N point) or S-N point of the compounds of the general formula (1) is extremely low compared with that of conventional compounds, and the temperature range of a namatic phase of the inventive compounds is considerably wide compared with that of known liquid crystalline compounds.

Any tetracyclic compounds of the general formula (1) have a high miscibility with other liquid crystalline compounds or liquid crystal compositions, and liquid crystal compositions comprising one of the tetracyclic compounds do not lose the namatic phase even at low temperatures (for example, −20° C. which is required from practical use).

Any tetracyclic compounds of the general formula (1) are highly stable chemically, and the liquid crystal compositions comprising the tetracyclic compound have a very high specific resistance and voltage holding ratio. Also, the compounds have an extremely high stability against UV and heat.

Any tetracyclic compounds of the general formula (1) exhibit a low viscosity, and do not remarkably raise viscosity of whole liquid crystal compositions even when used in a large amount. Further, dependency of its viscotheiry on temperature, particularly the dependency on temperature at low temperatures is extremely small.

As described above, since the tetracyclic compounds of the present invention have excellent properties, they can preferably be used for TFT for the first and for other applications. For instance, the tetracyclic compounds are preferable as liquid crystalline compounds for liquid crystal display devices of TN mode, STN mode, guest-host mode, or dynamic scattering mode, or for polymer dispersed liquid crystal display devices.

Liquid crystal compositions of the present invention preferably contain at least one tetracyclic compound expressed by the general formula (1) in the ratio of 0.1 to 99% by weight to exhibit excellent properties.

More specifically, liquid crystal compositions provided by the present invention contain at least one compound optionally selected, depending on the purpose of the liquid crystal compositions, from the group consisting of the compounds expressed by any one of the general formulas (2) to (9) in addition to a first component comprising at least one tetracyclic compound expressed by the general formula (1), to achieve the objects of the present invention.

As compounds used in the present invention and expressed any one of the general formulas (2) to (4), the following compounds can preferably be mentioned:

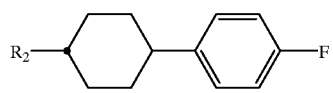
(2-1)

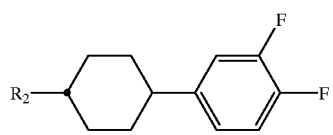
(2-2)

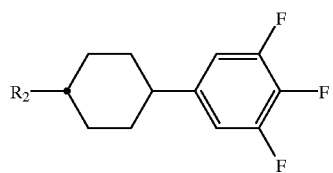
(2-3)

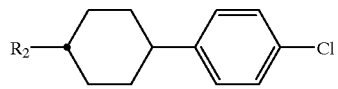
(2-4)

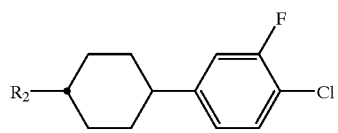
(2-5)

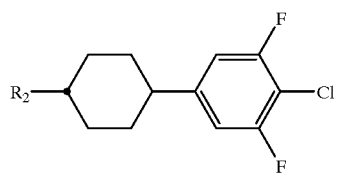
(2-6)

-continued

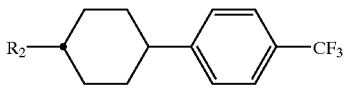
(2-7)

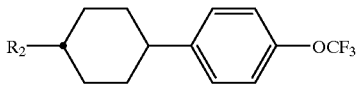
(2-8)

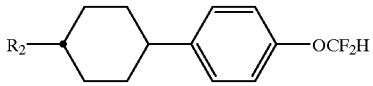
(2-9)

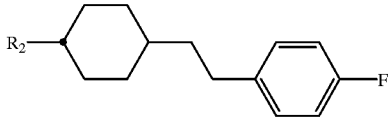
(2-10)

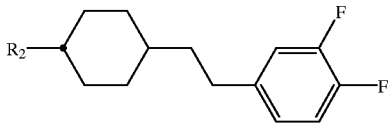
(2-11)

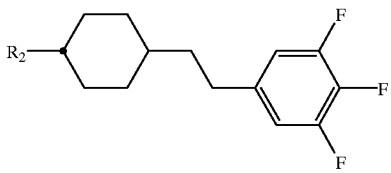
(2-12)

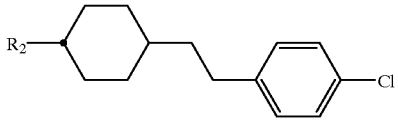
(2-13)

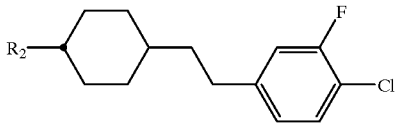
(2-14)

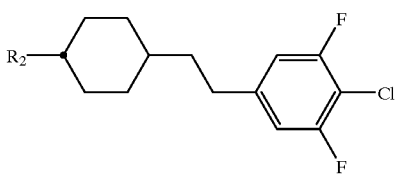
(2-15)

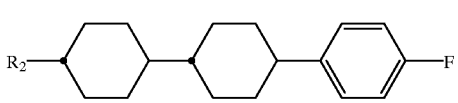
(3-1)

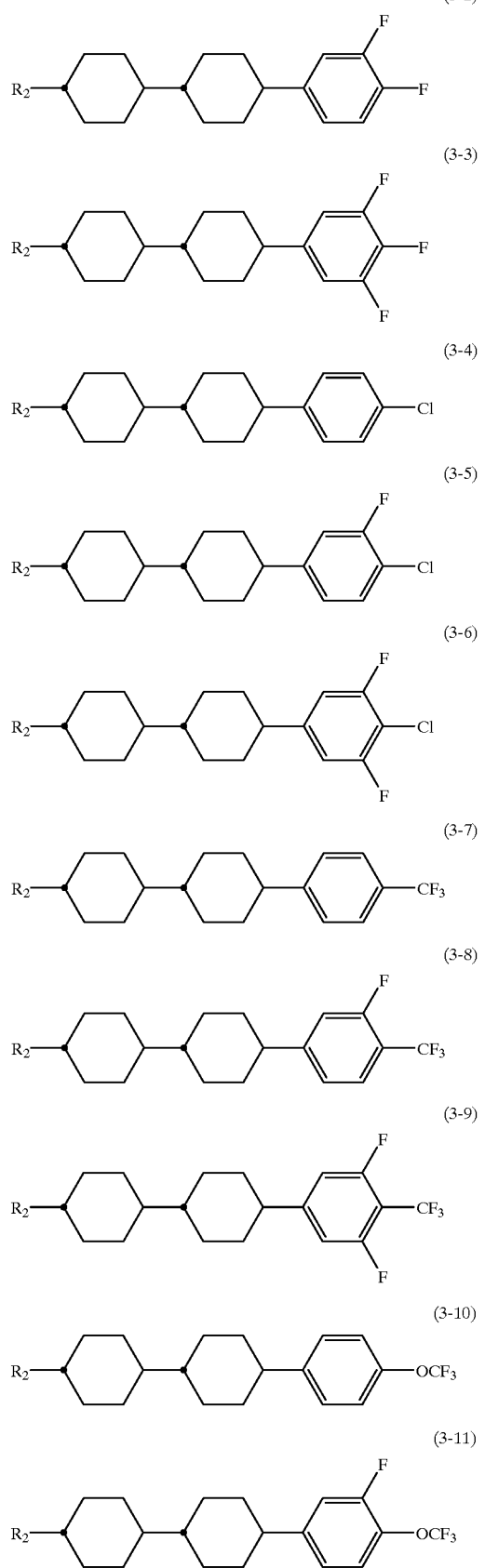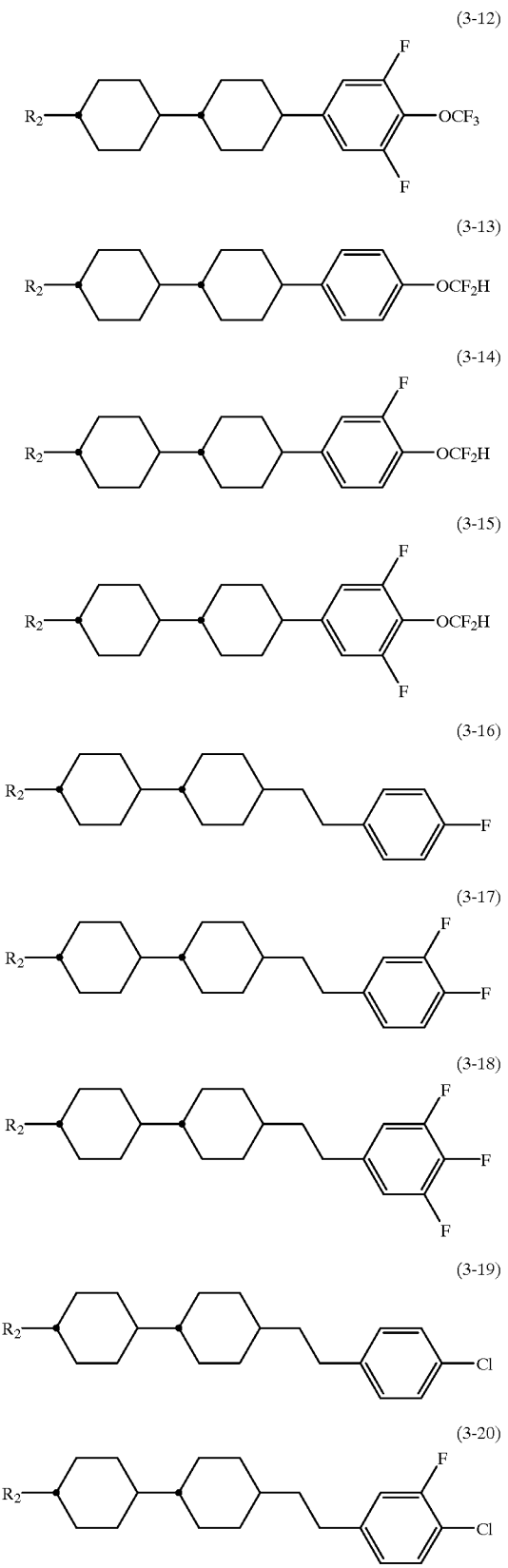

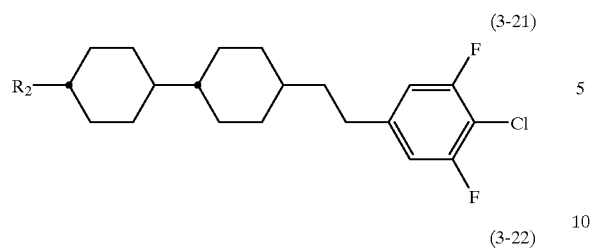
(3-21)
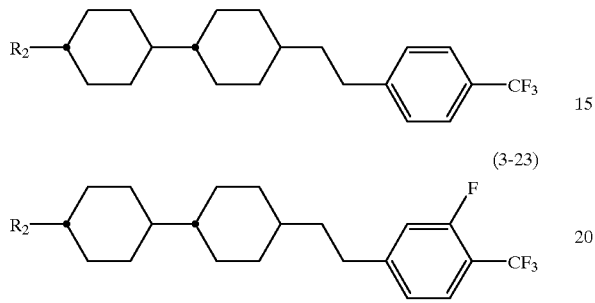
(3-22)
(3-23)
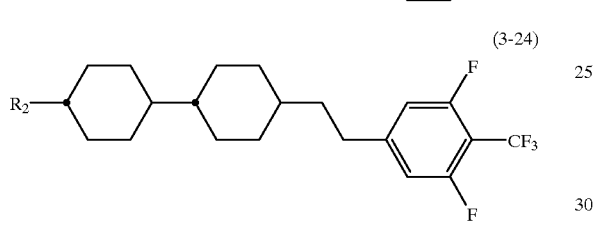
(3-24)
(3-25)
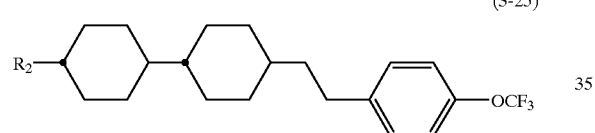
(3-26)
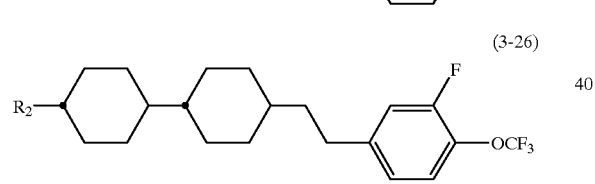
(3-27)
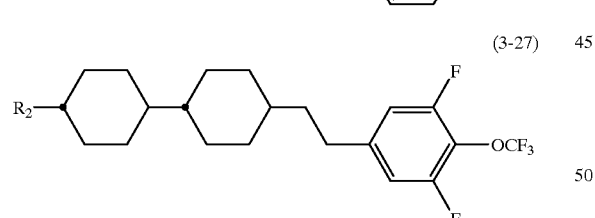
(3-28)
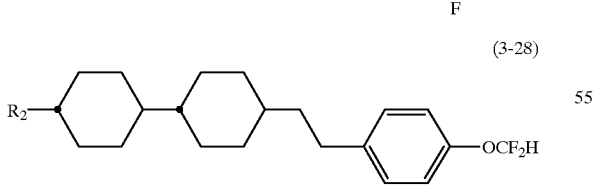
(3-29)
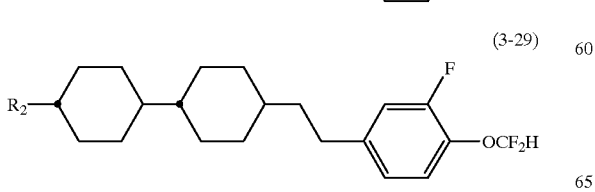
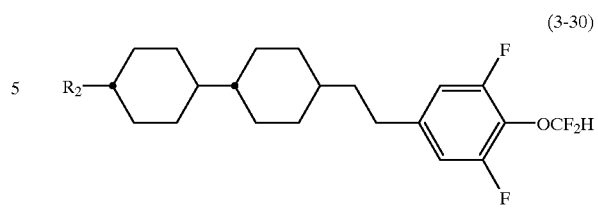
(3-30)
(3-31)
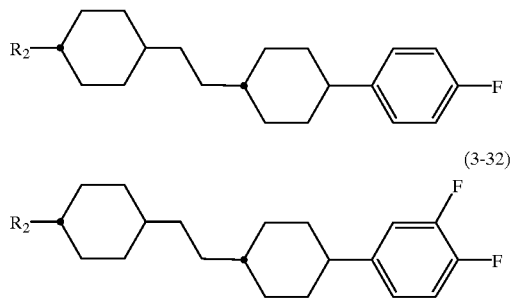
(3-32)
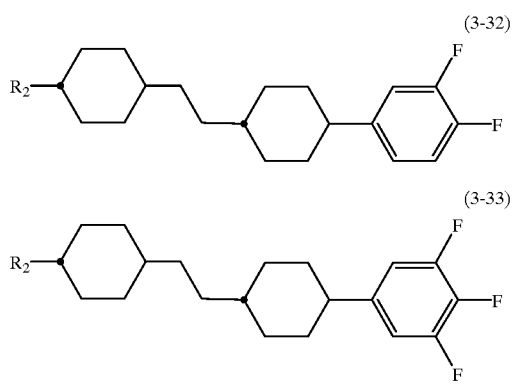
(3-33)
(3-34)
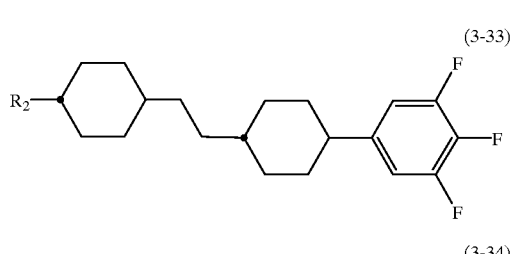
(3-35)
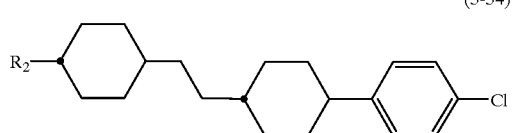
(3-36)
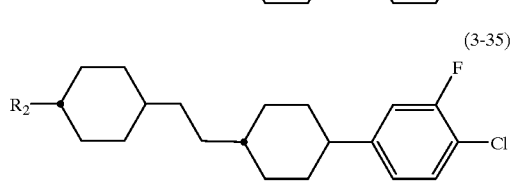
(3-37)
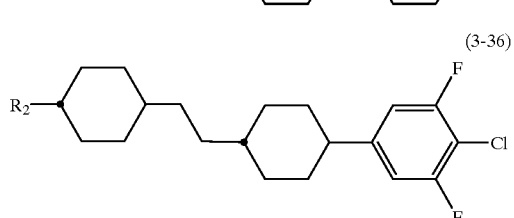
(3-38)
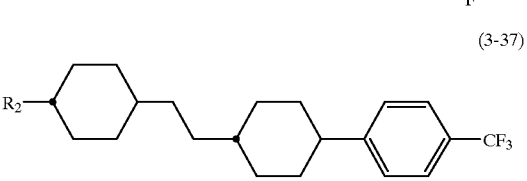
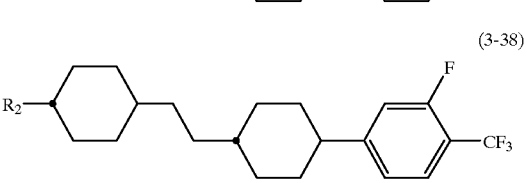

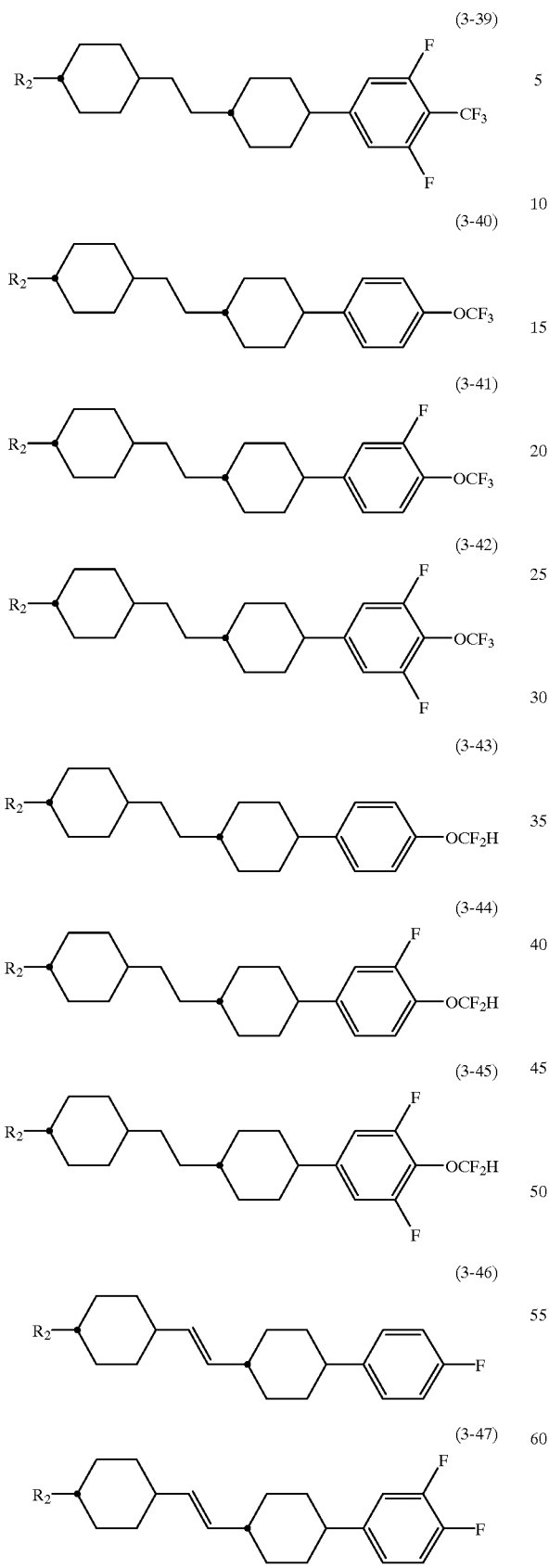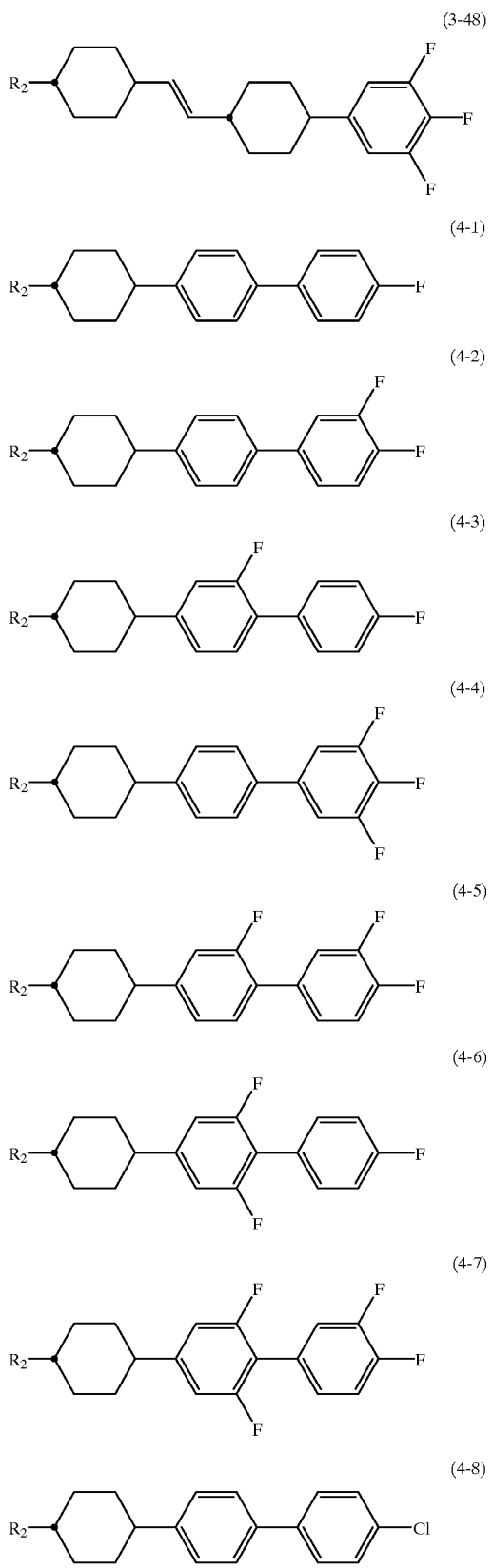

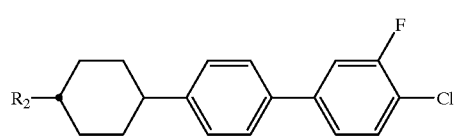
(4-9)
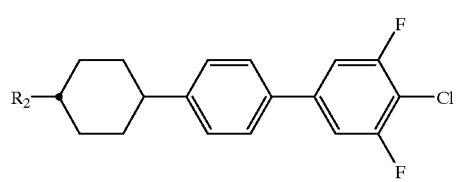
(4-10)
(4-11)
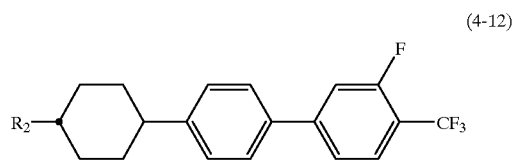
(4-12)
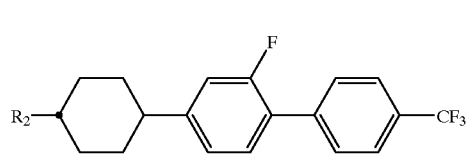
(4-13)
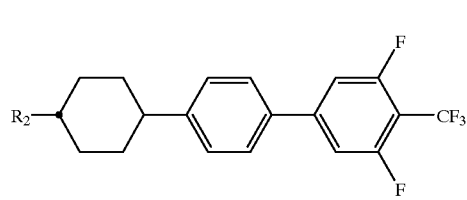
(4-14)
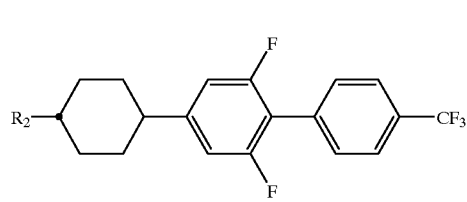
(4-15)
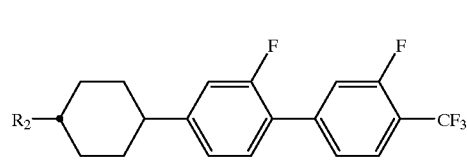
(4-16)
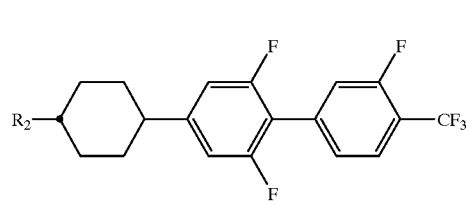
(4-17)
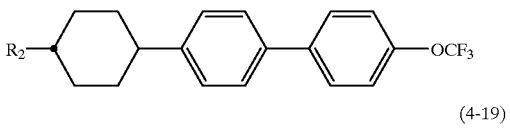
(4-18)
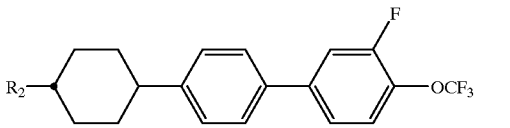
(4-19)
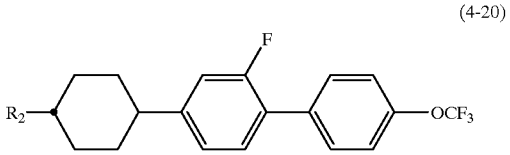
(4-20)
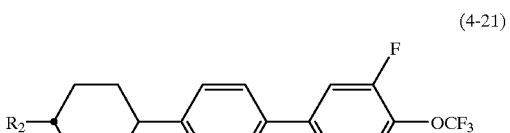
(4-21)
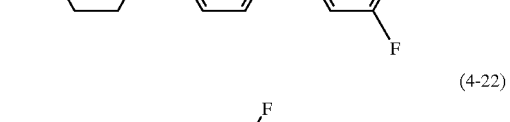
(4-22)
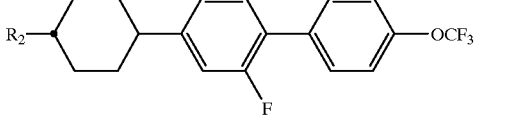
(4-23)
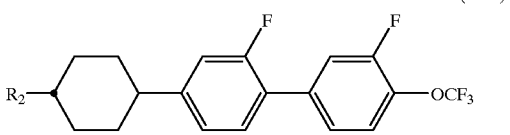
(4-24)
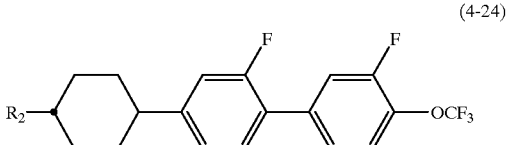
(4-25)
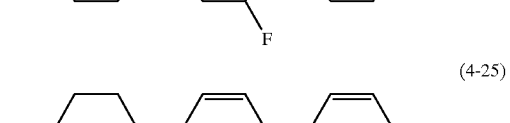
(4-26)
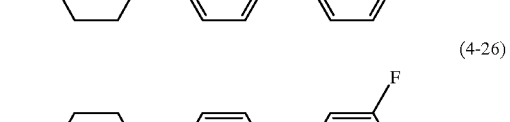
(4-27)
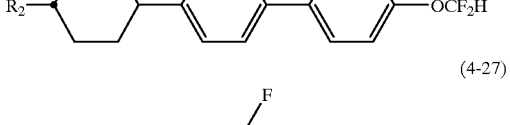

(4-28)
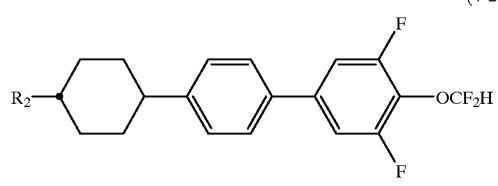
(4-29)
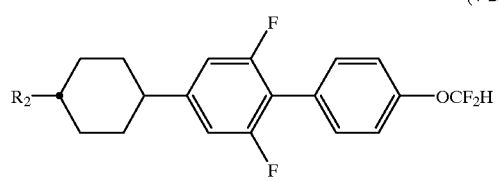
(4-30)
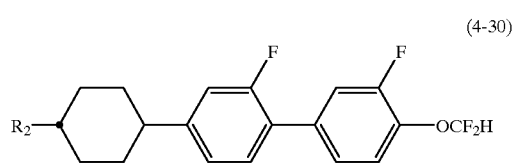
(4-31)
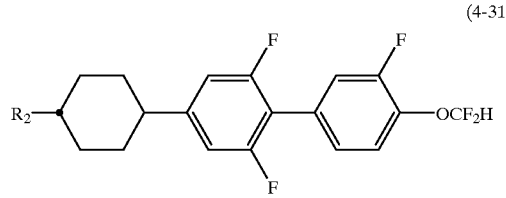
(4-32)
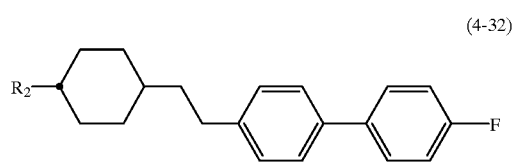
(4-33)
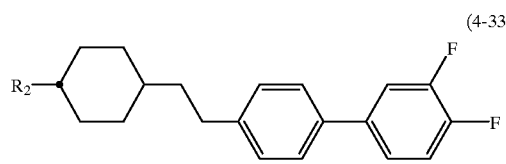
(4-34)
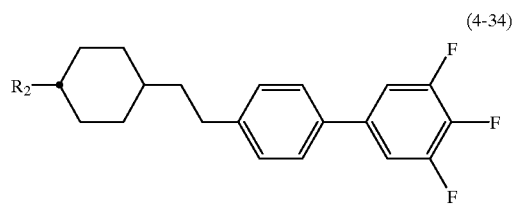
(4-35)
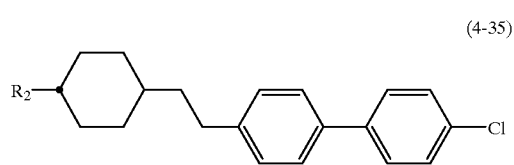
(4-36)
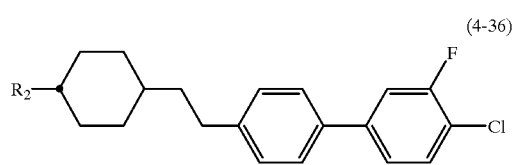
(4-37)
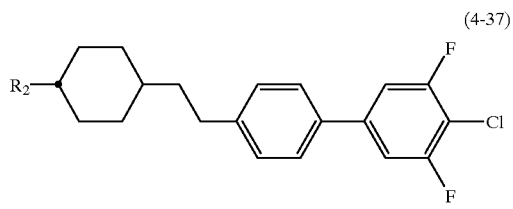
(4-38)
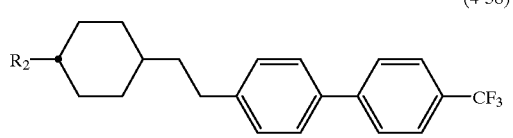
(4-39)
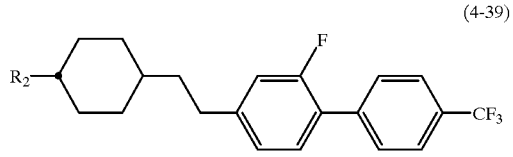
(4-40)
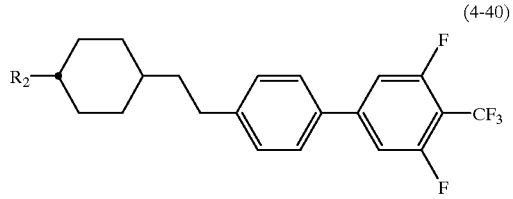
(4-41)
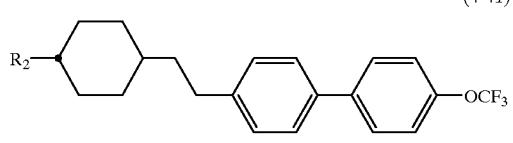
(4-42)
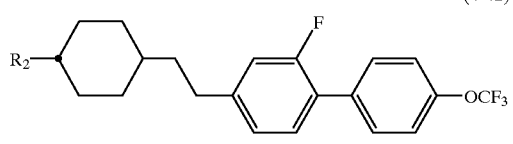
(4-43)
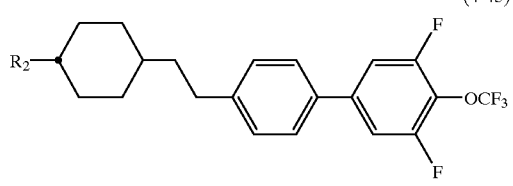
(4-44)
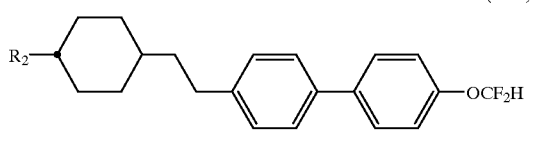
(4-45)
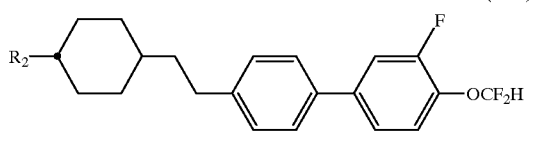

-continued (4-46)
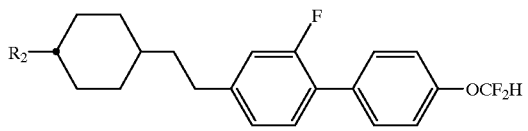

(4-47)
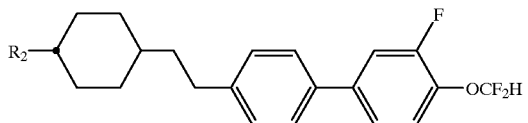

(4-48)

(4-49)

(4-50)

(4-51)

(4-52)

(4-53)

wherein $R_2$ has the same meaning as described above.

Compounds expressed by any one of the general formulas (2) to (4) have a positive dielectric anisotropy, are very excellent in heat stability and chemical stability, and thus are extremely useful when liquid crystal compositions are prepared for TFT (AM-LCD) of which high reliability such as a particularly high voltage holding ratio or high specific resistance is required.

When liquid crystal compositions for TFT are prepared, the amount of the compounds expressed by any one of the general formulas (2) to (4) to be used is usually 1 to 99% by weight, preferably 10 to 97% by weight, and more desirably 40 to 95% by weight based on the total amount of the liquid crystal composition. At that time, the liquid crystal compositions may contain the compounds expressed by any one of the general formulas (5) to (9) as a part of the compositions. Even when liquid crystal compositions for STN display mode or ordinary TN display mode are prepared, the compounds expressed by any one of the general formulas (2) to (4) may be used.

As compounds of the present invention expressed by any one of the general formulas (5) to (7), the following compounds can preferably be mentioned:

(5-1)

(5-2)
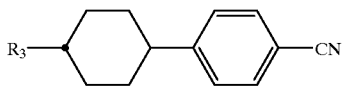

(5-3)
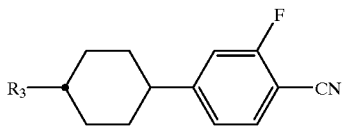

(5-4)
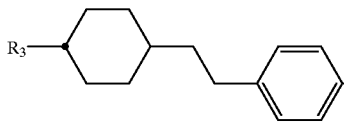

(5-5)
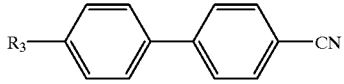

(5-6)
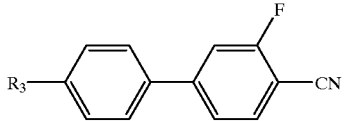

(5-7)
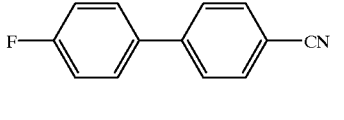

(5-8)
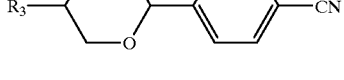

(5-9)
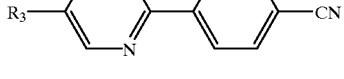

(5-10)
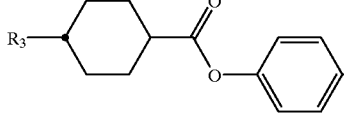

-continued
(5-11)
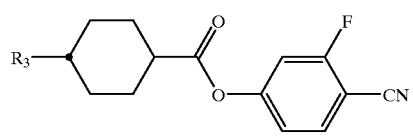
(5-12)
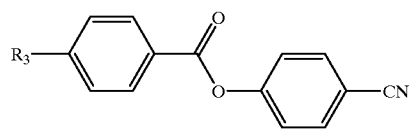
(5-13)
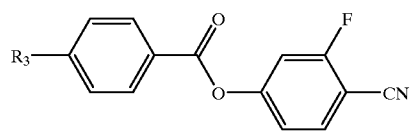
(5-14)
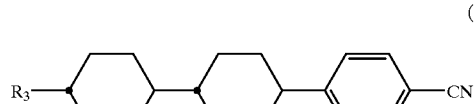
(5-15)
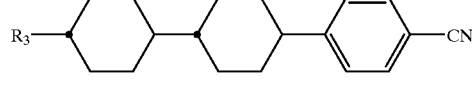
(5-16)
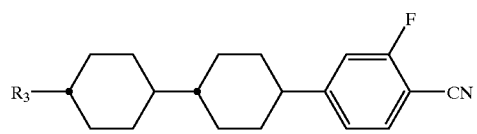
(5-17)
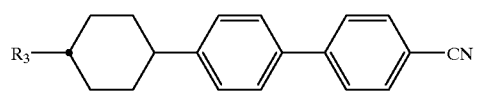
(5-18)
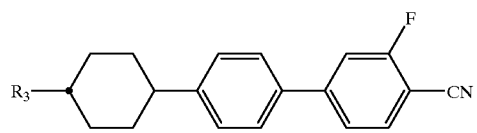
(5-19)
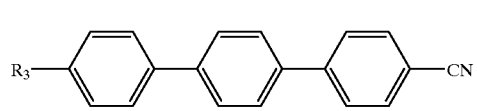
(5-20)
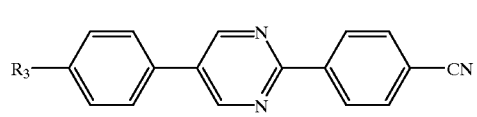
-continued
(5-21)
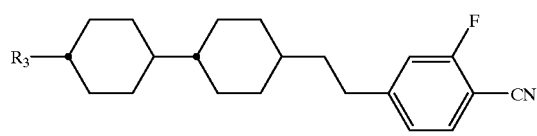
(5-22)
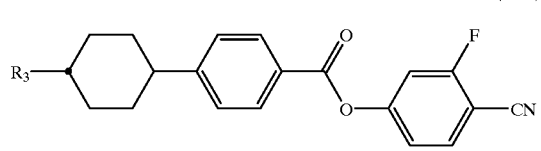
(5-23)
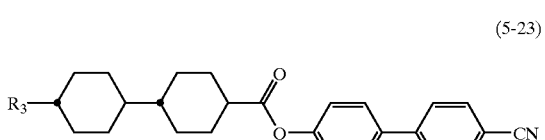
(5-24)
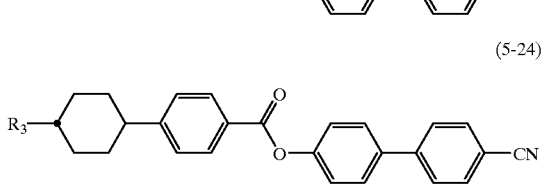
(6-1)
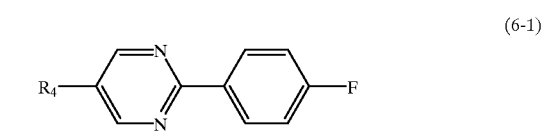
(6-2)
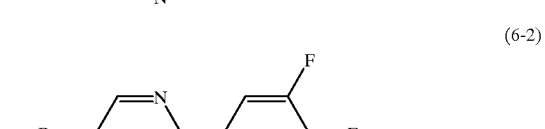
(6-3)
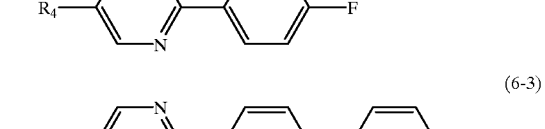
(7-1)
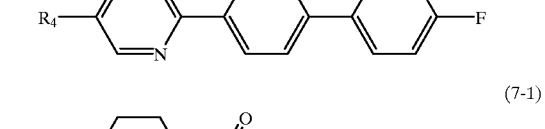
(7-2)
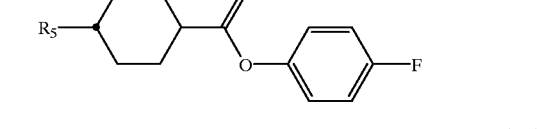
(7-3)
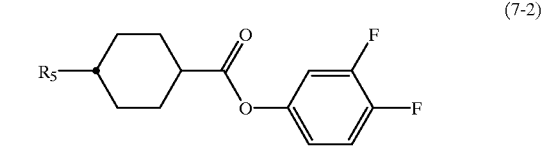

wherein $R_3$ to $R_5$ have the same meaning as described above.

Compounds expressed by any one of the general formulas (5) to (7) have a high positive dielectric anisotropy and thus are used for the purpose of lowering threshold voltage. Also, the compounds can be used for the purposes of adjusting viscosity, adjusting optical anisotropy, and widening a nematic range such as raising clearing point. Further, they can be used even for the purpose of improving steepness.

As compounds of the present invention expressed by the general formula (8) or (9), the following compounds can preferably mentioned:

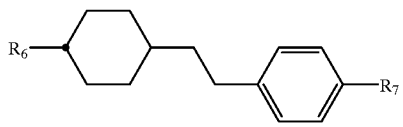 (8-4)

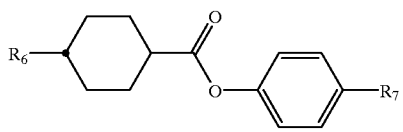 (8-5)

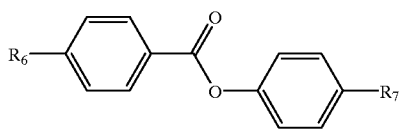 (8-6)

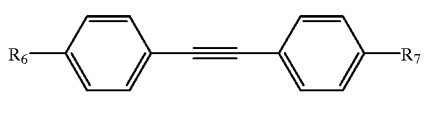 (8-7)

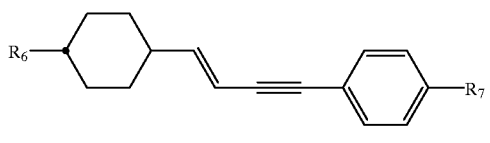 (8-8)

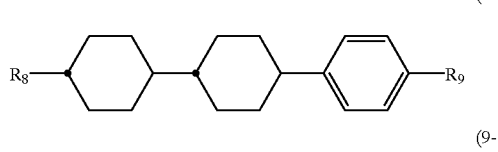 (9-1)

 (9-2)

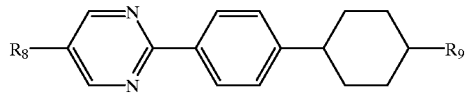 (9-3)

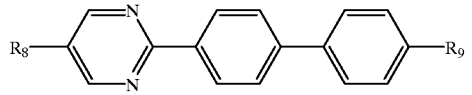 (9-4)

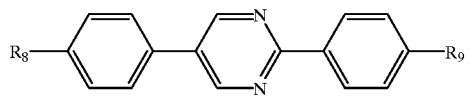 (9-5)

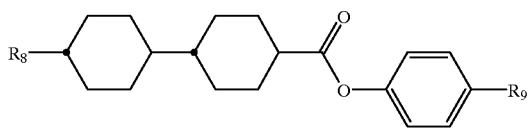 (9-6)

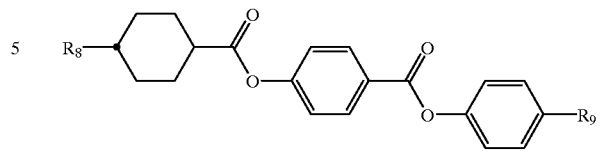 (9-7)

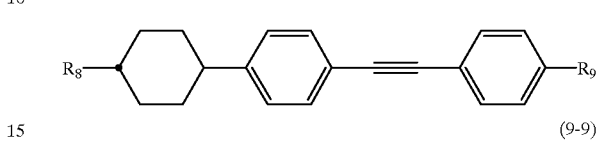 (9-8)

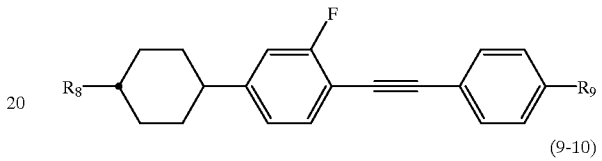 (9-9)

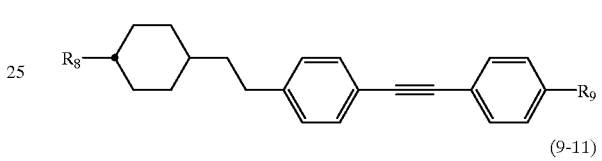 (9-10)

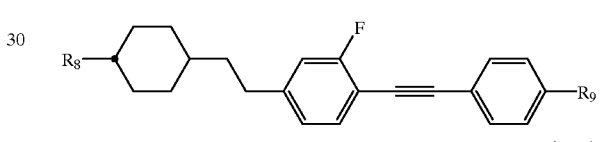 (9-11)

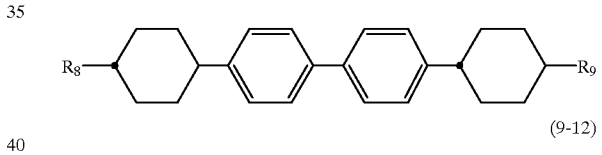 (9-11)

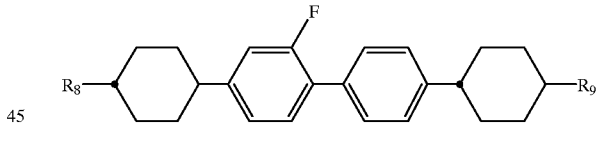 (9-12)

wherein $R_6$ to $R_9$ have the same meaning as described above.

Compounds expressed by the general formula (8) or (9) have a negative or a small positive dielectric anisotropy. Compounds expressed by the general formula (8) are used for the purpose of mainly reducing viscosity and/or adjusting optical anisotropy. Compounds expressed by the general formula (9) are used for the purpose of widening a nematic range such as raising clearing point and adjusting optical anisotropy.

Compounds expressed by any one of the general formulas (5) to (9) are extremely useful particularly when liquid crystal compositions for STN display mode or ordinary TN display mode are prepared.

While the compounds expressed by any one of the general An formulas (5) to (9) can optionally be used in the range of 1 to 99% by weight based on the total amount of liquid crystal composition when liquid crystal compositions for ordinary TN display mode or STN display mode are prepared, the amount is preferably 10 to 97% by weight, and more desirably 40 to 95% by weight. Further, the compounds expressed by any one of the general formulas (2) to (4) may partly be used at that time.

Liquid crystal compositions of the present invention are produced by conventional methods. Generally, a method is adopted in which various components are dissolved in each other at a high temperature. However, a method can be used in which liquid crystalline compounds are dissolved in an organic solvent, mixed therein, and then the organic solvent is distilled off.

Liquid crystal compositions of the present invention may be improved depending on intended uses by adding suitable additives and may be optimized. Such additives are well known in the art and described in the literature. Usually, a chiral dopant or likes are added to induce a helical structure of liquid crystals to adjust a required twisting angle, and to avoid reverse-twist.

Further, the liquid crystal compositions of the present invention can be used as compositions for guest-host (GH) mode by adding a dichroic dye such as merocyanine type, styryl type, azo type, azomethine type, azoxy type, quinophthalone type, anthraquinone type, or tetrazine type. Alternatively, they can also be used as liquid crystal compositions for polymer dispersed liquid crystal display devices (PDLCD) represented by NCAP which is prepared by the microencapsulation of a nematic liquid crystal or represented by polymer net work liquid crystal display device (PNLCD)s which are prepared by forming a polymer of three-dimensional reticulated structure in a liquid crystal. Also, the liquid crystal compositions of the present invention can be used as ones for an electrically controlled birefringence (ECB) mode or a dynamic scattering (DS) mode.

Tetracyclic compounds of the present invention expressed by the general formula (1) can be produced by freely using ordinary procedures in organic synthetic chemistry. That is, the tetracyclic compounds can be produced by using, in combination, known reactions described in reference books such as "Shin-Jikken Kagaku Kouza (Course of New Chemical Experiment)", Organic Synthesis, and Organic Reactions, and journals.

For instance, those compounds can be produced, without difficulties, according to typical examples shown below. In the followings, $R_1$, $Y_1$, $X_1$, $X_2$, $X_3$, and $H_1$ to $H_{12}$ have the same meaning as described above, $G_1$ represents bromine atom or iodine atom, and g and p is a natural number of 0, 1 or more.

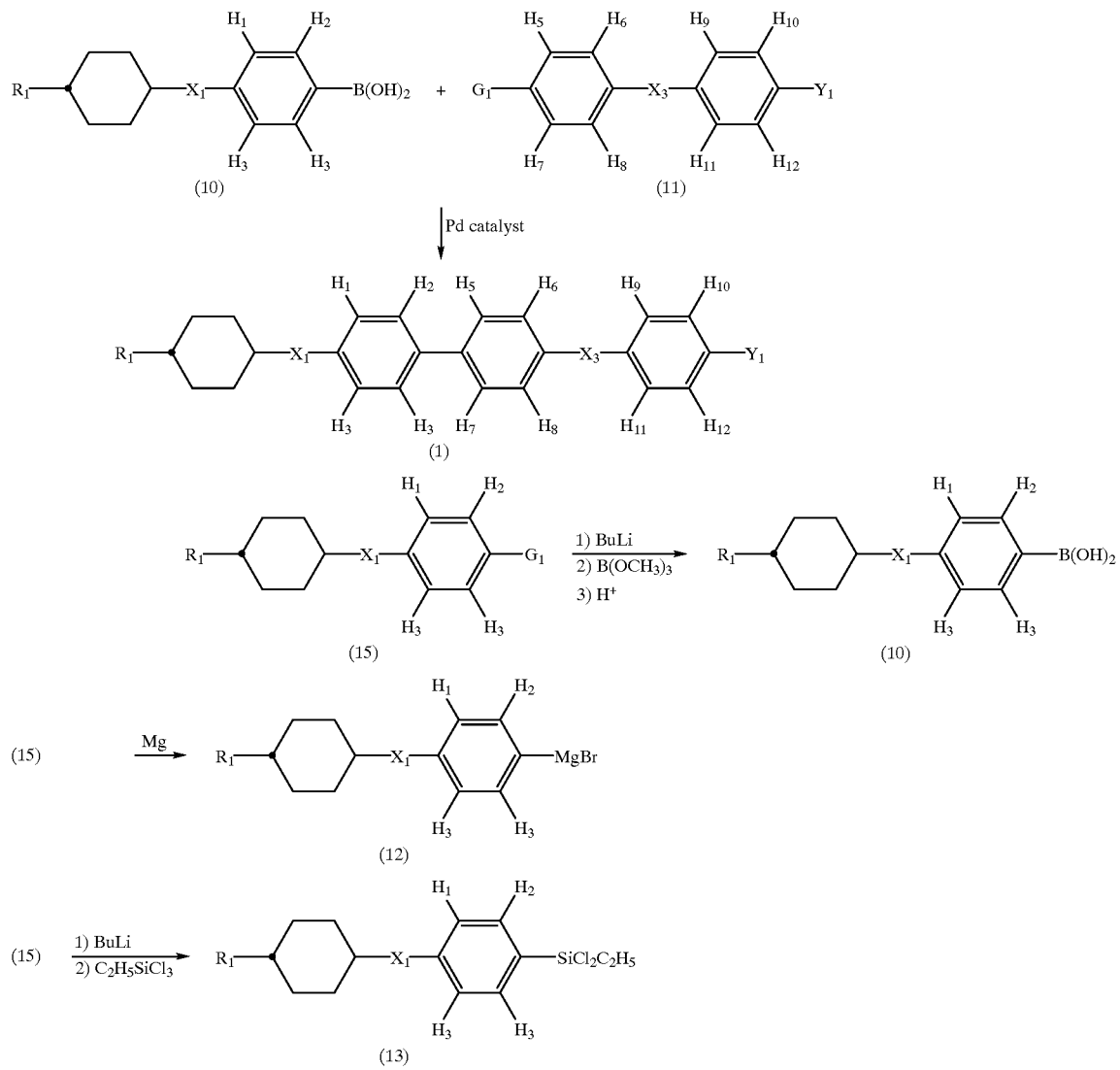

-continued
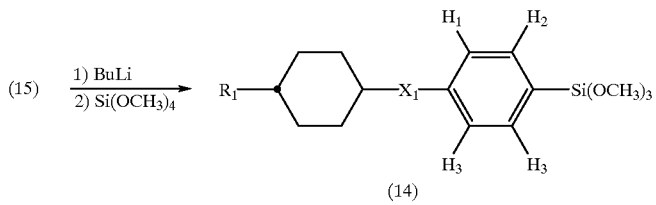
(14)
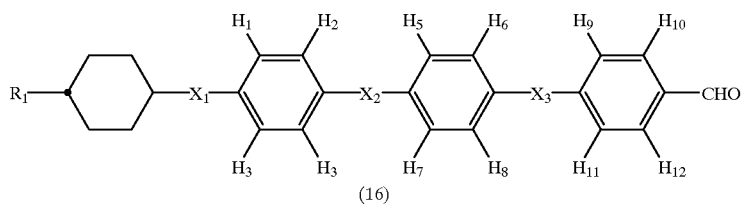
(16)
↓ Two carbons homologation reaction
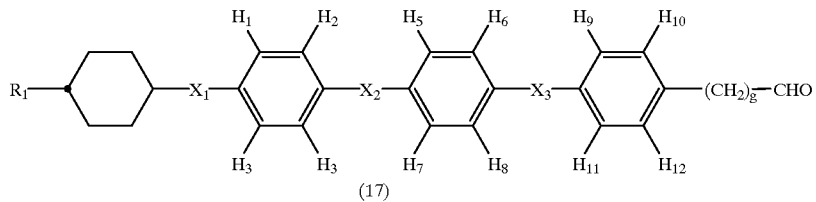
(17)
↓ Wittig reaction
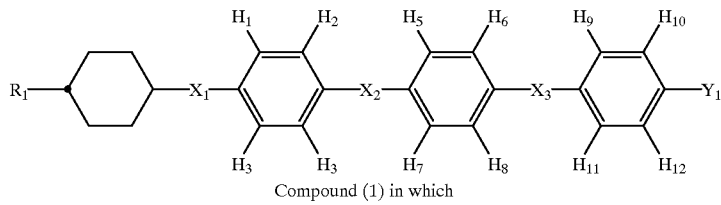
Compound (1) in which $Y_1$ is an alkenyl group
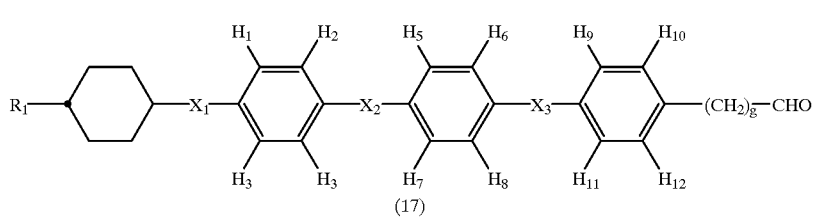
(17)
↓ Reaction for forming an alkyne
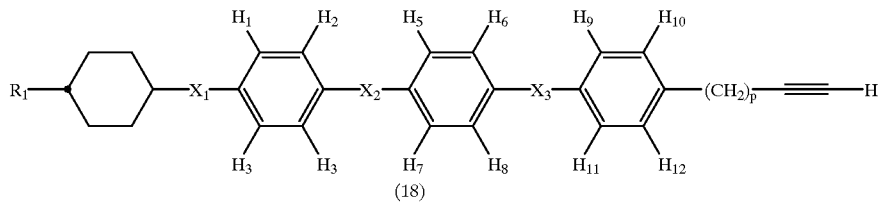
(18)
↓ Alkylation reaction -continued

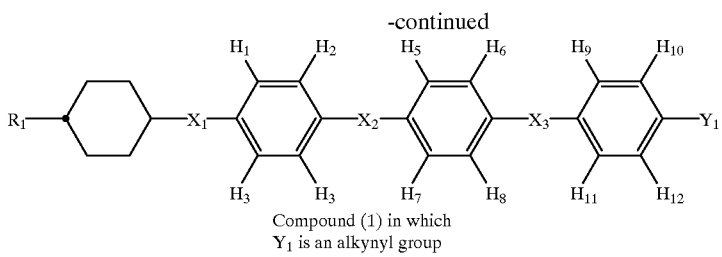

Compound (1) in which
$Y_1$ is an alkynyl group

That is, the tetracyclic compounds expressed by the general formula (1) can be produced as a cross-coupling adduct by subjecting a derivative of boric acid (10) and a halide (11) to a cross-coupling reaction in the presence of a catalyst such as palladium or nickel according to the method of Suzuki et al. (Synth. Commun., 11, 513 (1981)).

Also, the tetracyclic compounds expressed by the general formula (1) can be produced by carrying out a cross-coupling reaction by using, in stead of the derivative of boric acid (10), a Grignard reagent (12) according to an ordinary method, using a silicon compound (13) according to the method of Hatakenaka et al. (Tetrahedron, 50, 8301, (1994)), or using a silicon compound (14) according to the method disclosed in Laid-open Japanese Patent Publication No. Hei 7-141,117.

Compounds (10), (12), (13), and (14) can be produced by subjecting a compound of the formula (15), which can be produced according to the method described in Laid-open Japanese Patent Publication No. Sho 60-97,925, Japanese Patent Publication No. Sho 59-35,901 and others, to an appropriate reaction under the conditions described in the literature mentioned above. That is, the compound (10) can be obtained by reacting the halide (15) with alkyl lithium and trialkyl borate successively, and then treating with an acid. Compound (12) can be obtained by reacting a halide (15) with magnesium. Compound (13) can be obtained by treating the halide (15) with alkyl lithium and then reacting with alkyltrichlorosilane. Compound (14) can be obtained by treating the halide (15) with alkyl lithium and then reacting with tetraalkoxysilane.

When $Y_1$ is an alkenyl group or alkynyl group, it is preferable to introduce $Y_1$ by the following production method. That is, the compound (1) in which $Y_1$ is an alkenyl group can be produced by subjecting a compound of the formula (16), which is produced according to the method described in Japanese Patent Publication No. Hei 7-2,653, to a two carbons homologation reaction and the Wittig reaction. Compound (1) in which $Y_1$ is an alkynyl group can be produced by converting a compound of the formula (17) into an acetylene derivative (18) according to an ordinary method and then alkylating the derivative (18).

Now, the methods for producing the compounds of the present invention and use examples thereof will be described in more detail with reference to Examples. In the Examples, C indicates crystals, N does a nematic phase, S does a smectic phase, and I indicates isotropic liquid, and the unit of all phase transition temperatures is ° C.

EXAMPLE 1

Preparation of 4-(4-methoxymethylcyclohexyl)-2'-fluoro-4"-methylterphenyl (Compound expressed by general formula (1) wherein $R_1$ represents methoxymethyl group, $X_1$, $X_2$, and $X_3$ represent a covalent bond, $Y_1$ represents methyl group, $H_1$ to $H_4$, and $H_6$ to $H_{12}$ represent hydrogen atom, and $H_5$ represents fluorine atom; Compound No. a-1)

To a mixture of 4-bromotoluene (743 mmol) and 500 ml of tetrahydrofuran (THF) was added dropwise 500 ml of a solution of n-butyl lithium (corresponding to 780 mmol) in hexane at −78° C. in 1.6 hours, and stirred at the same temperature for 1.5 hours. To this solution was added dropwise 200 ml of a solution of triisopropyl borate (1,486 mmol) in THF, the solution was gradually warmed up to room temperature, and then the solution was stirred overnight. After 750 ml of 7.3% hydrochloric acid was added and stirred for 30 min, the reaction solution was extracted twice with diethyl ether, washed thrice with water, and then dried over anhydrous magnesium sulfate. The solvent was distilled off and the residue was recrystallized from about 1,000 ml of toluene to give a white solid of 4-methylphenyl boric acid (545 mmol).

Mixture of 4-methylphenyl boric acid (73.6 mmol), 1-bromo-3-fluorobenzene (66.2 mmol), potassium carbonate (147 mmol), 0.5 g of 5% palladium carbon, 100 ml of toluene, 100 ml of ethanol, and 6.0 ml of water was refluxed for 5 hours. After allowed to cool, the reaction solution was filtered and dried over anhydrous magnesium sulfate.

The solvent was distilled off and the residue was purified by column chromatography (eluent: toluene/n-heptane=1/9) and recrystallization (solvent for recrystallization: ethanol) to give a colorless 3-fluoro-4'-methylbiphenyl (13.6 mmol).

To a mixture of 4-(4-methoxymethylcyclohexyl)-1-iodobenzene (297 mmol) and 250 ml of THF, was added dropwise 200 ml of a solution of n-butyl lithium (corresponding to 312 mmol) in hexane at −78° C. in 3.0 hours, and stirred at the same temperature for 1.2 hours. To the solution was added dropwise 100 ml of a solution of triisopropyl borate (594 mmol) in THF, the solution was gradually warmed up to room temperature, and then the solution was stirred overnight. After 270 ml of 7.3% hydrochloric acid was added and stirred for 30 min, the reaction solution was extracted twice with diethyl ether, washed thrice with water, and dried over anhydrous magnesium sulfate. The solvent was distilled off and the residue was washed with heptane to give a white solid of 4-(4-methoxymethylcyclohexyl) phenyl boric acid (60.1 mmol).

Mixture of 3-fluoro-4'-methylbiphenyl (13.4 mmol), iodic acid (6.71 mmol), iodine (8.08 mmol), acetic acid (10 ml), water (1.2 ml), and carbon tetrachloride (1.2 ml) was refluxed for 24 hours. After allowed to cool, the reaction solution was extracted twice with heptane and washed twice with water. The solution was washed with 50 ml of 4% aqueous solution of sodium thiosulfate, washed thrice with water, and then dried over anhydrous magnesium sulfate.

The solvent was distilled off and the residue was purified by column chromatography (eluent: toluene/n-heptane=1/9) and recrystallizations (solvent for recrystallization: ethanol) repeated twice to give a pale yellow-green crystal of 3-fluoro-4-iodo-4'-methylbiphenyl (3.39 mmol).

Mixture of 4-(4-methoxymethylcyclohexyl)phenyl boric acid (8.42 mmol), 3-fluoro-4-iodo-4'-methylbiphenyl (3.36 mmol), potassium carbonate (16.8 mmol), 0.1 g of 5% palladium carbon, 14 ml of toluene, 14 ml of ethanol, and 0.7 ml of water was refluxed for 6 hours. After allowed to cool, the reaction solution was filtered and dried over anhydrous magnesium sulfate.

The solvent was distilled off and the residue was purified by column chromatography (eluent: toluene) and recrystallization (solvent for recrystallization: ethanol/toluene=4/3) to give a colorless crystal of the subject compound (2.58 mmol). Various spectral data of the compound well supported its structure as follows:

1H-NMR: δ (ppm): 7.21–7.59 (m, 11H), 3.36 (s, 3H), 3.26 (d, 2H), 2.37–2.49 (brs, 1H), 2.41 (s, 3H), 1.07–2.10 (m, 9H)

GC-MS: 388 (M+)

Further, the subject compound exhibited liquid crystallinity and its phase transition temperatures were as follows:

C-N point: 156.4° C., N-I point: 315.7° C.

EXAMPLE 2

Preparation of 4-(4-methoxymethylcyclohexyl)-2'5'-difluoro-4"-methylterphenyl (Compound expressed by general formula (1) wherein $R_1$ represents methoxymethyl group, $X_1$, $X_2$, and $X_3$ represent a covalent bond, $Y_1$ represents methyl group, $H_1$ to $H_4$, $H_6$, $H_7$, and $H_9$ to $H_{12}$ represent hydrogen atom, and $H_5$ and $H_8$ represent fluorine atom; Compound No. b-1)

To a mixture of 4-bromotoluene (743 mmol) and 500 ml of THF was added dropwise 500 ml of a solution of n-butyl lithium (corresponding to 780 mmol) in hexane at −78° C. in 1.6 hours, and stirred at the same temperature for 1.5 hours. To this solution was added dropwise 200 ml of a solution of triisopropyl borate (1,486 mmol) in THF, the solution was gradually warmed up to room temperature, and then the solution was stirred overnight. After 750 ml of 7.3% hydrochloric acid was added and stirred for 30 min, the reaction solution was extracted twice with diethyl ether, washed thrice with water, and then dried over anhydrous magnesium sulfate. The solvent was distilled off and the residue was recrystallized from about 1,000 ml of toluene to give a white solid of 4-methylphenyl boric acid (545 mmol).

Mixture of 4-methylphenyl boric acid (46.0 mmol), 1.4-dibromo-2,5-difluorobenzene (91.9 mmol), potassium carbonate (92.0 mmol), 1.0 g of 5% palladium carbon, 120 ml of toluene, 120 ml of ethanol, and 6.0 ml of water was refluxed for 6 hours. After allowed to cool, the reaction solution was filtered and dried over anhydrous magnesium sulfate.

The solvent was distilled off and the residue was purified by column chromatography (eluent: n-heptene) and recrystallization (solvent for recrystallization: ethanol) to give a colorless needle of 4-bromo-2,5-difluoro-4'-methylbiphenyl (16.0 mmol).

To a mixture of 4-bromo-2,5-difluoro-4'-methylbiphenyl (7.06 mmol) and 20 ml of THF, was added dropwise 5.0 ml of a solution of n-butyl lithium (corresponding to 7.85 mmol) in hexane at −78° C. in 10 min, and stirred at the same temperature for 3.2 hours. To this solution was added dropwise 10 ml of a solution of triisopropyl borate (15.2 mmol) in THF, the solution was gradually warmed up to room temperature, and then the solution was stirred overnight. After 9 ml of 7.3% hydrochloric acid was added and stirred for 30 min, the reaction solution was extracted twice with toluene, washed thrice with water, and then dried over anhydrous magnesium sulfate. The solvent was distilled off and the residue was recrystallized from about 10 ml of toluene to give a white solid of 2,5-difluoro-4'-methylbiphenyl-4-boric acid (5.48 mmol).

Mixture of 2,5-difluoro-4'-methylbiphenyl-4-boric acid (5.24 mmol), 4-(4-methoxymethylcyclohexyl)-1-iodobenzene (5.24 mmol), potassium carbonate (10.5 mmol), 0.1 g of 5% palladium carbon, 12 ml of toluene, 12 ml of ethanol, and 0.6 ml of water was refluxed for 7 hours. After allowed to cool, the reaction solution was filtered and dried over anhydrous magnesium sulfate.

The solvent was distilled off and the residue was purified by column chromatography (eluent: toluene/n-heptane=1/1) and recrystallization (solvent for recrystallization: ethanol/toluene=2/1) to give a colorless crystal of the subject compound (3.99 mmol). Various spectral data of the compound well supported its structure as follows:

1H-NMR: δ (ppm): 7.11–7.52 (m, 10H), 3.35 (s, 3H), 3.25 (d, 2H), 2.01–2.54 (brs, 1H), 2.40 (s, 3H), 1.06–1.90 (m, 9H)

GC-MS: 406 (M+)

Further, the subject compound exhibited liquid crystallinity and its phase transition temperatures were as follows:

C-N point: 120.4° C., N-I point: 276.3° C.

EXAMPLE 3

Preparation of 4-(4-propylcyclohexyl)-3-fluoro-4"-ethylterphenyl. (Compound expressed by general formula (1) wherein $R_1$ represents propyl group, $X_1$, $X_2$, and $X_3$ represent a covalent bond, $Y_1$ represents ethyl group, $H_2$ to $H_{12}$ represent hydrogen atom, and $H_1$ represents fluorine atom; Compound No. c-1)

To a mixture of 4-bromo-4'-ethylbiphenyl (748 mmol) and 500 ml of THF was added dropwise 500 ml of a solution of n-butyl lithium (corresponding to 785 mmol) in hexane at −78° C. in 1.5 hours, and stirred at the same temperature for 2.0 hours. To this solution was added dropwise 150 ml of a solution of trimethyl borate (1,496 mmol) in THF, the solution was gradually warmed up to room temperature, and then the solution was stirred overnight. After 750 ml of 7.3% hydrochloric acid was added and stirred for 30 min, the reaction solution was extracted twice with diethyl ether, washed thrice with water, and then dried over anhydrous magnesium sulfate. The solvent was distilled off and the residue was recrystallized from about 1,600 ml of toluene and 500 ml of acetone to give a white solid of 4'-ethylbiphenyl-4-boric acid (572 mmol).

Mixture of 4'-ethylbiphenyl-4-boric acid (177 mmol), 1-bromo-3-fluorobenzene (195 mmol), potassium carbonate (354 mmol), 3.0 g of 5% palladium carbon, 260 ml of toluene, 260 ml of ethanol, and 13 ml of water was refluxed for 7 hours. After allowed to cool, 500 ml of toluene was added to the reaction solution to homogenize, filtered and then dried over anhydrous magnesium sulfate.

The solvent was distilled off and the residue was purified by column chromatography (eluent: toluene) and recrystallization (solvent for recrystallization: ethanol/toluene=5/2) to give a colorless plate-like solid of 3-fluoro-4"-ethylterphenyl (121 mmol).

To a mixture of 3-fluoro-4"-ethylterphenyl (21.7 mmol) and 100 ml of THF, was added dropwise a solution of sec-butyl lithium (corresponding to 23.9 mmol) in cyclohexane while keeping them at −78° C., and stirred at the same temperature for 40 min. While keeping the solution at −78° C., 10 ml of a solution of 4-propylcyclohexanone (26.0 mmol) in THF was added thereto. While stirring, the solution was gradually backed up to room temperature and then stirred overnight. After 30 ml of 7.3% hydrochloric acid was added and stirred for 30 min, the reaction solution was extracted twice with toluene, washed four times with water, and then dried over anhydrous magnesium sulfate.

The solvent was distilled off and the residue was purified by column chromatography (eluent: toluene) to give a colorless solid of 4-(1-hydroxy-4-propylcyclohexyl)-3-fluoro-4"-ethylterphenyl (17.2 mmol).

Mixture of 4-(1-hydroxy-4-propylcyclohexyl)-3-fluoro-4"-ethylterphenyl (24.5 mmol), Amberlist 15E produced by Organo Corp. (0.5 g), and 250 ml of toluene was heated to reflux while taking out the resulting water for 6.5 hours. After allowed to cool, the reaction solution was filtered.

The solvent was distilled off and the residue was purified by column chromatography (eluent: toluene) to give a colorless solid of 4-(4-propyl-1-cyclohexenyl)-3-fluoro-4"-ethylterphenyl (24.0 mmol).

To 4-(4-propyl-1-cyclohexenyl)-3-fluoro-4"-ethylterphenyl (24.0 mmol) was added 500 ml of toluene and 20 g of Raney nickel, and stirred hydrogen gas atmosphere for 12 hours. After termination of absorption of the hydrogen gas was confirmed, the catalyst was filtered off.

The solvent was distilled off and the residue was purified by column chromatography (eluent: toluene) and further purified by repeating recrystallization (solvent for recrystallization: ethanol/toluene=3/1) four times to give a colorless crystal of the subject compound (11.0 mmol). Various spectral data of the compound well supported its structure as follows:

1H-NMR: δ (ppm): 7.22–7.63 (m, 10H), 2.90–3.10 (brs, 1H), 2.71 (q, 2H), 0.80–2.10 (m, 19H)

GC-MS: 400 (M+)

Further, the subject compound exhibited liquid crystallinity and its phase transition temperatures were as follows:

C-C point: 98.2° C., C-S point: 156.2° C. S-N point: 188.6° C.

N-I point: 317.9° C.

EXAMPLE 4

Preparation of 4-(4-propylcyclohexyl)-2,5-difluoro-4"-ethylterphenyl (Compound expressed by general formula (1) wherein $R_1$ represents propyl group, $X_1$, $X_2$, and $X_3$ represent a covalent bond, $Y_1$ represents ethyl group, $H_2$, $H_3$, and $H_5$ to $H_{12}$ represent hydrogen atom, and $H_1$ and $H_4$ represent fluorine atom; Compound No. d-1)

To a mixture of 4-bromo-4'-ethylbiphenyl (748 mmol) and 500 ml of THF was added dropwise 500 ml of a solution of n-butyl lithium (corresponding to 785 mmol) in hexane at −78° C. in 1.5 hours, and stirred at the same temperature for 2.0 hours. To this solution was added dropwise 150 ml of a solution of trimethyl borate (1,496 mmol) in THF, the solution was gradually warmed up to room temperature, and then the solution was stirred overnight. After 750 ml of 7.3% hydrochloric acid was added and stirred 30 min, the reaction solution was extracted twice with diethyl ether, washed thrice with water, and then dried over anhydrous magnesium sulfate. The solvent was distilled off and the residue was recrystallized from about 1,600 ml of toluene and 500 ml of acetone to obtain white solid of 4'-ethylbiphenyl-4-boric acid (572 mmol).

Mixture of 4'-ethylbipheny-4-boric acid (123 mmol), 1,4-dibromo-2,5-difluorobenzene (184 mmol), potassium carbonate (245 mmol), 3.0 g of 5% palladium carbon, 240 ml of toluene, 240 ml of ethanol, and 12 ml of water was refluxed for 7.3 hours. After allowed to cool, 300 ml of toluene was added to the reaction solution to homogenize, and then the solution was dried over anhydrous magnesium sulfate.

The solvent was distilled off and the residue was purified by column chromatography (eluent: heptane) and recrystallization (solvent for recrystallization: ethanol/toluene=15/4) to give a colorless plate-like solid of 4-bromo-2,5-difluoro-4"-ethylterphenyl (41.3 mmol).

To a mixture of 4-bromo-2,5-difluoro-4"-ethylterphenyl (21.4 mmol) and 130 ml of THF, was added dropwise a solution of n-butyl lithium (corresponding to 23.6 mmol) in hexane, and stirred at the same temperature for 3 hours. While keeping the solution at −78° C., 10 ml of a solution of 4-propylcyclohexanone (25.7 mmol) in THF was added thereto. While stirring, the solution was gradually backed up to room temperature and then stirred overnight. After 67 ml of 7.3% hydrochloric acid was added and stirred for 30 min, the reaction solution was extracted twice with toluene, washed four times with water, and then dried over anhydrous magnesium sulfate.

The solvent was distilled off and the residue was purified by column chromatography (eluent: toluene) to give a colorless solid of 4-(1-hydroxy-4-propylcyclohexyl)-2,5-difluoro-4"-ethylterphenyl (15.3 mmol).

Mixture of 4-(1-hydroxy-4-propylcyclohexyl)-2,5-difluoro- 4"-ethylterphenyl (16.1 mmol), Amberlist 15E produced by Organo Corp. (0.35 g), and 250 ml of toluene was heated while taking out the resulting water for 6.0 hours. After allowed to cool, the reaction solution was fileterd.

The solvent was distilled off and the residue was purified by column chromatography (eluent: toluene) to give a colorless solid of 4-(4-propyl-1-cyclohexenyl)-2,5-difluoro-4"-ethylterphenyl (15.3 mmol).

To 4-(4-propyl-1-cyclohexenyl)-2,5-difluoro-4"-ethylterphenyl (15.3 mmol) was added 400 ml of toluene and 15 g of Raney nickel, and stirred under hydrogen gas atmosphere for 21 hours. After termination of absorption of hydrogen was confirmed, the catalyst was filtered off.

The solvent was distilled off and the residue was purified by column chromatography (eluent: toluene) and further purified by repeating recrystallization (solvent for recrystallization: ethanol/toluene=20/3) four times to give a colorless crystal of the subject compound (3.50 mmol). Various spectral data of the compound well supported its structure as follows:

1H-NMR: δ (ppm): 6.91–7.71 (m, 10H), 2.90–3.10 (brs, 1H), 2.70 (q, 2H), 0.80–2.10 (m, 19H)

GC-MS: 400 (M+)

Further, the subject compound exhibited liquid crystallinity and its phase transition temperatures were as follows:

C-C point: 117.5° C., C-N point: 122.2° C., N-I point: 286.6° C.

EXAMPLE 5

Preparation of 4-(4-pentylcyclohexyl)-2,6-difluoro-4"-ethylterphenyl (Compound expressed by general formula (1) wherein $R_1$ represents pentyl group, $X_1$, $X_2$, and $X_3$ represent a covalent bond, $Y_1$ represents ethyl group, $H_1$, $H_3$, and $H_5$ to $H_{12}$ represent hydrogen atom, and $H_2$ and $H_4$ represent fluorine atom; Compound No. d-25)

To a mixture of magnesium (600 mmol) and 1,300 ml of THF was added dropwise 1-bromo-3,5-difluorobenzene (500 mmol) at room temperature, and stirred at the same temperature for 30 min to prepare a Grignard reagent. To this solution was added dropwise a mixture of 4-pentylcyclohexanone (600 mmol) and 200 ml of THF, and stirred at the same temperature overnight. After 600 ml of 1N hydrochloric acid was added and stirred for 30 min, the reaction solution was extracted twice with diethyl ether and dried over anhydrous magnesium sulfate. The solvent was distilled off to give a (1-hydroxy-4-pentylcyclohexyl)-3,5-difluorobenzene (550 mmol). Purification was not particularly performed.

Mixture of (1-hydroxy-4-pentylcyclohexyl)-3,5-difluorobenzene (300 mmol), the Amberlist 15E (4.0 g), and 1,000 ml of toluene was refluxed for 6 hours. After allowed to cool, the Amberlist 15E was filtered off, the solvent was distilled off, and the residue was purified by column chromatography (eluent: heptane) to give a (4-pentyl-1-cyclohexenyl)-3,5-difluorobenzene (170 mmol).

Mixture of (4-pentyl-1-cyclohexenyl)-3,5-difluorobenzene (89 mmol), Raney nickel (3.5 g), and 500 ml of Solmix was subjected to a hydrogenation reaction at room temperature under normal pressure for 10 hours. At the time when the amount of hydrogen has come not to further reduce and the reaction has come not to progress, catalyst was changed from Raney nickel to palladium carbon (2.4 g), and stirred for 8 hours. Palladium carbon was filtered off and the solvent was distilled off. The residue was purified by column chromatography (eluent: heptane) to give a (4-pentyl-cyclohexyl)-3,5-difluorobenzene (81 mmol).

To a mixture of (4-pentyl-cyclohexyl)-3,5-difluorobenzene (10 mmol) and 150 ml of THF, was added dropwise 7.5 ml of a solution of n-butyl lithium (corresponding to 12 mmol) in hexane while keeping them at a temperature lower than −70° C., and stirred at the same temperature for 30 min. While keeping the solution at a temperature lower than −70° C., iodine (30 mmol) was added thereto. Then, the solution was stirred for 1.5 hours, temperature of the solution was gradually backed up to room temperature, and then the solution was stirred for 2 hours. After 12 ml of 1N hydrochloric acid was added and stirred for 30 min, the reaction solution was extracted once with toluene and dried over anhydrous sodium sulfate. The solvent was distilled off and the residue was purified by column chromatography (eluent: heptane) to give a (4-pentyl-cyclohexyl)-3,5-difluoro-4-iodobenzene (8.3 mmol).

Mixture of (4-pentyl-cyclohexyl)-3,5-difluoro-4-iodobenzene (5 mmol), 4-ethyl-biphenyl-4-boric acid (6 mmol), sodium carbonate (18 mmol), tetrakis(triphenylphosphino)palladium (0.6 mmol), 50 ml of toluene, and 50 ml of water was refluxed for 11 hours. After allowed to cool, the organic layer was separated and dried over anhydrous sodium sulfate. The solvent was distilled off and the residue was purified by column chromatography (eluent: heptane) and recrystallizations (solvent for recrystallization: heptane) repeated twice to give the subject compound (3 mmol). Various spectral data of the compound well supported its structure as follows:

1H-NMR: δ (ppm): 6.65–7.85 (m, 10H), 2.20–2.95 (m, 2H), 0.78–2.10 (m, 24H)

Further, the subject compound exhibited liquid crystallinity and its phase transition temperatures were as follows:

C-N point: 143.3° C., Decomposed at 230° C.

EXAMPLE 6

Preparation of 4-(4-pentylcyclohexyl)-3',5'-difluoro-4"-ethylterphenyl (Compound expressed by general formula (1) wherein $R_1$ represents propyl group, $X_1$, $X_2$, and $X_3$ represent a covalent bond, $Y_1$ represents ethyl group, $H_1$ to $H_5$, $H_7$, and $H_9$ to $H_{12}$ represent hydrogen atom, and $H_6$ and $H_8$ represent fluorine atom; Compound No. d-43)

To a mixture of 1-bromo-3,5-difluorobenzene (743 mmol) and 500 ml of THF was added dropwise 500 ml of a solution of n-butyl lithium (corresponding to 780 mmol) in hexane at −78° C. in 1.6 hours, and stirred at the same temperature for 1.5 hours. To this solution was wadded dropwise 200 ml of a solution of triisopropyl borate (1,486 mmol) in THF, the solution was gradually warmed up to room temperature, and then the solution was stirred overnight. After 750 ml of 7.3% hydrochloric acid was added and stirred for 30 min, the reaction solution was extracted twice with diethyl ether, washed thrice with water, and then dried over anhydrous magnesium sulfate. The solvent was distilled off and the residue was recrystallized from about 1,000 ml of toluene to give a white solid of 3,5-difluorophenyl boric acid (520 mmol).

Mixture of 3,5-difluorophenyl boric acid (73.6 mmol), 1-bromo-4-iodobenzene (77.5 mmol), potassium carbonate (147 mmol), 0.5 g of 5% palladium carbon, 100 ml of toluene, 100 ml of ethanol, and 6.0 ml of water was refluxed for 5 hours. After allowed to cool, the reaction solution was filtered and dried over anhydrous magnesium sulfate.

The solvent was distilled off and the residue was purified by column chromatography (eluent: toluene/n-heptane=1/9) and recrystallization (solvent for recrystallization: ethanol) to give a colorless solid of 4-bromo-3',5'-difluorobiphenyl (45.0 mmol).

Mixture of 4-bromo-3',5'-difluorobiphenyl (44.0 mmol), iodic acid (22.0 mmol), iodine (26.6 mmol), acetic acid (33 ml), water (4.0 ml), and carbon tetrachloride (4.0 ml) was refluxed for 24 hours. After allowed to cool, the reaction solution was extracted twice with heptane and washed twice with water. Subsequently, it was further washed with 160 ml of 4% aqueous solution of sodium thiosulfate, washed thrice with water, and then dried over anhydrous magnesium sulfate.

The solvent was distilled off and the residue was purified by column chromatography (eluent: toluene/n-heptane=1/9) and recrystallizations (solvent for recrystallization: ethanol) repeated twice to give a pale yellow-green crystal of 4-bromo-3',5'-difluoro-4'-iodobiphenyl (10.6 mmol).

To a mixture of 1-bromo-4-ethylbenzene (743 mmol) and 500 ml of THF, was added dropwise 500 ml of a solution of n-butyl lithium (corresponding to 780 mmol) in hexane at −78° C. in 1.6 hours, and stirred at the same temperature for 1.5 hours. To this solution was added dropwise 200 ml of a solution of triisopropyl borate (1,486 mmol) in THF, the solution was gradually warmed up to room temperature, and then the solution was stirred overnight. After 750 ml of 7.3% hydrochloric acid was added and stirred for 30 min, the reaction solution was extracted twice with diethyl ether, washed thrice with water, and then dried over anhydrous magnesium sulfate. The solvent was distilled off and the residue was recrystallized from about 1,000 ml of toluene to give a white solid of 4-ethylphenyl boric acid (515 mmol).

Mixture of 4-ethylphenyl boric acid (9.50 mmol), 4-bromo-3',5'-difluoro-4'-iodobiphenyl (10.0 mmol), potassium carbonate (19.0 mmol), 0.07 g of 5% palladium carbon, 13 ml of toluene, 13 ml of ethanol, and 0.8 ml of water was refluxed for 5 hours. After allowed to cool, the reaction solution was filtered and dried over anhydrous magnesium sulfate.

The solvent was distilled off and the residue was purified by column chromatography (eluent: toluene/n-heptane=1/9) and recrystallization (solvent for recrystallization: ethanol)

to give a colorless solid of 4-bromo-3',5'-difluoro-4"-ethylterphenyl (7.05 mmol).

To a mixture of 4-bromo-3',5'-difluoro-4"-ethylterphenyl (7.00 mmol) and 44 ml of THF, was added a solution of n-butyl lithium (corresponding to 7.72 mmol) in hexane while keeping it at −78° C., and stirred at the same temperature for 3 hours. While keeping the solution at −78° C., 10 ml of a solution of 4-pentylcyclohexanone (8.40 mmol) in THF was added, and it was gradually backed up to room temperature while stirring and then stirred overnight. After 22 ml of 7.3% hydrochloric acid was added and stirred for 30 min, the reaction solution was extracted twice with toluene, washed four times with water, and then dried over anhydrous magnesium sulfate.

The solvent was distilled off and the residue was purified by column chromatography (eluent: toluene) to give a colorless solid of 4-(1-hydroxy-4-pentylcyclohexyl)-3',5'-difluoro-4"-ethylterphenyl (5.10 mmol).

Mixture of 4-(1-hydroxy-4-pentylcyclohexyl)-3',5'-difluoro-4"-ethylterphenyl (5.00 mmol), the Amberlist 15E (0.12 g), and 80 ml of toluene was heated to reflux while taking out the resulting water for 6.0 hours. After allowed to cool, the reaction solution was filtered.

The solvent was distilled off and the residue was purified by column chromatography (eluent: toluene) to give a colorless solid of 4-(4-pentyl-1-cyclohexenyl)-3',5'-difluoro-4"-ethylterphenyl (4.75 mmol).

To 4-(4-pentyl-1-cyclohexenyl)-3',5'-difluoro-4"-ethylterphenyl (4.75 mmol) were added 400 ml of toluene and 15 g or Raney nickel, and they were stirred under hydrogen gas atmosphere for 20 hours. After termination of hydrogen was confirmed, the catalyst was filtered.

The solvent was distilled off and the residue was purified by column chromatography (eluent: toluene) and further purified by repeating recrystallization (solvent for recrystallization: ethanol/toluene=20/3) four times to give a colorless crystal of the subject compound (1.15 mmol). Various spectral data of the compound well supported its structure.

EXAMPLE 7

According to Examples 1 to 6, the following compounds expressed by general formula (1) are prepared

TABLE 1

| No. | R1 | X1 | X2 | X3 | H 1 | H 2 | H 3 | H 4 | H 5 | H 6 | H 7 | H 8 | H 9 | H 10 | H 11 | H 12 | Y1 |
|---|---|---|---|---|---|---|---|---|---|---|---|---|---|---|---|---|---|
| a-1 | $CH_3OCH_2-$ | — | — | — | H | H | H | H | F | H | H | H | H | H | H | H | $-CH_3$ |
| a-2 | $CH_3OCH_2-$ | — | — | — | H | H | H | H | F | H | H | H | H | H | H | H | $-C_2H_5$ |
| a-3 | $CH_3OCH_2-$ | — | — | — | H | H | H | H | Cl | H | H | H | H | H | H | H | $-C_3H_7$ |
| a-4 | $CH_3OCH_2-$ | — | — | — | H | H | H | H | F | H | H | H | H | H | H | H | $-C_4H_9$ |
| a-5 | $CH_3OCH_2-$ | — | — | — | H | H | H | H | F | H | H | H | H | H | H | H | $-C_5H_{11}$ |
| a-7 | $C_2H_5OCH_2-$ | — | — | — | H | H | H | H | F | H | H | H | H | H | H | H | $-C_2H_5$ |
| a-8 | $CH_3OC_2H_4-$ | — | — | — | H | H | H | H | F | H | H | H | H | H | H | H | $-C_2H_5$ |
| a-9 | $C_3H_7OCH_2-$ | — | — | — | H | H | H | H | Cl | H | H | H | H | H | H | H | $-C_2H_5$ |
| a-10 | $CH_3OC_3H_6-$ | — | — | — | H | H | H | H | F | H | H | H | H | H | H | H | $-C_2H_5$ |
| a-11 | $CH_3O-$ | — | — | — | H | H | H | H | F | H | H | H | H | H | H | H | $-C_2H_5$ |
| a-12 | $C_2H_5O-$ | — | — | — | H | H | H | H | F | H | H | H | H | H | H | H | $-C_2H_5$ |
| a-13 | $C_3H_7O-$ | — | — | — | H | H | H | H | F | H | H | H | H | H | H | H | $-C_2H_5$ |
| a-14 | $CH_3OCH_2-$ | $(CH_2)_2$ | — | — | H | H | H | H | F | H | H | H | H | H | H | H | $-C_2H_5$ |
| a-15 | $CH_3OCH_2-$ | — | $(CH_2)_2$ | — | H | H | H | H | F | H | H | H | H | H | H | H | $-C_2H_5$ |
| a-16 | $CH_3OCH_2-$ | — | — | $(CH_2)_2$ | H | H | H | H | Cl | H | H | H | H | H | H | H | $-C_2H_5$ |
| a-17 | $CH_3OCH_2-$ | $(CH_2)_2$ | $(CH_2)_2$ | — | H | H | H | H | F | H | H | H | H | H | H | H | $-C_2H_5$ |
| a-18 | $CH_3OCH_2-$ | — | $(CH_2)_2$ | $(CH_2)_2$ | H | H | H | H | F | H | H | H | H | H | H | H | $-C_2H_5$ |
| a-19 | $CH_3OCH_2-$ | $(CH_2)_2$ | — | $(CH_2)_2$ | H | H | H | H | F | H | H | H | H | H | H | H | $-C_2H_5$ |
| a-20 | $CH_3OCH_2-$ | $(CH_2)_4$ | — | — | H | H | H | H | F | H | H | H | H | H | H | H | $-C_2H_5$ |

TABLE 2

| No. | R1 | X1 | X2 | X3 | H 1 | H 2 | H 3 | H 4 | H 5 | H 6 | H 7 | H 8 | H 9 | H 10 | H 11 | H 12 | Y1 |
|---|---|---|---|---|---|---|---|---|---|---|---|---|---|---|---|---|---|
| a-21 | $CH_3OCH_2-$ | — | $(CH_2)_4$ | — | H | H | H | H | F | H | H | H | H | H | H | H | $-C_2H_5$ |
| a-22 | $CH_3OCH_2-$ | — | — | $(CH_2)_4$ | H | H | H | H | F | H | H | H | H | H | H | H | $-C_2H_5$ |
| a-23 | $CH_3OCH_2-$ | $(CH_2)_4$ | $(CH_2)_4$ | — | H | H | H | H | F | H | H | H | H | H | H | H | $-C_2H_5$ |
| a-24 | $CH_3OCH_2-$ | — | $(CH_2)_4$ | $(CH_2)_4$ | H | H | H | H | F | H | H | H | H | H | H | H | $-C_2H_5$ |
| a-25 | $CH_3OCH_2-$ | $(CH_2)_4$ | — | $(CH_2)_4$ | H | H | H | H | F | H | H | H | H | H | H | H | $-C_2H_5$ |
| a-26 | $CH_3OCH_2-$ | — | — | — | F | H | H | H | H | H | H | H | H | H | H | H | $-C_2H_5$ |
| a-27 | $CH_3OCH_2-$ | — | — | — | H | H | H | H | F | H | H | H | H | H | H | H | $-OC_2H_5$ |
| a-28 | $CH_3OCH_2-$ | — | — | — | H | H | H | H | F | H | H | H | H | H | H | H | $-SC_2H_5$ |
| a-29 | $CH_3OCH_2-$ | — | — | — | H | H | H | H | F | H | H | H | H | H | H | H | $-SiH_2C_2H_5$ |
| a-30 | $CH_3OCH_2-$ | — | — | — | H | H | H | H | F | H | H | H | H | H | H | H | $-Si(CH_3)_2C_2H_5$ |
| a-31 | $CH_3OCH_2-$ | — | — | — | H | H | H | H | F | H | H | H | H | H | H | H | $-CH=CH-C_2H_5$ |
| a-32 | $CH_3OCH_2-$ | — | — | — | H | H | H | H | F | H | H | H | H | H | H | H | $-C\equiv C-C_2H_5$ |
| a-33 | $CH_2=CH-CH_2-$ | — | — | — | H | H | H | H | F | H | H | H | H | H | H | H | $-C_2H_5$ |
| a-34 | $CH_2=CH-(CH_2)_2-$ | — | — | — | H | H | H | H | F | H | H | H | H | H | H | H | $-C_2H_5$ |
| a-35 | $CH_3-CH=CH-(CH_2)_2-$ | — | — | — | H | H | H | H | F | H | H | H | H | H | H | H | $-C_2H_5$ |

TABLE 3

| No. | R1 | X1 | X2 | X3 | 1 | 2 | 3 | 4 | 5 | 6 | 7 | 8 | 9 | 10 | 11 | 12 | Y1 |
|---|---|---|---|---|---|---|---|---|---|---|---|---|---|---|---|---|---|
| b-1  | $CH_3OCH_2-$   | —        | —        | —        | H | H | H | H | F  | H | H | F  | H | H | H | H | $-CH_3$ |
| b-2  | $CH_3OCH_2-$   | —        | —        | —        | H | H | H | H | F  | H | H | F  | H | H | H | H | $-C_2H_5$ |
| b-3  | $CH_3OCH_2-$   | —        | —        | —        | H | H | H | H | Cl | H | H | F  | H | H | H | H | $-C_3H_7$ |
| b-4  | $CH_3OCH_2-$   | —        | —        | —        | H | H | H | H | F  | H | H | F  | H | H | H | H | $-C_4H_9$ |
| b-5  | $CH_3OCH_2-$   | —        | —        | —        | H | H | H | H | F  | H | H | Cl | H | H | H | H | $-C_5H_{11}$ |
| b-7  | $C_2H_5OCH_2-$ | —        | —        | —        | H | H | H | H | F  | H | H | F  | H | H | H | H | $-C_2H_5$ |
| b-8  | $CH_3OC_2H_4-$ | —        | —        | —        | H | H | H | H | F  | H | H | F  | H | H | H | H | $-C_2H_5$ |
| b-9  | $C_3H_7OCH_2-$ | —        | —        | —        | H | H | H | H | F  | H | H | F  | H | H | H | H | $-C_2H_5$ |
| b-10 | $CH_3OC_3H_6-$ | —        | —        | —        | H | H | H | H | F  | H | H | F  | H | H | H | H | $-C_2H_5$ |
| b-11 | $CH_3O-$       | —        | —        | —        | H | H | H | H | F  | H | H | F  | H | H | H | H | $-C_2H_5$ |
| b-12 | $C_2H_5O-$     | —        | —        | —        | H | H | H | H | F  | H | H | F  | H | H | H | H | $-C_2H_5$ |
| b-13 | $C_3H_7O-$     | —        | —        | —        | H | H | H | H | Cl | H | H | F  | H | H | H | H | $-C_2H_5$ |
| b-14 | $CH_3OCH_2-$   | $(CH_2)_2$ | —      | —        | H | H | H | H | F  | H | H | F  | H | H | H | H | $-C_2H_5$ |
| b-15 | $CH_3OCH_2-$   | —        | $(CH_2)_2$ | —      | H | H | H | H | F  | H | H | F  | H | H | H | H | $-C_2H_5$ |
| b-16 | $CH_3OCH_2-$   | —        | —        | $(CH_2)_2$ | H | H | H | H | F | H | H | F | H | H | H | H | $-C_2H_5$ |
| b-17 | $CH_3OCH_2-$   | $(CH_2)_2$ | $(CH_2)_2$ | —    | H | H | H | H | F  | H | H | F  | H | H | H | H | $-C_2H_5$ |
| b-18 | $CH_3OCH_2-$   | —        | $(CH_2)_2$ | $(CH_2)_2$ | H | H | H | H | F | H | H | Cl | H | H | H | H | $-C_2H_5$ |
| b-19 | $CH_3OCH_2-$   | $(CH_2)_2$ | —      | $(CH_2)_2$ | H | H | H | H | F | H | H | F  | H | H | H | H | $-C_2H_5$ |
| b-20 | $CH_3OCH_2-$   | $(CH_2)_4$ | —      | —        | H | H | H | H | F  | H | H | F  | H | H | H | H | $-C_2H_5$ |

TABLE 4

| No. | R1 | X1 | X2 | X3 | 1 | 2 | 3 | 4 | 5 | 6 | 7 | 8 | 9 | 10 | 11 | 12 | Y1 |
|---|---|---|---|---|---|---|---|---|---|---|---|---|---|---|---|---|---|
| b-21 | $CH_3OCH_2-$   | —          | $(CH_2)_4$ | —          | H | H | H | H | F  | H | H | F  | H | H | H | H | $-C_2H_5$ |
| b-22 | $CH_3OCH_2-$   | —          | —          | $(CH_2)_4$ | H | H | H | H | F  | H | H | F  | H | H | H | H | $-C_2H_5$ |
| b-23 | $CH_3OCH_2-$   | $(CH_2)_4$ | $(CH_2)_4$ | —          | H | H | H | H | F  | H | H | F  | H | H | H | H | $-C_2H_5$ |
| b-24 | $CH_3OCH_2-$   | —          | $(CH_2)_4$ | $(CH_2)_4$ | H | H | H | H | F  | H | H | F  | H | H | H | H | $-C_2H_5$ |
| b-25 | $CH_3OCH_2-$   | $(CH_2)_4$ | —          | $(CH_2)_4$ | H | H | H | H | F  | H | H | F  | H | H | H | H | $-C_2H_5$ |
| b-26 | $CH_3OCH_2-$   | —          | —          | —          | H | H | H | H | F  | F | H | H  | H | H | H | H | $-C_2H_5$ |
| b-27 | $CH_3OCH_2-$   | —          | —          | —          | H | H | H | H | H  | F | F | H  | H | H | H | H | $-C_2H_5$ |
| b-28 | $CH_3OCH_2-$   | —          | —          | —          | H | H | H | H | H  | F | H | F  | H | H | H | H | $-C_2H_5$ |
| b-29 | $C_2H_5OCH_2-$ | —          | —          | —          | H | H | H | H | H  | F | H | F  | H | H | H | H | $-C_3H_7$ |
| b-30 | $C_2H_5OCH_2-$ | —          | —          | —          | H | H | H | H | H  | F | H | F  | H | H | H | H | $-C_4H_9$ |
| b-31 | $CH_3OC_2H_4-$ | —          | —          | —          | H | H | H | H | H  | F | H | F  | H | H | H | H | $-C_5H_{11}$ |
| b-32 | $CH_3OC_2H_4-$ | —          | —          | —          | H | H | H | H | H  | Cl| H | F  | H | H | H | H | $-OC_2H_5$ |
| b-33 | $C_3H_7OCH_2-$ | —          | —          | —          | H | H | H | H | H  | F | H | F  | H | H | H | H | $-C_3H_7$ |
| b-34 | $C_3H_7OCH_2-$ | —          | —          | —          | H | H | H | H | H  | F | H | F  | H | H | H | H | $-C_4H_9$ |
| b-35 | $CH_3OC_3H_6-$ | —          | —          | —          | H | H | H | H | H  | F | H | F  | H | H | H | H | $-C_5H_{11}$ |
| b-36 | $CH_3OC_3H_6-$ | —          | —          | —          | H | H | H | H | H  | F | H | F  | H | H | H | H | $-OC_2H_5$ |
| b-37 | $CH_3O-$       | —          | —          | —          | H | H | H | H | H  | F | H | F  | H | H | H | H | $-C_3H_7$ |
| b-38 | $CH_3O-$       | —          | —          | —          | H | H | H | H | H  | F | H | F  | H | H | H | H | $-C_4H_9$ |
| b-39 | $C_2H_5O-$     | —          | —          | —          | H | H | H | H | H  | F | H | F  | H | H | H | H | $-C_5H_{11}$ |
| b-40 | $C_2H_5O-$     | —          | —          | —          | H | H | H | H | H  | F | H | F  | H | H | H | H | $-OC_2H_5$ |

TABLE 5

| No. | R1 | X1 | X2 | X3 | 1 | 2 | 3 | 4 | 5 | 6 | 7 | 8 | 9 | 10 | 11 | 12 | Y1 |
|---|---|---|---|---|---|---|---|---|---|---|---|---|---|---|---|---|---|
| b-41 | $C_3H_7O-$     | — | — | — | H | H | H | H | H | F | H | F  | H | H | H | H | $-C_3H_7$ |
| b-42 | $C_3H_7O-$     | — | — | — | H | H | H | H | H | F | H | Cl | H | H | H | H | $-C_4H_9$ |
| b-43 | $CH_3OCH_2-$   | — | — | — | F | F | H | H | H | H | H | H  | H | H | H | H | $-C_2H_5$ |
| b-44 | $CH_3OCH_2-$   | — | — | — | F | H | F | H | H | H | H | H  | H | H | H | H | $-C_2H_5$ |
| b-45 | $CH_3OCH_2-$   | — | — | — | F | H | H | F | H | H | H | H  | H | H | H | H | $-C_2H_5$ |
| b-46 | $CH_3OCH_2-$   | — | — | — | H | F | H | F | H | H | H | H  | H | H | H | H | $-C_2H_5$ |
| b-47 | $C_2H_5OCH_2-$ | — | — | — | H | F | H | F | H | H | H | H  | H | H | H | H | $-C_3H_7$ |
| b-48 | $C_2H_5OCH_2-$ | — | — | — | H | F | H | F | H | H | H | H  | H | H | H | H | $-C_4H_9$ |
| b-49 | $CH_3OC_2H_4-$ | — | — | — | H | F | H | F | H | H | H | H  | H | H | H | H | $-C_5H_{11}$ |
| b-50 | $CH_3OC_2H_4-$ | — | — | — | H | F | H | F | H | H | H | H  | H | H | H | H | $-OC_2H_5$ |

TABLE 5-continued

| No. | R1 | X1 | X2 | X3 | 1 | 2 | 3 | 4 | 5 | 6 | 7 | 8 | 9 | 10 | 11 | 12 | Y1 |
|---|---|---|---|---|---|---|---|---|---|---|---|---|---|---|---|---|---|
| b-51 | $C_3H_7OCH_2$— | — | — | — | H | F | H | F | H | H | H | H | H | H | H | H | —$C_3H_7$ |
| b-52 | $C_3H_7OCH_2$— | — | — | — | H | F | H | F | H | H | H | H | H | H | H | H | —$C_4H_9$ |
| b-53 | $CH_3OC_3H_6$— | — | — | — | H | F | H | F | H | H | H | H | H | H | H | H | —$C_5H_{11}$ |
| b-54 | $CH_3OC_3H_6$— | — | — | — | H | F | H | F | H | H | H | H | H | H | H | H | —$OC_2H_5$ |
| b-55 | $CH_3O$— | — | — | — | H | F | H | F | H | H | H | H | H | H | H | H | —$C_3H_7$ |
| b-56 | $CH_3O$— | — | — | — | H | F | H | F | H | H | H | H | H | H | H | H | —$C_4H_9$ |
| b-57 | $C_2H_5O$— | — | — | — | H | F | H | F | H | H | H | H | H | H | H | H | —$C_5H_{11}$ |
| b-58 | $C_2H_5O$— | — | — | — | H | F | H | F | H | H | H | H | H | H | H | H | —$OC_2H_5$ |
| b-59 | $C_3H_7O$— | — | — | — | H | Cl | H | F | H | H | H | H | H | H | H | H | —$C_3H_7$ |
| b-60 | $C_3H_7O$— | — | — | — | H | F | H | F | H | H | H | H | H | H | H | H | —$C_4H_9$ |

TABLE 6

| No. | R1 | X1 | X2 | X3 | 1 | 2 | 3 | 4 | 5 | 6 | 7 | 8 | 9 | 10 | 11 | 12 | Y1 |
|---|---|---|---|---|---|---|---|---|---|---|---|---|---|---|---|---|---|
| a-61 | $CH_3OCH_2$— | — | — | — | F | H | H | H | F | H | H | H | H | H | H | H | —$C_2H_5$ |
| b-62 | $CH_3OCH_2$— | — | — | — | F | H | H | H | H | H | H | F | H | H | H | H | —$C_2H_5$ |
| b-63 | $CH_3OCH_2$— | — | — | — | H | F | H | H | F | H | H | H | F | H | H | H | —$C_2H_5$ |
| b-64 | $CH_3OCH_2$— | — | — | — | H | H | H | H | F | H | H | F | H | H | H | H | —$OC_2H_5$ |
| b-65 | $CH_3OCH_2$— | — | — | — | H | H | H | H | F | H | H | F | H | H | H | H | —$SC_2H_5$ |
| b-66 | $CH_3OCH_2$— | — | — | — | H | H | H | H | F | H | H | F | H | H | H | H | —$SiH_2C_2H_5$ |
| b-67 | $CH_3OCH_2$— | — | — | — | H | H | H | H | F | H | H | F | H | H | H | H | —$Si(CH_3)_2C_2H_5$ |
| b-68 | $CH_3OCH_2$— | — | — | — | H | H | H | H | F | H | H | F | H | H | H | H | —$CH=CH$—$C_2H_5$ |
| b-69 | $CH_3OCH_2$— | — | — | — | H | H | H | H | F | H | H | F | H | H | H | H | —$C\equiv C$—$C_2H_5$ |
| b-70 | $CH_2=CH$—$CH_2$— | — | — | — | H | H | H | H | F | H | H | F | H | H | H | H | —$C_2H_5$ |
| b-71 | $CH_2=CH$—$(CH_2)_2$— | — | — | — | H | H | H | H | F | H | H | F | H | H | H | H | —$C_2H_5$ |
| b-72 | $CH_3$—$CH=CH$—$(CH_2)_2$— | — | — | — | H | H | H | H | F | H | F | H | H | H | H | H | —$C_2H_5$ |

TABLE 7

| No. | R1 | X1 | X2 | X3 | 1 | 2 | 3 | 4 | 5 | 6 | 7 | 8 | 9 | 10 | 11 | 12 | Y1 |
|---|---|---|---|---|---|---|---|---|---|---|---|---|---|---|---|---|---|
| c-1 | $C_3H_7$— | — | — | — | F | H | H | H | H | H | H | H | H | H | H | H | —$C_2H_5$ |
| c-2 | $CH_3$— | — | — | — | F | H | H | H | H | H | H | H | H | H | H | H | —$C_2H_5$ |
| c-3 | $C_2H_5$— | — | — | — | F | H | H | H | H | H | H | H | H | H | H | H | —$C_2H_5$ |
| c-4 | $C_4H_9$— | — | — | — | Cl | H | H | H | H | H | H | H | H | H | H | H | —$C_2H_5$ |
| c-5 | $C_5H_{11}$— | — | — | — | F | H | H | H | H | H | H | H | H | H | H | H | —$C_2H_5$ |
| c-7 | $C_3H_7$— | — | — | — | F | H | H | H | H | H | H | H | H | H | H | H | —$CH_3$ |
| c-8 | $C_3H_7$— | — | — | — | F | H | H | H | H | H | H | H | H | H | H | H | —$C_2H_5$ |
| c-9 | $C_3H_7$— | — | — | — | F | H | H | H | H | H | H | H | H | H | H | H | —$C_4H_9$ |
| c-10 | $C_3H_7$— | — | — | — | F | H | H | H | H | H | H | H | H | H | H | H | —$C_5H_{11}$ |
| c-11 | $C_3H_7$— | $(CH_2)_2$ | — | — | F | H | H | H | H | H | H | H | H | H | H | H | —$C_2H_5$ |
| c-12 | $C_3H_7$— | — | $(CH_2)_2$ | — | F | H | H | H | H | H | H | H | H | H | H | H | —$C_2H_5$ |
| c-13 | $C_3H_7$— | — | — | $(CH_2)_2$ | F | H | H | H | H | H | H | H | H | H | H | H | —$C_2H_5$ |
| c-14 | $C_3H_7$— | $(CH_2)_2$ | $(CH_2)_2$ | — | Cl | H | H | H | H | H | H | H | H | H | H | H | —$C_2H_5$ |
| c-15 | $C_3H_7$— | — | $(CH_2)_2$ | $(CH_2)_2$ | F | H | H | H | H | H | H | H | H | H | H | H | —$C_2H_5$ |
| c-16 | $C_3H_7$— | $(CH_2)_2$ | — | $(CH_2)_2$ | F | H | H | H | H | H | H | H | H | H | H | H | —$C_2H_5$ |
| c-17 | $C_3H_7$— | $(CH_2)_4$ | — | — | F | H | H | H | H | H | H | H | H | H | H | H | —$C_2H_5$ |
| c-18 | $C_3H_7$— | — | $(CH_2)_4$ | — | F | H | H | H | H | H | H | H | H | H | H | H | —$C_2H_5$ |
| c-19 | $C_3H_7$— | — | — | $(CH_2)_4$ | F | H | H | H | H | H | H | H | H | H | H | H | —$C_2H_5$ |
| c-20 | $C_3H_7$— | $(CH_2)_4$ | $(CH_2)_4$ | — | F | H | H | H | H | H | H | H | H | H | H | H | —$C_2H_5$ |

TABLE 8

| No. | R1 | X1 | X2 | X3 | H1 | H2 | H3 | H4 | H5 | H6 | H7 | H8 | H9 | H10 | H11 | H12 | Y1 |
|---|---|---|---|---|---|---|---|---|---|---|---|---|---|---|---|---|---|
| c-21 | $C_3H_7-$ | — | $(CH_2)_4$ | $(CH_2)_4$ | F | H | H | H | H | H | H | H | H | H | H | H | $-C_2H_5$ |
| c-22 | $C_3H_7-$ | $(CH_2)_4$ | — | $(CH_2)_4$ | F | H | H | H | H | H | H | H | H | H | H | H | $-C_2H_5$ |
| c-25 | $C_3H_7-$ | — | — | — | F | H | H | H | H | H | H | H | H | H | H | H | $-OC_2H_5$ |
| c-26 | $C_3H_7-$ | — | — | — | F | H | H | H | H | H | H | H | H | H | H | H | $-SC_2H_5$ |
| c-27 | $C_3H_7-$ | — | — | — | F | H | H | H | H | H | H | H | H | H | H | H | $-SiH_2C_2H_5$ |
| c-28 | $C_3H_7-$ | — | — | — | F | H | H | H | H | H | H | H | H | H | H | H | $-Si(CH_3)_2C_2H_5$ |
| c-29 | $C_3H_7-$ | — | — | — | F | H | H | H | H | H | H | H | H | H | H | H | $-CH=CH-C_2H_5$ |
| c-30 | $C_3H_7-$ | — | — | — | F | H | H | H | H | H | H | H | H | H | H | H | $-C\equiv C-C_2H_5$ |
| c-31 | $CH_2=CH-CH_2-$ | — | — | — | F | H | H | H | H | H | H | H | H | H | H | H | $-C_2H_5$ |
| c-32 | $CH_2=CH-(CH_2)_2-$ | — | — | — | F | H | H | H | H | H | H | H | H | H | H | H | $-C_2H_5$ |
| c-33 | $CH_3-CH=CH-(CH_2)_2-$ | — | — | — | F | H | H | H | H | H | H | H | H | H | H | H | $-C_2H_5$ |

TABLE 9

| No. | R1 | X1 | X2 | X3 | H1 | H2 | H3 | H4 | H5 | H6 | H7 | H8 | H9 | H10 | H11 | H12 | Y1 |
|---|---|---|---|---|---|---|---|---|---|---|---|---|---|---|---|---|---|
| d-1 | $C_3H_7-$ | — | — | — | F | H | H | F | H | H | H | H | H | H | H | H | $-C_2H_5$ |
| d-2 | $CH_3-$ | — | — | — | F | H | H | F | H | H | H | H | H | H | H | H | $-C_2H_5$ |
| d-3 | $C_2H_5-$ | — | — | — | F | H | H | Cl | H | H | H | H | H | H | H | H | $-C_2H_5$ |
| d-4 | $C_4H_9-$ | — | — | — | F | H | H | F | H | H | H | H | H | H | H | H | $-C_2H_5$ |
| d-5 | $C_5H_{11}-$ | — | — | — | F | H | H | F | H | H | H | H | H | H | H | H | $-C_2H_5$ |
| d-7 | $C_3H_7-$ | — | — | — | F | H | H | F | H | H | H | H | H | H | H | H | $-CH_3$ |
| d-8 | $C_3H_7-$ | — | — | — | F | H | H | F | H | H | H | H | H | H | H | H | $-C_2H_5$ |
| d-9 | $C_3H_7-$ | — | — | — | F | H | H | F | H | H | H | H | H | H | H | H | $-C_4H_9$ |
| d-10 | $C_3H_7-$ | — | — | — | F | H | H | F | H | H | H | H | H | H | H | H | $-C_5H_{11}$ |
| d-11 | $C_3H_7-$ | $(CH_2)_2$ | — | — | F | H | H | F | H | H | H | H | H | H | H | H | $-C_2H_5$ |
| d-12 | $C_3H_7-$ | — | $(CH_2)_2$ | — | F | H | H | F | H | H | H | H | H | H | H | H | $-C_2H_5$ |
| d-13 | $C_3H_7-$ | — | — | $(CH_2)_2$ | F | H | H | F | H | H | H | H | H | H | H | H | $-C_2H_5$ |
| d-14 | $C_3H_7-$ | $(CH_2)_2$ | $(CH_2)_2$ | — | F | H | H | F | H | H | H | H | H | H | H | H | $-C_2H_5$ |
| d-15 | $C_3H_7-$ | — | $(CH_2)_2$ | $(CH_2)_2$ | Cl | H | H | F | H | H | H | H | H | H | H | H | $-C_2H_5$ |
| d-16 | $C_3H_7-$ | $(CH_2)_2$ | — | $(CH_2)_2$ | F | H | H | F | H | H | H | H | H | H | H | H | $-C_2H_5$ |
| d-17 | $C_3H_7-$ | $(CH_2)_4$ | — | — | F | H | H | F | H | H | H | H | H | H | H | H | $-C_2H_5$ |
| d-18 | $C_3H_7-$ | — | $(CH_2)_4$ | — | F | H | H | F | H | H | H | H | H | H | H | H | $-C_2H_5$ |
| d-19 | $C_3H_7-$ | — | — | $(CH_2)_4$ | F | H | H | F | H | H | H | H | H | H | H | H | $-C_2H_5$ |
| d-20 | $C_3H_7-$ | $(CH_2)_4$ | $(CH_2)_4$ | — | F | H | H | F | H | H | H | H | H | H | H | H | $-C_2H_5$ |

TABLE 10

| No. | R1 | X1 | X2 | X3 | H1 | H2 | H3 | H4 | H5 | H6 | H7 | H8 | H9 | H10 | H11 | H12 | Y1 |
|---|---|---|---|---|---|---|---|---|---|---|---|---|---|---|---|---|---|
| d-21 | $C_3H_7-$ | — | $(CH_2)_4$ | $(CH_2)_4$ | F | H | H | F | H | H | H | H | H | H | H | H | $-C_2H_5$ |
| d-22 | $C_3H_7-$ | $(CH_2)_4$ | — | $(CH_2)_4$ | F | H | H | F | H | H | H | H | H | H | H | H | $-C_2H_5$ |
| d-23 | $C_3H_7-$ | — | — | — | F | F | H | H | H | H | H | H | H | H | H | H | $-C_2H_5$ |
| d-24 | $C_3H_7-$ | — | — | — | F | H | F | H | H | H | H | H | H | H | H | H | $-C_2H_5$ |
| d-25 | $C_5H_{11}-$ | — | — | — | H | F | F | F | H | H | H | H | H | H | H | H | $-C_2H_5$ |
| d-26 | $C_2H_5OCH_2-$ | — | — | — | H | F | H | F | H | H | H | H | H | H | H | H | $-C_3H_7$ |
| d-27 | $C_2H_5OCH_2-$ | — | — | — | H | F | H | Cl | H | H | F | H | H | H | H | H | $-C_4H_9$ |
| d-28 | $CH_3OC_2H_4-$ | — | — | — | H | F | H | F | H | H | H | H | H | H | H | H | $-C_5H_{11}$ |
| d-29 | $CH_3OC_2H_4-$ | — | — | — | H | F | H | F | H | H | H | H | H | H | H | H | $-OC_2H_5$ |
| d-30 | $C_3H_7OCH_2-$ | — | — | — | H | F | H | F | H | H | H | H | H | H | H | H | $-C_3H_7$ |
| d-31 | $C_3H_7OCH_2-$ | — | — | — | H | F | H | F | H | H | H | H | H | H | H | H | $-C_4H_9$ |
| d-32 | $CH_3OC_3H_6-$ | — | — | — | H | F | H | F | H | H | H | H | H | H | H | H | $-C_5H_{11}$ |
| d-33 | $CH_3OC_3H_6-$ | — | — | — | H | F | H | F | H | H | H | H | H | H | H | H | $-OC_2H_5$ |
| d-34 | $CH_3O-$ | — | — | — | H | F | H | F | H | H | H | H | H | H | H | H | $-C_3H_7$ |
| d-35 | $CH_3O-$ | — | — | — | H | F | H | F | H | H | H | H | H | H | H | H | $-C_4H_9$ |
| d-36 | $C_2H_5O-$ | — | — | — | H | F | H | F | H | H | H | H | H | H | H | H | $-C_5H_{11}$ |
| d-37 | $C_2H_5O-$ | — | — | — | H | F | H | F | H | H | H | H | H | H | H | H | $-OC_2H_5$ |
| d-38 | $C_3H_7O-$ | — | — | — | H | Cl | H | F | H | H | H | H | H | H | H | H | $-C_3H_7$ |
| d-39 | $C_3H_7O-$ | — | — | — | H | F | H | F | H | H | H | H | H | H | H | H | $-C_4H_9$ |
| d-40 | $C_3H_7-$ | — | — | — | H | H | H | H | F | F | H | H | H | H | H | H | $-C_2H_5$ |

TABLE 11

| No. | R1 | X1 | X2 | X3 | H1 | H2 | H3 | H4 | H5 | H6 | H7 | H8 | H9 | H10 | H11 | H12 | Y1 |
|---|---|---|---|---|---|---|---|---|---|---|---|---|---|---|---|---|---|
| d-41 | $C_3H_7-$ | — | — | — | H | H | H | H | F | H | F | H | H | H | H | H | $-C_2H_5$ |
| d-43 | $C_5H_{11}-$ | — | — | — | H | H | H | H | H | F | H | F | H | H | H | H | $-C_2H_5$ |
| d-44 | $C_2H_5OCH_2-$ | — | — | — | H | H | H | H | H | F | H | F | H | H | H | H | $-C_3H_7$ |
| d-45 | $C_2H_5OCH_2-$ | — | — | — | H | H | H | H | H | F | H | F | H | H | H | H | $-C_4H_9$ |
| d-46 | $CH_3OC_2H_4-$ | — | — | — | H | H | H | H | H | F | H | F | H | H | H | H | $-C_5H_{11}$ |
| d-47 | $CH_3OC_2H_4-$ | — | — | — | H | H | H | H | H | F | H | F | H | H | H | H | $-OC_2H_5$ |
| d-48 | $C_3H_7OCH_2-$ | — | — | — | H | H | H | H | H | F | H | F | H | H | H | H | $-C_3H_7$ |
| d-49 | $C_3H_7OCH_2-$ | — | — | — | H | H | H | H | H | F | H | F | H | H | H | H | $-C_4H_9$ |
| d-50 | $CH_3OC_3H_6-$ | — | — | — | H | H | H | H | H | F | H | F | H | H | H | H | $-C_5H_{11}$ |
| d-51 | $CH_3OC_3H_6-$ | — | — | — | H | H | H | H | H | F | H | F | H | H | H | H | $-OC_2H_5$ |
| d-52 | $CH_3O-$ | — | — | — | H | H | H | H | H | F | H | F | H | H | H | H | $-C_3H_7$ |
| d-53 | $CH_3O-$ | — | — | — | H | H | H | H | H | F | H | Cl | H | H | H | H | $-C_4H_9$ |
| d-54 | $C_2H_5O-$ | — | — | — | H | H | H | H | H | F | H | F | H | H | H | H | $-C_5H_{11}$ |
| d-55 | $C_2H_5O-$ | — | — | — | H | H | H | H | H | F | H | F | H | H | H | H | $-OC_2H_5$ |
| d-56 | $C_3H_7O-$ | — | — | — | H | H | H | H | H | F | H | F | H | H | H | H | $-C_3H_7$ |
| d-57 | $C_3H_7O-$ | — | — | — | H | H | H | H | H | F | H | F | H | H | H | H | $-C_4H_9$ |
| d-58 | $C_3H_7-$ | — | — | — | F | H | H | H | F | H | H | H | H | H | H | H | $-C_2H_5$ |
| d-59 | $C_3H_7-$ | — | — | — | F | H | H | H | H | H | H | F | H | H | H | H | $-C_2H_5$ |
| d-60 | $C_3H_7-$ | — | — | — | H | F | H | H | H | H | H | H | F | H | H | H | $-C_2H_5$ |

TABLE 12

| No. | R1 | X1 | X2 | X3 | H1 | H2 | H3 | H4 | H5 | H6 | H7 | H8 | H9 | H10 | H11 | H12 | Y1 |
|---|---|---|---|---|---|---|---|---|---|---|---|---|---|---|---|---|---|
| d-61 | $C_3H_7-$ | — | — | — | F | H | H | F | H | H | H | H | H | H | H | H | $-OC_2H_5$ |
| d-62 | $C_3H_7-$ | — | — | — | F | H | H | F | H | H | H | H | H | H | H | H | $-SC_2H_5$ |
| d-63 | $C_3H_7-$ | — | — | — | F | H | H | F | H | H | H | H | H | H | H | H | $-SiH_2C_2H_5$ |
| d-64 | $C_3H_7-$ | — | — | — | F | H | H | F | H | H | H | H | H | H | H | H | $-Si(CH_3)_2C_2H_5$ |
| d-65 | $C_3H_7-$ | — | — | — | F | H | H | F | H | H | H | H | H | H | H | H | $-CH=CH-C_2H_5$ |
| d-66 | $C_3H_7-$ | — | — | — | F | H | H | F | H | H | H | H | H | H | H | H | $-C\equiv C-C_2H_5$ |
| d-67 | $CH_2=CH-CH_2-$ | — | — | — | F | H | H | F | H | H | H | H | H | H | H | H | $-C_2H_5$ |
| d-68 | $CH_2=CH-(CH_2)_2-$ | — | — | — | F | H | H | F | H | H | H | H | H | H | H | H | $-C_2H_5$ |
| d-69 | $CH_3-CH=CH-(CH_2)_2-$ | — | — | — | F | H | H | F | H | H | H | H | H | H | H | H | $-C_2H_5$ |

EXAMPLE 8

(Use Example 1)

Liquid crystal composition B1 comprising the following compounds each in an amount shown below was prepared:

| | |
|---|---|
| 4-(4-propylcyclohexyl)benzonitrile | 24% by weight |
| 4-(4-pentylcyclohexyl)benzonitrile | 36% by weight |
| 4-(4-heptylcyclohexyl)benzonitrile | 25% by weight |
| 4-(4-propylphenyl)benzonitrile | 15% by weight |

Liquid crystal composition B1 had a clearing point of 71.7° C., value of dielectric anisotropy of 11.0, optical anisotropy of 0.137, viscosity (at 20° C.) of 26.7 mPa·s, and threshold voltage (at cell thickness of 9.2 μm) of 1.78 V.

(1) To the liquid crystal composition B1 in an amount of 95% by weight was added 5% by weight of 4-(4-methoxymethylcyclohexyl)-2'-fluoro-4"-methylterphenyl (a liquid crystalline compound of the present invention obtained in Example 1, Compound No. a-1) to prepare liquid crystal composition A1. Liquid crystal composition A1 had a clearing point of 79.1° C. (extrapolation value: 219.7° C.), value of dielectric anisotropy of 10.9 (extrapolation value: 9.0), optical anisotropy of 0.144 (extrapolation value: 0.277), viscosity (at 20° C.) of 29.3 mPa·s (extrapolation value: 76.8 mPa·s), and threshold voltage (at cell thickness of 8.9 μm) of 1.75 V. While the liquid crystal composition A1 was left in a freezer at –20° C. for 60 days, formation of crystals was not observed. Further, voltage holding ratio of the liquid crystal composition A1 was determined to find to be 99.6% at 100° C.

(2) To the liquid crystal composition B1 in an amount of 85% by weight was added 15% by weight of 4-(4-methoxymethylcyclohexyl)-2'5'-difluoro-4"-methylterphenyl (a liquid crystalline compound of the present invention obtained in Example 2, Compound No. b-1) to prepare liquid crystal composition A2. Liquid crystal composition A2 had a clearing point of 91.0° C. (extrapolation value: 200.4° C.), value of dielectric anisotropy of 10.6 (extrapolation value: 8.3), optical anisotropy of 0.155 (extrapolation value: 0.257), viscosity (at 20° C.) of 36.9 mPa·s (extrapolation value: 94.7 mPa·s), and threshold voltage (at cell thickness of 9.2 μm) of 1.93 V. While the liquid crystal composition A2 was left in a freezer at –20° C. for 60 days, formation of crystals was not observed. Further, voltage holding ratio of the liquid crystal composition A2 was determined to find to be 99.7% at 100° C.

(3) To the liquid crystal composition B1 in an amount of 95% by weight was added 5% by weight of 4-(4-propylcyclohexyl)-3-fluoro-4"-ethylterphenyl (a liquid crystalline compound of the present invention obtained in Example 3, Compound No. c-1) to prepare liquid crystal composition A3. Liquid crystal composition A3 had a clearing point of 79.5° C. (extrapolation value: 227.7° C.), value of dielectric anisotropy of 10.7 (extrapolation value: 5.0), optical anisotropy of 0.144 (extrapolation value: 0.277), viscosity (at 20° C.) of 28.5 mPa·s (extrapolation value: 64.6 mPa·s), and threshold voltage (at cell thickness of 8.7 μm) of 1.77 V. While the liquid crystal composition A3 was left in a freezer at −20° C. for 60 days, formation of crystals was not observed. Further, voltage holding ratio of the liquid crystal composition A3 was determined to find to be 99.6% at 100° C.

(4) To the liquid crystal composition B1 in an amount of 85% by weight was added 15% by weight of 4-(4-propylcyclohexyl)-2,5-difluoro-4"-ethylterphenyl (a liquid crystalline compound of the present invention obtained in Example 4, Compound No. d-1) to prepare liquid crystal composition A4. Liquid crystal composition A4 had a clearing point of 93.0° C. (extrapolation value: 213.7° C.), value of dielectric anisotropy of 10.1 (extrapolation value: 5.0), optical anisotropy of 0.155 (extrapolation value: 0.257), viscosity (at 20° C.) 35.0 mPa·s (extrapolation value: 81.5 mPa·s), and threshold voltage (at cell thickness of 8.8 μm) of 1.90 V. While the liquid crystal composition A4 was left in a freezer at −20° C. for 60 days, formation of crystals was not observed. Further, voltage holding ratio of the liquid crystal composition A4 was determined to find to be 99.7% at 100° C.

EXAMPLE 9

To the liquid crystal composition B1 described above (85% by weight) was mixed the liquid crystalline compound (Compound No. d-1, 15% by weight) to prepare a liquid crystal composition. While this composition was left in a freezer at −20° C., crystals were not formed and a smectic phase was not exhibited in 60 days.

On the other hand, 4-(4-propylcyclohexyl)-4"-ethylterphenyl (15% by weight) synthesized according to the method described in Laid-open Japanese Patent Publication No. Sho 58-203,922 was added to the liquid crystal composition B1 described above (85% by weight) to prepare a liquid crystal composition. When this composition was also left in a freezer at −20° C., crystals were formed in 1 hour.

Further, the 4-(4-propylcyclohexyl)-4"-ethylterphenyl mentioned above (5% by weight) was added to the liquid crystal composition B1 described above (95% by weight) to prepare another liquid crystal composition. When this composition was left in a freezer at −20° C., crystals were formed in 3 days.

Results of Example 9 are summarized in Table 13 below.

TABLE 13

| Added compound | Stability of liquid crystal composition |
| --- | --- |
| 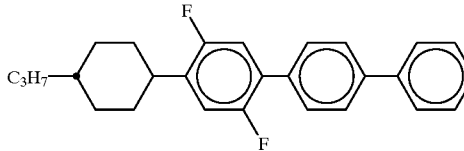<br>Compound No. d-1 | Even when the compound was mixed. in 15% wt. crystals were not formed and a smectic phase was not exhibited in 60 days. |
| 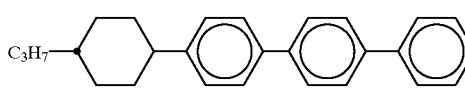<br>Laid-open Japanese Patent Publication No. Sho 58-203,922 | When the compound was mixed in 15% wt., crystals were formed in 1 hour. When 5% wt., crystals were formed in 3 days. |

EXAMPLE 10

Nematic temperature range of liquid crystalline compounds, Compound Nos. c-1 and d-1 of the present invention obtained in Examples 3 and 4, respectively, and 4-(4-pentylcyclohexyl)-3'-fluoro-4"-propylterphenyl described in Laid-open Japanese Patent Publication No. Hei 2-237,949 (JP '949) was determined to find that whereas the nematic temperature range of Compound Nos. c-1 and d-1 were as wide as 129.3° C. and 164.4° C., respectively, that of JP '949 was as narrow as 43° C.

TABLE 14

| Added compound | Phase transition temperature (° C.) |
|---|---|
| Compound No. c-1 (C₃H₇–cyclohexyl–C₆H₃(F)–C₆H₄–C₆H₄–C₂H₅) | C →156.2 S →188.6 N →317.9 I |
| Compound No. d-1 (C₃H₇–cyclohexyl–C₆H₂(F)(F)–C₆H₄–C₆H₄–C₂H₅) | C →122.2 N →286.6 I |
| Laid-open Japanese Patent Publication No. Hei 2-237,949 (C₅H₁₁–cyclohexyl–C₆H₄–C₆H₄–C₆H₃(F)–C₃H₇) | C →66 S →242 N →285 I |

As nematic liquid crystal compositions comprising the liquid crystalline compounds of the present invention, the following examples can be mentioned. In this connection, compounds described in the following examples are indicated by symbols according to the rules shown in Table 15 below. In the followings, "%" indicating the amount of each compound in each liquid crystal composition means "% by weight".

TABLE 15

| Left side terminal group | Symbol | Bonding group | Symbol |
|---|---|---|---|
| $C_aH_{2a+1}$— | a— | —$CH_2CH_2$— | 2 |
| $C_aH_{2a+1}O$— | aO— | —COO— | E |
| $C_aH_{2a+1}OC_bH_{2b}$— | aOb— | —C≡C— | T |
| $CH_2$=$CHC_aH_{2a}$— | Va— | —CH=CH— | V |
| $C_aH_{2a+1}CH$=$CHC_bH_{2b}$— | aVb— | —$CF_2O$— | CF2O |
| $C_aH_{2a+1}CH$=$CHC_bH_{2b}CH$=$CHC_dH_{2d}$— | aVbVc— | | |

| Ring struature —(An)— | Symbol | Right side terminal group | Symbol |
|---|---|---|---|
| 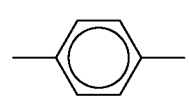 | B | —F | —F |
| 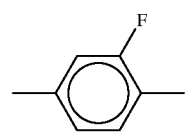 | B(F) | —Cl | —CL |
| 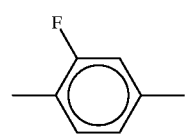 | B(2F) | —CN | —C |

TABLE 15-continued
| Structure | Symbol | R | R' |
|---|---|---|---|
| [2,3-difluorophenyl] | B(2F,3F) | —CF3 | —CF3 |
| [3,5-difluorophenyl] | B(F,F) | —OCF3 | —OCF3 |
| [2-chlorophenyl] | B(CL) | —OCF2H | —OCF2H |
| [cyclohexyl] | H | —C$_w$H$_{2w+1}$ | —w |
| [pyrimidinyl] | Py | —OC$_w$H$_{2w+1}$ | —Ow |
| [dioxanyl] | D | —COOCH$_3$ | —EMe |
| [cyclohexenyl] | Ch | | |
Examples of designation
Example 1
3-H2B(F,F)B(F)-F
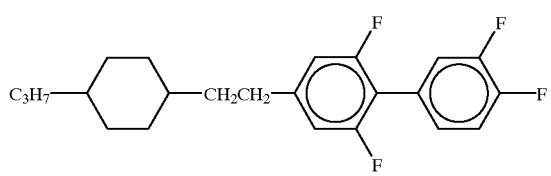
Example 2
3-HB(F)TB-2
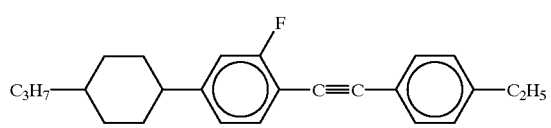

TABLE 15-continued

Example 3

1V2-BEB(F,F)-C

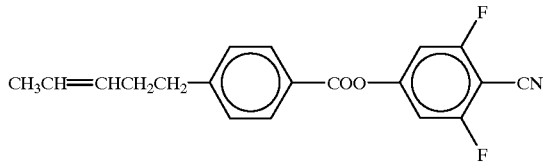

EXAMPLE 11

| | |
|---|---|
| 1O1-HBB(2F)B-1 (Compound No. a-1) | 3.0% |
| 1O1-HBB(2F,5F)B-1 (Compound No. b-1) | 5.0% |
| 1V2-BEB(F,F)-C | 5.0% |
| 3-HB-C | 25.0% |
| 3-HB-O2 | 4.0% |
| 1-BTB-3 | 5.0% |
| 2-BTB-1 | 10.0% |
| 3-HH-4 | 11.0% |
| 3-HHB-1 | 9.0% |
| 3-HHB-3 | 7.0% |
| 3-H2BTB-2 | 4.0% |
| 3-H2BTB-3 | 4.0% |
| 3-HB(F)TB-2 | 6.0% |
| 3-HB(F)TB-3 | 2.0% |

Physical properties of this liquid crystal composition were as follows:

$T_{NI}$=90.7 (° C.)

$\eta$=18.7 (mPa·s)

$\Delta n$=0.161

$\Delta \epsilon$=7.3

$V_{th}$=2.05 (V)

EXAMPLE 12

| | |
|---|---|
| 3-HB(2F)BB-2 (Compound No. c-1) | 3.0% |
| 3-HB(2F,5F)BB-2 (Compound No. d-1) | 5.0% |
| V2-HB-C | 12.0% |
| 1V2-HB-C | 12.0% |
| 3-HB-C | 24.0% |
| 3-HB(F)-C | 5.0% |
| 3-HB-O2 | 5.0% |
| 2-BTB-1 | 2.0% |
| 3-HH-4 | 8.0% |
| 3-HHV(F)-F | 6.0% |
| 2-HHB-C | 3.0% |
| 3-HHB-C | 6.0% |
| 3-HB(F)TB-2 | 5.0% |
| 3-H2BTB-4 | 4.0% |

Physical properties of this liquid crystal composition were as follows:

$T_{NI}$=87.0 (° C.)

$\eta$=20.1 (mPa·s)

$\Delta n$=0.144

$\Delta \epsilon$=8.7

$V_{th}$=2.00 (V)

EXAMPLE 13

| | |
|---|---|
| 5-HBB(F,F)B-2 (Compound No. d-43) | 3.0% |
| 2O1-BEB(F)-C | 5.0% |
| 3O1-BEB(F)-C | 15.0% |
| 4O1-BEB(F)-C | 13.0% |
| 5O1-BEB(F)-C | 13.0% |
| 3-HB(F)-C | 3.0% |
| 2-HHB(F)-C | 15.0% |
| 3-HHB(F)-C | 12.0% |
| 3-HB(F)TB-2 | 4.0% |
| 3-HB(F)TB-3 | 4.0% |
| 3-HB(F)TB-4 | 4.0% |
| 3-HHB-1 | 5.0% |
| 3-HHB-O1 | 4.0% |

Physical properties of this liquid crystal composition were as follows:

$T_{NI}$=88.6 (° C.)

$\eta$=85.2 (mPa·s)

$\Delta n$=0.151

$\Delta \epsilon$=31.3

$V_{th}$=0.88 (V)

EXAMPLE 14

| | |
|---|---|
| 1O1-HBB(2F,5F)B-1 (Compound No. b-1) | 10.0% |
| 5-PyB-F | 4.0% |
| 3-PyB(F)-F | 4.0% |
| 2-BB-C | 5.0% |
| 4-BB-C | 4.0% |
| 5-BB-C | 5.0% |
| 2-PyB-2 | 2.0% |
| 3-PyB-2 | 2.0% |
| 4-PyB-2 | 2.0% |
| 6-PyB-O5 | 3.0% |
| 6-PyB-O6 | 3.0% |
| 6-PyB-O7 | 3.0% |
| 6-PyB-O8 | 3.0% |
| 3-PyBB-F | 6.0% |
| 4-PyBB-F | 6.0% |
| 5-PyBB-F | 6.0% |
| 3-HB-O2 | 5.0% |
| 3-HHB-1 | 6.0% |
| 3-HHB-3 | 3.0% |
| 2-H2BTB-2 | 4.0% |
| 2-H2BTB-3 | 4.0% |
| 3-H2BTB-3 | 5.0% |
| 3-H2BTB-4 | 5.0% |

Physical properties of this liquid crystal composition were as follows:

$T_{NI}$=94.4 (° C.)

$\eta$=41.3 (mPa·s)

$\Delta n$=0.200

$\Delta \epsilon$=6.8

$V_{th}$=2.30 (V)

EXAMPLE 15

| | |
|---|---|
| 1O1-HBB(2F)B-1 (Compound No. a-1) | 3.0% |
| 3-DB-C | 10.0% |
| 4-DB-C | 10.0% |
| 2-BEB-C | 12.0% |
| 3-BEB-C | 4.0% |
| 3-PyB(F)-F | 6.0% |
| 3-HEB-O4 | 8.0% |
| 4-HEB-O2 | 6.0% |
| 5-HEB-O1 | 6.0% |
| 3-HEB-O2 | 5.0% |
| 5-HEB-O2 | 4.0% |
| 5-HEB-5 | 5.0% |
| 4-HEB-5 | 5.0% |
| 1O-BEB-2 | 4.0% |
| 3-HHB-1 | 6.0% |
| 3-HHEBB-C | 3.0% |
| 3-HBEBB-C | 3.0% |

Physical properties of this liquid crystal composition were as follows:

$T_{NI}$=68.3 (° C.)
$\eta$=38.1 (mPa·s)
$\Delta n$=0.121
$\Delta\epsilon$=11.2
$V_{th}$=1.33 (V)

EXAMPLE 16

| | |
|---|---|
| 3-HB(2F)BB-2 (Compound No. c-1) | 4.0% |
| 3-HB-C | 21.0% |
| 7-HB-C | 3.0% |
| 1O1-HB-C | 10.0% |
| 3-HB(F)-C | 10.0% |
| 2-PyB-2 | 2.0% |
| 3-PyB-2 | 2.0% |
| 4-PyB-2 | 2.0% |
| 1O1-HH-3 | 7.0% |
| 2-BTB-O1 | 7.0% |
| 3-HHB-F | 4.0% |
| 3-HHB-O1 | 4.0% |
| 3-HHB-3 | 8.0% |
| 3-H2BTB-2 | 3.0% |
| 3-H2BTB-3 | 3.0% |
| 2-PyBH-3 | 4.0% |
| 3-PyBH-3 | 3.0% |
| 3-PyBB-2 | 3.0% |

Physical properties of this liquid crystal composition were as follows:

$T_{NI}$=79.1 (° C.)
$\eta$=19.0 (mPa·s)
$\Delta n$=0.142
$\Delta\epsilon$=8.4
$V_{th}$=1.72 (V)

EXAMPLE 17

| | |
|---|---|
| 1O1-HBB(2F,5F)B-1 (Compound No. b-1) | 5.0% |
| 3-HB(2F)BB-2 (Compound No. c-1) | 3.0% |
| 2O1-BEB(F)-C | 5.0% |
| 3O1-BEB(F)-C | 12.0% |
| 5O1-BEB(F)-C | 4.0% |
| 1V2-BEB(F,F)-C | 10.0% |
| 3-HHE-1 | 10.0% |

-continued

| | |
|---|---|
| 3-HB-O2 | 21.0% |
| 3-HHEB-F | 3.0% |
| 5-HHEB-F | 3.0% |
| 3-HBEB-F | 4.0% |
| 2O1-HBE(F)-C | 2.0% |
| 3-HB(F)EB(F)-C | 2.0% |
| 3-HBEB(F,F)-C | 2.0% |
| 2-HHB-F | 4.0% |
| 3-HHB-O1 | 4.0% |
| 3-HHB-3 | 2.0% |
| 3-BEBEB-F | 2.0% |
| 3-BEBEB-1 | 2.0% |

Physical properties of this liquid crystal composition were as follows:

$T_{NI}$=79.4 (° C.)
$\eta$=40.1 (mPa·s)
$\Delta n$=0.122
$\Delta\epsilon$=23.7
$V_{th}$=0.97 (V)

EXAMPLE 18

| | |
|---|---|
| 3-HB(2F)BB-2 (Compound No. c-1) | 4.0% |
| 5-BEB(F)-C | 5.0% |
| V-HB-C | 11.0% |
| 5-PyB-C | 6.0% |
| 4-BB-3 | 11.0% |
| 3-HH-2V | 10.0% |
| 5-HH-V | 11.0% |
| V-HHB-1 | 7.0% |
| V2-HHB-1 | 15.0% |
| 3-HHB-1 | 5.0% |
| 1V2-HBB-2 | 10.0% |
| 3-HHEBH-3 | 5.0% |

Physical properties of this liquid crystal composition were as follows:

$T_{NI}$=94.7 (° C.)
$\eta$=17.3 (mPa·s)
$\Delta n$=0.121
$\Delta\epsilon$=4.8
$V_{th}$=2.36 (V)

EXAMPLE 19

| | |
|---|---|
| 5-HB(F,F)BB-2 (Compound No. d-25) | 4.0% |
| 2O1-BEB(F)-C | 5.0% |
| 3O1-BEB(F)-C | 12.0% |
| 5O1-BEB(F)-C | 4.0% |
| 1V2-BEB(F,F)-C | 16.0% |
| 3-HB-O2 | 10.0% |
| 3-HH-4 | 3.0% |
| 3-HHB-F | 3.0% |
| 3-HHB-1 | 8.0% |
| 3-HHB-O1 | 4.0% |
| 3-HBEB-F | 4.0% |
| 3-HHEB-F | 7.0% |
| 5-HHEB-F | 3.0% |
| 3-H2BTB-2 | 4.0% |
| 3-H2BTB-3 | 4.0% |
| 3-H2BTB-4 | 4.0% |
| 3-HB(F)TB-2 | 5.0% |

Physical properties of this liquid crystal composition were as follows:

$T_{NI}$=92.0 (° C.)
η=41.9 (mPa·s)
Δn=0.147
Δε=28.4
$V_{th}$=0.99 (V)

EXAMPLE 20

| | |
|---|---|
| 3-HB(2F,5F)BB-2 (Compound No. d-1) | 5.0% |
| 2-BEB-C | 12.0% |
| 3-BEB-C | 4.0% |
| 4-BEB-C | 6.0% |
| 3-HB-C | 30.0% |
| 3-HEB-O4 | 12.0% |
| 4-HEB-O2 | 8.0% |
| 5-HEB-O1 | 8.0% |
| 3-HEB-O2 | 6.0% |
| 5-HEB-O2 | 5.0% |
| 3-HHB-O1 | 4.0% |

Physical properties of this liquid crystal composition were as follows:

$T_{NI}$=63.8 (° C.)
η=29.0 (mPa·s)
Δn=0.120
Δε=10.3
$V_{th}$=1.31 (V)

EXAMPLE 21

| | |
|---|---|
| 1O1-HBB(2F)B-1 (Compound No. a-1) | 4.0% |
| 3-HB(2F)BB-2 (Compound No. c-1) | 4.0% |
| 2-BEB-C | 10.0% |
| 5-BB-C | 12.0% |
| 7-BB-C | 7.0% |
| 3-HB-C | 5.0% |
| 1-BTB-3 | 7.0% |
| 2-BTB-1 | 10.0% |
| 1O-BEB-2 | 10.0% |
| 1O-BEB-5 | 12.0% |
| 2-HHB-1 | 4.0% |
| 3-HHB-F | 4.0% |
| 3-HHB-1 | 7.0% |
| 3-HHB-O1 | 4.0% |

Physical properties of this liquid crystal composition were as follows:

$T_{NI}$=70.1 (° C.)
η=24.3 (mPa·s)
Δn=0.171
Δε=6.8
$V_{th}$=1.72 (V)

EXAMPLE 22

| | |
|---|---|
| 1O1-HBB(2F,5F)B-1 (Compound No. b-1) | 12.0% |
| 3-HB(2F,5F)BB-2 (Compound No. d-1) | 6.0% |
| 1V2-BEB(F,F)-C | 5.0% |
| 3-HB-C | 25.0% |
| 1-BTB-3 | 5.0% |
| 2-BTB-1 | 10.0% |
| 3-HH-4 | 11.0% |
| 3-HHB-1 | 11.0% |
| 3-HHB-3 | 9.0% |
| 3-HB-O2 | 6.0% |

Physical properties of this liquid crystal composition were as follows:

$T_{NI}$=92.2 (° C.)
η=24.1 (mPa·s)
Δn=0.220
Δε=7.0
$V_{th}$=2.12 (V)

EXAMPLE 23

| | |
|---|---|
| 1O1-HHB(2F,5F)B-1 (Compound No. b-1) | 10.0% |
| 5-HB(F,F)BB-2 (Compound No. d-25) | 4.0% |
| 2O1-BEB(F)-C | 5.0% |
| 3O1-BEB(F)-C | 15.0% |
| 4O1-BEB(F)-C | 13.0% |
| 5O1-BEB(F)-C | 13.0% |
| 3-HB-C | 10.0% |
| 2-HHB(F)-C | 15.0% |
| 3-HHB(F)-C | 3.0% |
| 3-HB(F)TB-2 | 4.0% |
| 3-HB(F)TB-3 | 4.0% |
| 3-HB(F)TB-4 | 4.0% |

Physical properties of this liquid crystal composition were as follows:

$T_{NI}$=85.8 (° C.)
η=92.0 (mPa·s)
Δn=0.162
Δε=31.2
$V_{th}$=0.84 (V)

EXAMPLE 24

| | |
|---|---|
| 1O1-HBB(2F)B-1 (Compound No. a-1) | 2.0% |
| 3-HB(2F,5F)BB-2 (Compound No. d-1) | 5.0% |
| 7-HB(F)-F | 5.0% |
| 2-HHB(F)-F | 17.0% |
| 3-HHB(F)-F | 17.0% |
| 5-HHB(F)-F | 16.0% |
| 2-H2HB(F)-F | 5.0% |
| 3-H2HB(F)-F | 5.0% |
| 2-HBB(F)-F | 6.0% |
| 3-HBB(F)-F | 6.0% |
| 5-HBB(F)-F | 13.0% |
| 3-HB-O2 | 3.0% |

Physical properties of this liquid crystal composition were as follows:

$T_{NI}$=102.1 (° C.)
η=29.5 (mPa·s)
Δn=0.102
Δε=5.0
$V_{th}$=2.22 (V)

EXAMPLE 25

| | |
|---|---|
| 1O1-HBB(2F)B-1 (Compound No. a-1) | 2.0% |
| 5-HB(F,F)BB-2 (Compound No. d-25) | 2.0% |
| 7-HB(F)-F | 10.0% |
| 5-H2B(F)-F | 5.0% |
| 3-HB-O2 | 10.0% |
| 3-HH-4 | 5.0% |
| 2-HHB(F)-F | 10.0% |
| 3-HHB(F)-F | 10.0% |
| 5-HHB(F)-F | 5.0% |
| 3-H2HB(F)-F | 5.0% |
| 2-HBB(F)-F | 3.0% |
| 3-HBB(F)-F | 3.0% |
| 5-HBB(F)-F | 6.0% |
| 2-H2BB(F)-F | 5.0% |
| 3-H2BB(F)-F | 6.0% |
| 3-HHB-1 | 8.0% |
| 3-HHB-O1 | 5.0% |

Physical properties of this liquid crystal composition were as follows:

$T_{NI}$=84.3 (° C.)

$\eta$=19.5 (mPa·s)

$\Delta n$=0.094

$\Delta \epsilon$=3.4

$V_{th}$=2.63 (V)

EXAMPLE 26

| | |
|---|---|
| 3-HB(2F)BB-2 (Compound No. c-1) | 2.0% |
| 5-HB(F,F)BB-2 (Compound No. d-25) | 2.0% |
| 7-HB(F,F)-F | 6.0% |
| 3-HB-O2 | 7.0% |
| 2-HHB(F)-F | 10.0% |
| 3-HHB(F)-F | 10.0% |
| 5-HHB(F)-F | 3.0% |
| 2-HBB(F)-F | 9.0% |
| 3-HBB(F)-F | 9.0% |
| 5-HBB(F)-F | 16.0% |
| 2-HBB-F | 4.0% |
| 3-HBB-F | 4.0% |
| 5-HBB-F | 3.0% |
| 3-HBB(F,F)-F | 5.0% |
| 5-HBB(F,F)-F | 10.0% |

Physical properties of this liquid crystal composition were as follows:

$T_{NI}$=81.4 (° C.)

$\eta$=26.0 (mPa·s)

$\Delta n$=0.118

$\Delta \epsilon$=5.8

$V_{th}$=1.99 (V)

EXAMPLE 27

| | |
|---|---|
| 1O1-HBB(2F,5F)B-1 (Compound No. b-1) | 4.0% |
| 7-HB(F,F)-F | 7.0% |
| 3-H2HB(F1F)-F | 12.0% |
| 4-H2HB(F1F)-F | 10.0% |
| 5-H2HB(F,F)-F | 10.0% |
| 3-HHB(F1F)-F | 10.0% |
| 4-HHB(F,F)-F | 5.0% |
| 3-HH2B(F,F)-F | 15.0% |
| 5-HH2B(F,F)-F | 3.0% |
| 3-HBB(F,F)-F | 12.0% |
| 5-HBB(F,F)-F | 12.0% |

Physical properties of this liquid crystal composition were as follows:

$T_{NI}$=73.2 (° C.)

$\eta$=29.2 (mPa·s)

$\Delta n$=0.090

$\Delta \epsilon$=8.6

$V_{th}$=1.59 (V)

EXAMPLE 28

| | |
|---|---|
| 1O1-HBB(2F,5F)B-1 (Compound No. b-1) | 4.0% |
| 7-HB(F,F)-F | 8.0% |
| 3-H2HB(F,F)-F | 12.0% |
| 4-H2HB(F,F)-F | 10.0% |
| 3-HHB(F,F)-F | 10.0% |
| 4-HHB(F,F)-F | 5.0% |
| 3-HBB(F,F)-F | 10.0% |
| 3-HHEB(F,F)-F | 3.0% |
| 4-HHEB(F,F)-F | 3.0% |
| 5-HHEB(F,F)-F | 3.0% |
| 2-HBEB(F,F)-F | 3.0% |
| 3-HBEB(F,F)-F | 5.0% |
| 5-HBEB(F,F)-F | 3.0% |
| 3-HDB(F,F)-F | 15.0% |
| 3-HHBB(F,F)-F | 6.0% |

Physical properties of this liquid crystal composition were as follows:

$T_{NI}$=76.5 (° C.)

$\eta$=34.7 (mPa·s)

$\Delta n$=0.090

$\Delta \epsilon$=12.9

$V_{th}$=1.41 (V)

EXAMPLE 29

| | |
|---|---|
| 1O1-HBB(2F,5F)B-1 (Compound No. b-1) | 4.0% |
| 5-HB(F,F)BB-2 (Compound No. d-25) | 2.0% |
| 3-HB-CL | 10.0% |
| 5-HB-CL | 4.0% |
| 7-HB-CL | 4.0% |
| 3-HB-O2 | 2.0% |
| 1O1-HH-5 | 5.0% |
| 2-HBB(F)-F | 8.0% |
| 3-HBB(F)-F | 8.0% |
| 5-HBB(F)-F | 14.0% |
| 4-HHB-CL | 8.0% |
| 3-H2HB(F)-CL | 4.0% |
| 3-HBB(F,F)-F | 10.0% |
| 5-H2BB(F,F)-F | 9.0% |
| 3-HB(F)-VB-2 | 4.0% |
| 3-HB(F)-VB-3 | 4.0% |

Physical properties of this liquid crystal composition were as follows:

$T_{NI}$=91.0 (° C.)

$\eta$=22.1 (mPa·s)

$\Delta n$=0.135

$\Delta \epsilon$=5.0

$V_{th}$=2.29 (V)

EXAMPLE 30

| | |
|---|---|
| 3-HB(2F,5F)BB-2 (Compound No. d-1) | 5.0% |
| 7-HB(F,F)-F | 5.0% |
| 3-HHB(F,F)-F | 9.0% |
| 3-H2HB(F,F)-F | 8.0% |
| 4-H2HB(F,F)-F | 6.0% |
| 3-HBB(F,F)-F | 21.0% |
| 5-HBB(F,F)-F | 20.0% |
| 3-H2BB(F,F)-F | 10.0% |
| 5-HHBB(F,F)-F | 3.0% |
| 5-HHEBB-F | 2.0% |
| 3-HH2BB(F,F)-F | 3.0% |
| 1O1-HBBH-4 | 4.0% |
| 1O1-HBBH-5 | 4.0% |

Physical properties of this liquid crystal composition were as follows:

$T_{NI}$=98.5 (° C.)
$\eta$=35.1 (mPa·s)
$\Delta n$=0.120
$\Delta\epsilon$=8.5
$V_{th}$=1.70 (V)

EXAMPLE 31

| | |
|---|---|
| 5-HBB(F,F)B-2 (Compound No. d-43) | 2.0% |
| 3-HB(2F,5F)BB-2 (Compound No. d-1) | 2.0% |
| 5-HB-F | 12.0% |
| 6-HB-F | 9.0% |
| 7-HB-F | 7.0% |
| 7-HB(F)-F | 3.0% |
| 2-HHB-OCF3 | 7.0% |
| 3-HHB-OCF3 | 11.0% |
| 4-HHB-OCF3 | 7.0% |
| 5-HHB-OCF3 | 5.0% |
| 3-HH2B-OCF3 | 4.0% |
| 5-HH2B-OCF3 | 4.0% |
| 3-HHB(F,F)-OCF3 | 5.0% |
| 3-HBB(F)-F | 10.0% |
| 5-HBB(F)-F | 3.0% |
| 3-HH2B(F)-F | 3.0% |
| 3-HB(F)BH-3 | 3.0% |
| 5-HBBH-3 | 3.0% |

Physical properties of this liquid crystal composition were as follows:

$T_{NI}$=87.3 (° C.)
$\eta$=14.8 (mPa·s)
$\Delta n$=0.091
$\Delta\epsilon$=4.6
$V_{th}$=2.38 (V)

EXAMPLE 32

| | |
|---|---|
| 3-HB(2F)BB-2 (Compound No. c-1) | 2.0% |
| 1O1-HBB(2F,5F)B-1 (Compound No. b-1) | 2.0% |
| 5-H4HB(F,F)-F | 7.0% |
| 5-H4HB-OCF3 | 15.0% |
| 3-H4HB(F,F)-CF3 | 8.0% |
| 5-H4HB(F,F)-CF3 | 10.0% |
| 3-HB-CL | 6.0% |
| 5-HB-CL | 7.0% |
| 2-H2BB(F)-F | 5.0% |
| 3-H2BB(F)-F | 3.0% |

-continued

| | |
|---|---|
| 5-HVHB(F,F)-F | 5.0% |
| 3-HHB-OCF3 | 5.0% |
| 3-H2HB-OCF3 | 5.0% |
| V-HHB(F)-F | 5.0% |
| 3-HChB(F)-F | 5.0% |
| 5-HHEB-OCF3 | 2.0% |
| 3-HBEB(F,F)-F | 5.0% |
| 5-HHV2-F | 3.0% |

Physical properties of this liquid crystal composition were as follows:

$T_{NI}$=74.6 (° C.)
$\eta$=24.3 (mPa·s)
$\Delta n$=0.093
$\Delta\epsilon$=8.1
$V_{th}$=1.77 (V)

EXAMPLE 33

| | |
|---|---|
| 1O1-HBB(2F,5F)B-1 (compound No. b-1) | 4.0% |
| 3-HB(2F,5F)BB-2 (Compound No. d-1) | 6.0% |
| 2-HHB(F)-F | 2.0% |
| 3-HHB(F)-F | 2.0% |
| 5-HHB(F)-F | 2.0% |
| 2-HBB(F)-F | 6.0% |
| 3-HBB(F)-F | 6.0% |
| 5-HBB(F)-F | 10.0% |
| 2-H2BB(F)-F | 9.0% |
| 3-H2BB(F)-F | 9.0% |
| 7-HB(F,F)-F | 7.0% |
| 3-HBB(F,F)-F | 25.0% |
| 5-HBB(F,F)-F | 7.0% |
| 1O1-HBBH-4 | 5.0% |

Physical properties of this liquid crystal composition were as follows:

$T_{NI}$=96.8 (° C.)
$\eta$=36.6 (mPa·s)
$\Delta n$=0.145
$\Delta\epsilon$=7.1
$V_{th}$=2.01 (V)

EXAMPLE 34

| | |
|---|---|
| 1O1-HBB(2F)B-1 (Compound No. a-1) | 2.0% |
| 1O1-HBB(2F(5F)B-1 (Compound No. b-1) | 4.0% |
| 3-HB(2F,5F)BB-2 (Compound No. d-1) | 6.0% |
| 5-HB(F,F)BB-2 (Compound No. d-25) | 2.0% |
| 7-HB(F,F)-F | 15.0% |
| 3-H2HB(F,F)-F | 12.0% |
| 4-H2HB(F,F)-F | 10.0% |
| 3-HHB(F,F)-F | 10.0% |
| 4-HHB(F,F)-F | 5.0% |
| 5-HH2B(F,F)-F | 10.0% |
| 3-HBB(F,F)-F | 12.0% |
| 5-HBB(F,F)-F | 12.0% |

Physical properties of this liquid crystal composition were as follows:

$T_{NI}$=75.7 (° C.)
$\eta$=30.1 (mPa·s)
$\Delta n$=0.087
$\Delta\epsilon$=8.0
$V_{th}$=1.70 (V)

EXAMPLE 35

| | |
|---|---|
| 3-HB(2F)BB-2 (Compound No. c-1) | 2.0% |
| 5-HBB(F,F)B-2 (Compound No. d-43) | 2.0% |
| 2-HHB(F)-F | 3.0% |
| 3-HHB(F)-F | 2.0% |
| 5-HHB(F)-F | 2.0% |
| 2-HBB(F)-F | 6.0% |
| 3-HBB(F)-F | 6.0% |
| 5-HBB(F)-F | 10.0% |
| 2-H2BB(F)-F | 9.0% |
| 3-H2BB(F)-F | 9.0% |
| 3-HBB(F,F)-F | 25.0% |
| 5-HBB(F,F)-F | 19.0% |
| 1O1-HBBH-4 | 5.0% |

Physical properties of this liquid crystal composition were as follows:

$T_{NI}$=93.2 (° C.)
η=35.0 (mPa·s)
Δn=0.135
Δε=7.4
$V_{th}$=1.93 (V)

INDUSTRIAL APPLICABILITY

Liquid crystalline compounds of the present invention have simultaneously a wide temperature range of a nematic phase, high miscibility with other liquid crystalline compounds at low temperatures, high optical anisotropy, and high chemical stability. As demonstrated in Examples of composition, preparation of liquid crystal compositions having excellent properties, that is, a wide range of driving temperature compared with that of conventional liquid crystal compositions has become possible by using the liquid crystalline compounds of the present invention.

What is claimed is:

1. A tetracyclic compound expressed by the following general formula (1)

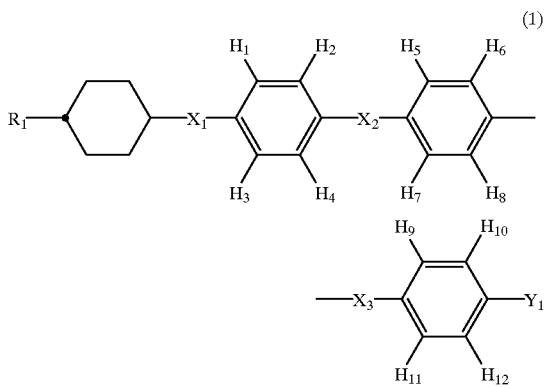

(1)

wherein each of $H_1$ to $H_{12}$ represents hydrogen atom, at least one of $H_1$ to $H_{12}$ is replaced by a halogen atom, and when either $H_6$ or $H_8$ is replaced by a halogen atom, at least one of the remaining hydrogen atoms is replaced by a halogen atom; $R_1$ and $Y_1$ independently represent an alkyl group, alkoxy group, or alkoxyalkyl group having 1 to 20 carbon atoms, or an alkenyl group having 2 to 20 carbon atoms, one or more methylene groups in $R_1$ or $Y_1$ may be replaced by oxygen atom, sulfur atom, dihydrosilylene group, dimethylsilylene group, —CH=CH—, or —C≡C—; and each of $X_1$, $X_2$, and $X_3$ independently represents a covalent bond, 1,2-ethylene group, or 1,4-butylene group; with the proviso that when $H_5$, both of $H_2$ and $H_6$, or both of $H_5$ and $H_8$ are replaced by a halogen atom, in no case $R_1$ and $Y_1$ are simultaneously an alkyl group having 1 to 20 carbon atoms, with the further proviso that when $H_2$ is a halogen atom, $H_1$ and $H_3$ to $H_{12}$ are all hydrogen atoms, and $X_1$ is 1,2-ethylene group, or when $H_6$ is a halogen atom, $H_1$ to $H_5$ and $H_7$ to $H_{12}$ are all hydrogen atoms, and $X_1$ is 1,2-ethylene group, or when $H_9$ is a halogen atom, $H_1$ to $H_8$ and $H_{10}$ to $H_{12}$ are all hydrogen atoms, and $X_1$ is 1,2-ethylene group, or when $H_2$ is a halogen atom, $H_1$ and $H_3$ to $H_{12}$ are all hydrogen atoms, and $X_1$ to $X_3$ are all covalent bonds, then $R_1$ and $Y_1$ are not an alkyl group or alkoxy group, and with the further proviso that all of $H_1$ to $H_4$, or all of $H_5$ to $H_8$, or all of $H_9$ to $H_{12}$ can not be halogen atoms.

2. The tetracyclic compound according to claim 1 wherein hydrogen atom of $H_1$ and $H_4$ are replaced by a halogen atom, and each of $H_2$, $H_3$, and $H_5$ to $H_{12}$ represents hydrogen atom.

3. The tetracyclic compound according to claim 1 wherein hydrogen atom of $H_1$ is replaced by a halogen atom, and each of $H_2$ to $H_{12}$ represents hydrogen atom.

4. The tetracyclic compound according to claim 1 wherein hydrogen atom of $H_5$ is replaced by a halogen atom, and each of $H_1$ to $H_4$, and $H_6$ to $H_{12}$ represents hydrogen atom.

5. The tetracyclic compound according to claim 1 wherein hydrogen atom of $H_6$ and $H_8$ are replaced by a halogen atom, and each of $H_1$ to $H_5$, $H_7$, and $H_9$ to $H_{12}$ represents hydrogen atom.

6. The tetracyclic compound according to claim 1 wherein hydrogen atom of $H_1$ and $H_5$ are replaced by a halogen atom, and each of $H_2$ to $H_4$, and $H_6$ to $H_{12}$ represents hydrogen atom.

7. The tetracyclic compound according to claim 1 wherein hydrogen atom of $H_1$ and $H_9$ are replaced by a halogen atom, and each of $H_2$ to $H_8$, and $H_{10}$ to $H_{12}$ represents hydrogen atom.

8. The tetracyclic compound according to claim 1 wherein hydrogen atom of $H_2$ and $H_9$ are replaced by a halogen atom, and each of $H_1$, $H_3$ to $H_8$, and $H_{10}$ to $H_{12}$ represents hydrogen atom.

9. The tetracyclic compound according to claim 1 wherein hydrogen atom of $H_2$ and $H_4$ are replaced by a halogen atom, and each of $H_1$, $H_3$, and $H_5$ to $H_{12}$ represents hydrogen atom.

10. A liquid crystal composition comprising at least two components, at least one of which is a tetracyclic compound defined in any one of claims 1–9.

11. A liquid crystal composition comprising, as a first component, at least one tetracyclic compound defined in any one of claims 1–9, and comprising, as a second component, at least one compound selected from the group consisting of the compounds expressed by any one of the general formulas (2), (3), and (4)

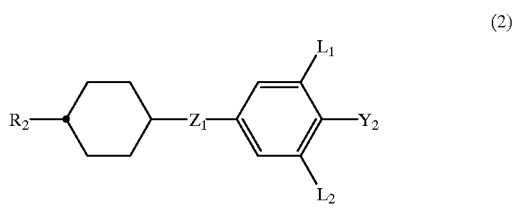

(2)

(3)

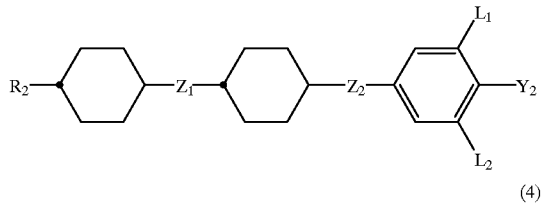

(4)

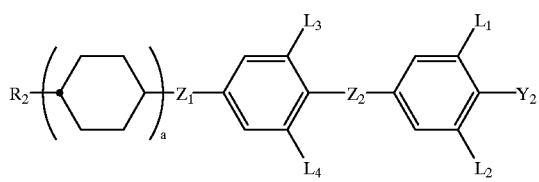

wherein $R_2$ represents an alkyl group having 1 to 10 carbon atoms; $Y_2$ represents fluorine atom, chlorine atom, $OCF_3$, $OCF_2H$, $CF_3$, $CF_2H$, or $CFH_2$; $L_1$, $L_2$, $L_3$, and $L_4$ independently represent hydrogen atom or fluorine atom; $Z_1$ and $Z_2$ independently represent 1,2-ethylene group, —CH═CH—, or a covalent bond; and a is 1 or 2.

12. A liquid crystal composition comprising, as a first component, at least one tetracyclic compound defined in any one of claims 1–9, comprising, as a second component, at least one compound selected from the group consisting of the compounds expressed by any one of the general formulas (5), (6), (7), (8), and (9)

(5)

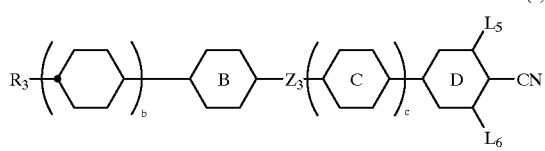

wherein $R_3$ represents fluorine atom, an alkyl group having 1 to 10 carbon atoms or an alkenyl group having 2 to 10 carbon atoms, any methylene group in the alkyl or alkenyl group may be replaced by oxygen atom, but in no case two or more methylene groups are continuously replaced by oxygen atom; ring B represents 1,4-cyclohexylene, 1,4-phenylene, or 1,3-dioxane-2,5-diyl; ring C represents 1,4-cyclohexylene, 1,4-phenylene, or pyrimidine-2,5-diyl; ring D represents 1,4-cyclohexylene or 1,4-phenylene; $Z_3$ represents 1,2-ethylene group, —COO—, or a covalent bond; $L_5$ and $L_6$ independently represent hydrogen atom or fluorine atom; and b and c are independently 0 or 1, (6)

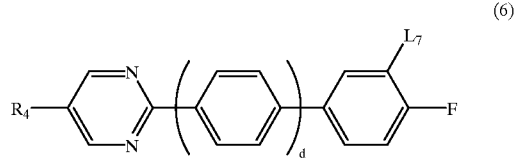

wherein $R_4$ represents an alkyl group having 1 to 10 carbon atoms; $L_7$ represents hydrogen atom or fluorine atom; and d is 0 or 1, (7)

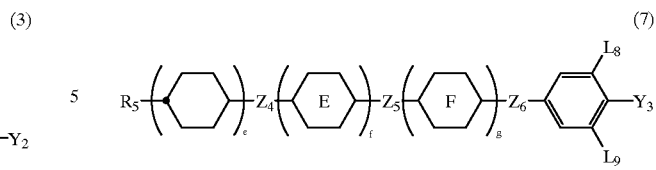

wherein $R_5$ represents an alkyl group having 1 to 10 carbon atoms; ring E and ring F independently represent 1,4-cyclohexylene or 1,4-phenylene; $Z_4$ and $Z_5$ independently represent —COO— or a covalent bond; $Z_6$ represents —COO— or —C≡C—; $L_8$ and $L_9$ independently represent hydrogen atom or fluorine atom; $Y_3$ represents fluorine atom, $OCF_3$, $OCF_2H$, $CF_3$, $CF_2H$, or $CFH_2$; and e, f, and g are independently 0 or 1, (8)

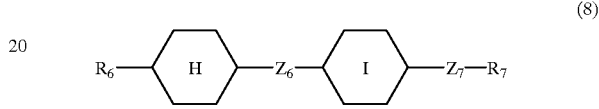

wherein $R_6$ and $R_7$ independently represent an alkyl group having 1 to 10 carbon atoms or an alkenyl group having 2 to 10 carbon atoms, any methylene group in the alkyl or alkenyl group may be replaced by oxygen atom, but in no case two or more methylene groups are continuously replaced by oxygen atom; ring H represents 1,4-cyclohexylene, 1,4-phenylene, or pyrimidine-2,5-diyl; ring I represents 1,4-cyclohexylene or 1,4-phenylene, $Z_6$ represents —C≡C—, —COO—, 1,2-ethylene group, —CH═CH—C≡C—, or a covalent bond; and $Z_7$ represents —COO— or a covalent bond, (9)

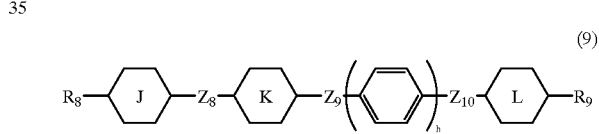

wherein $R_8$ and $R_9$ independently represent an alkyl group having 1 to 10 carbon atoms or an alkenyl group having 2 to 10 carbon atoms, any methylene group in the alkyl or alkenyl group may be replaced by oxygen atom, but in no case tow or more methylene groups are continuously replaced by oxygen atom; ring J represents 1,4-cyclohexylene, 1,4-phenylene, or pyrimidine-2,5-diyl; ring K represents 1,4-cyclohexylene, 1,4-phenylene in which one or more hydrogen atoms on the ring may be replaced by fluorine atom, or pyrimidine-2,5-diyl; ring L represents 1,4-cyclohexylene or 1,4-phenylene; $Z_8$ and $Z_{10}$ independently represent —COO—, 1,2-ethylene group, or a covalent bond; $Z_9$ represents —CH═CH—, —C≡C—, —COO—, or a covalent bond; and h is 0 or 1.

13. A liquid crystal display device comprising the liquid crystal composition defined in claim 10.

14. A liquid crystal display device comprising the liquid crystal composition defined in claim 11.

15. A liquid crystal composition comprising, as a first component, at least one tetracyclic compound defined in any one of claims 1–9, as a part of a second component, at least one compound selected from the group consisting of the compounds expressed by any one of the general formulas (2), (3), and (4), and comprising, as the other part of the second component, at least one compound selected from the group consisting of the compounds expressed by any one of the general formulas (5), (6), (7), (8) and (9), (2)

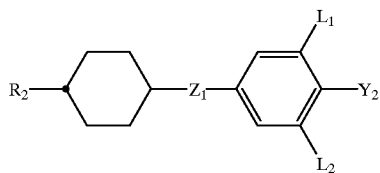

(3)

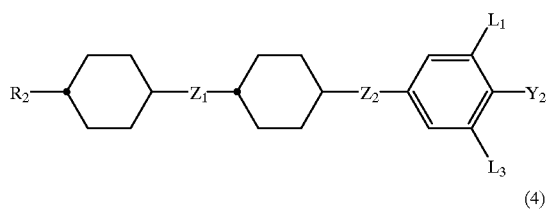

(4)

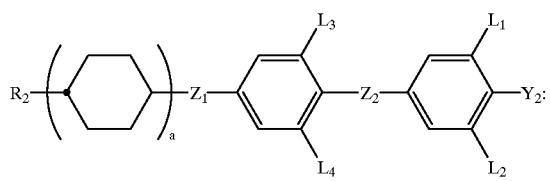

wherein $R_2$ represents an alkyl group having 1 to 10 carbon atoms; $Y_2$ represents fluorine atom, chlorine atom, $OCF_3$, $OCF_2H$, $CF_3$, $CF_2H$, or $CFH_2$; $L_1$, $L_2$, $L_3$, and $L_4$ independently represent hydrogen atom or fluorine atom; $Z_1$ and $Z_2$ independently represent 1,2-ethylene group, —CH=CH—, or a covalent bond; and a is 1 or 2, (5)

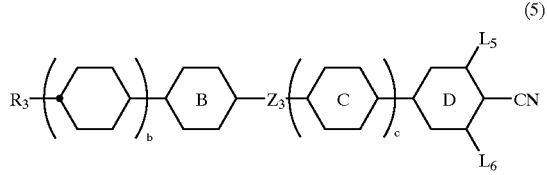

wherein $R_3$ represents fluorine atom, an alkyl group having 1 to 10 carbon atoms or an alkenyl group having 2 to 10 carbon atoms, any methylene group in the alkyl or alkenyl group may be replaced by oxygen atom, but in no case two or more methylene groups are continuously replaced by oxygen atom; ring B represents 1,4-cyclohexylene, 1,4-phenylene, or 1,3-dioxane-2,5-diyl; ring C represents 1,4-cyclohexylene, 1,4-phenylene, or pyrimidine-2,5-diyl; ring D represents 1,4-cyclohexylene or 1,4-phenylene; $Z_3$ represents 1,2-ethylene group, —COO—, or a covalent bond; $L_5$ and $L_6$ independently represent hydrogen atom or fluorine atom; and b and c are independently 0 or 1, (6)

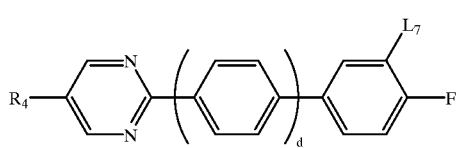

wherein $R_4$ represents an alkyl group having 1 to 10 carbon atoms; $L_7$ represents hydrogen atom or fluorine atom; and d is 0 or 1, (7)

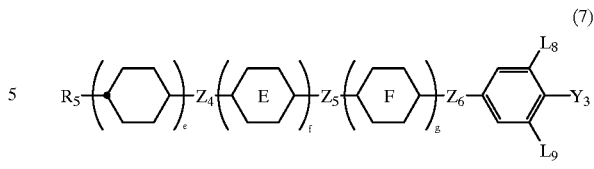

wherein $R_5$ represents an alkyl group having 1 to 10 carbon atoms; ring E and ring F independently represent 1,4-cyclohexylene or 1,4-phenylene; $Z_4$ and $Z_5$ independently represent —COO— or a covalent bond; $Z_6$ represents —COO— or —C≡C—; $L_8$ and $L_9$ independently represent hydrogen atom or fluorine atom; $Y_3$ represents fluorine atom, $OCF_3$, $OCF_2H$, $CF_3$, $CF_2H$, or $CFH_2$; and e, f, and g are independently 0 or 1, (8)

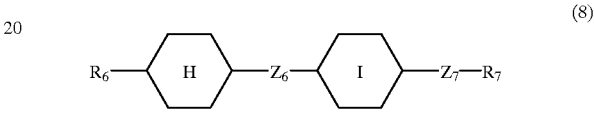

wherein $R_6$ and $R_7$ independently represent an alkyl group having 1 to 10 carbon atoms or an alkenyl group having 2 to 10 carbon atoms, any methylene group in the alkyl or alkenyl group may be replaced by oxygen atom, but in no case two or more methylene groups are continuously replaced by oxygen atom; ring H represents 1,4-cyclohexylene, 1,4-phenylene, or pyrimidine-2,5-diyl; ring I represents 1,4-cyclohexylene or 1,4-phenylene, $Z_6$ represents —C≡C—, —COO—, 1,2-ethylene group, —CH=CH—C≡C—, or a covalent bond; and $Z_7$ represents —COO— or a covalent bond, (9)

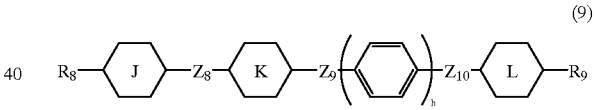

wherein $R_8$ and $R_9$ independently represent an alkyl group having 1 to 10 carbon atoms or an alkenyl group having 2 to 10 carbon atoms, any methylene group in the alkyl or alkenyl group may be replaced by oxygen atom, but in no case tow or more methylene groups are continuously replaced by oxygen atom; ring J represents 1,4-cyclohexylene, 1,4-phenylene, or pyrimidine-2,5-diyl; ring K represents 1,4-cyclohexylene, 1,4-phenylene in which one or more hydrogen atoms on the ring may be replaced by fluorine atom, or pyrimidine-2,5-diyl; ring L represents 1,4-cyclohexylene or 1,4-phenylene; $Z_8$ and $Z_{10}$ independently represent —COO—, 1,2-ethylene group, or a covalent bond; $Z_9$ represents —CH=CH—, —C≡C—, —COO—, or a covalent bond; and h is 0 or 1.

16. A liquid crystal display device comprising the liquid crystal composition defined in claim 12.

17. A liquid crystal display device comprising the liquid crystal composition defined in claim 15.

* * * * *